US012338463B2

(12) United States Patent
Garlick et al.

(10) Patent No.: US 12,338,463 B2
(45) Date of Patent: Jun. 24, 2025

(54) SINDBIS CONTROL VIRUS

(71) Applicant: LGC Clinical Diagnostics, Inc., Milford, MA (US)

(72) Inventors: Russell Garlick, Needham, MA (US); Catherine Huang, Elkridge, MD (US); Bharathi Anekella, Clarksburg, MD (US); Jonathan Li, Chestnut Hill, MA (US)

(73) Assignee: LGC Clinical Diagnostics, Inc., Milford, MA (US)

( * ) Notice: Subject to any disclaimer, the term of this patent is extended or adjusted under 35 U.S.C. 154(b) by 80 days.

(21) Appl. No.: 17/181,657

(22) Filed: Feb. 22, 2021

(65) Prior Publication Data

US 2021/0254020 A1 Aug. 19, 2021

Related U.S. Application Data

(62) Division of application No. 15/737,818, filed as application No. PCT/US2016/035751 on Jun. 3, 2016, now abandoned.

(60) Provisional application No. 62/182,104, filed on Jun. 19, 2015.

(51) Int. Cl.
*C12N 7/00* (2006.01)
*C12N 15/86* (2006.01)
*C12Q 1/70* (2006.01)

(52) U.S. Cl.
CPC ............... *C12N 7/00* (2013.01); *C12N 15/86* (2013.01); *C12Q 1/70* (2013.01); *C12N 2740/16021* (2013.01); *C12N 2740/16022* (2013.01); *C12N 2740/16031* (2013.01); *C12N 2760/16022* (2013.01); *C12N 2760/16031* (2013.01); *C12N 2770/36121* (2013.01); *C12N 2770/36143* (2013.01)

(58) Field of Classification Search
CPC .......... C12N 15/86; C12N 2740/16021; C12N 2740/16022; C12N 2740/16031; C12N 2760/16022; C12N 2760/16031; C12N 7/00; C12N 2770/36143; C12N 2770/36121; C12N 2740/15034; C12N 2740/16023; C12N 2740/16034; C12Q 1/70; A61K 2039/53; A61K 2039/6018; A61K 39/21; A61K 9/1271; A61K 2039/70; A61P 31/18; A61P 35/00; C07K 14/5434
See application file for complete search history.

(56) References Cited

U.S. PATENT DOCUMENTS 6,465,634 B1 * 10/2002 Dubensky, Jr. ........ C12N 15/86 435/320.1
6,583,121 B1 * 6/2003 Johnston ................ C12N 15/86 435/320.1
2004/0029279 A1 2/2004 Kovacs et al.
2004/0219545 A1 11/2004 Rando et al.
2009/0227658 A1 9/2009 Huang et al.
2010/0330038 A1 12/2010 Jaffrey et al.
2014/0234359 A1 8/2014 Newell et al.
2015/0050243 A1 2/2015 Kaczmarczyk et al.

FOREIGN PATENT DOCUMENTS

CN 104357581 A 2/2015
WO WO-2002/074920 9/2002
WO WO-2008/145197 A1 12/2008

OTHER PUBLICATIONS

Baronti et al. Genome Announce 2 (3), e00500-14 (2014).*
Agapov et al. Proc Natl Acad Sci U S A. Oct. 27, 1998; 95(22): 12989-12994.*
Cheng et al., "Enhancement of Sindbis Virus Self-Replicating RNA Vaccine Potency by Linkage of Herpes Simplex Virus Type 1 VP22 Protein to Antigen," J Virol, 75(5):2368-2376 (2001).
Datwyler et al., "Efficient gene delivery into adult cardiomyocytes by recombinant Sindbis virus," J Mol Med, 77:859-864 (1999).
Extended European Search Report issued by the European Patent Office in corresponding Application No. PCT/US2016035751 issued Nov. 21, 2018.
Gardner et al., "Infection of Human Dendritic Cells by a Sindbis Virus Replicon Vector Is Determined by a Single Amino Acid Substitution in the E2 Glycoprotein," Journal of Virology, 74(24): 11849-11857 (2000).
Hubuad., "RNA vaccines: a novel technology to prevent and treat disease," Harvard University the Graduate School of Arts and Sciences: 9 pages (2015).
International Search Report and Written Opinion for International Application No. PCT/US16/35751 dated Nov. 28, 2016.
Perri et al., "An Alphavirus Replicon Particle Chimera Derived from Venezuelan Equine Encephalitis and Sindbis Viruses Is a Potent Gene-Based Vaccine Delivery Vector," Journal of Virology, 77(19): 10394-10403 (2003).
Strauss et al., "Complete Nucleotide Sequence of the Genomic RNA of Sindbis Virus," Virology, 133: 92-110 (1984).
Uematsu et al., "Lack of Interference with Immunogenicity of a Chimeric Alphavirus Replicon Particle-Based Influenze Vaccine by Preexisting Antivector Immunity," Clinical and Vaccine Immunology, 19(7): 991-998 (2012).

(Continued)

*Primary Examiner* — Bao Q Li

(74) *Attorney, Agent, or Firm* — Foley Hoag LLP; Dana M. Gordon; Mohanad Mossalam

(57) ABSTRACT

Disclosed are compositions and methods related to replication deficient Sindbis viruses that are able to function as controls for nucleic acid diagnostic assays (e.g., nucleic acid sequencing based assays and/or nucleic acid amplification based assays).

11 Claims, 12 Drawing Sheets

Specification includes a Sequence Listing.

(56) References Cited

OTHER PUBLICATIONS

Zhu et al., "Induction of humoral and cellular immune responses against hepatitis C virus by vaccination with replicon particles derived from Sindbis-like virus XJ-160," Archives of Virology, 158(5):1013-1019 (2013).

Bredenbeek et al., "Sindbis Virus Expression Vectors: Packaging of RNA Replicons by Using Defective Helper RNAs," Journal of Virology, 67(11):6439-6446 (1993).

* cited by examiner

Figure 10A
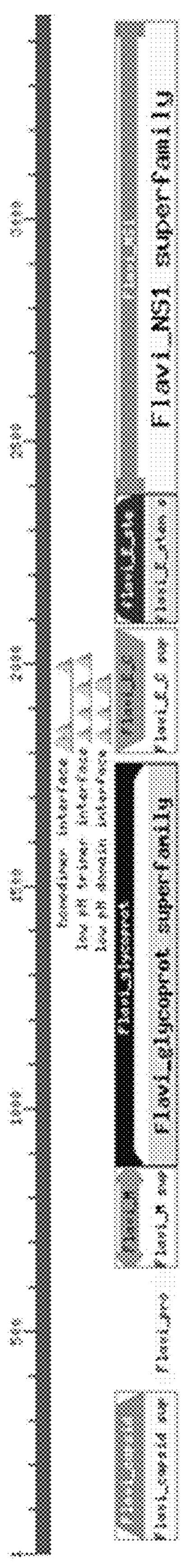
Figure 10B
Flavi_NS2A superfamily
Peptidase_S7
Peptidase_S7 superfamily
DEXDc
Figure 10C
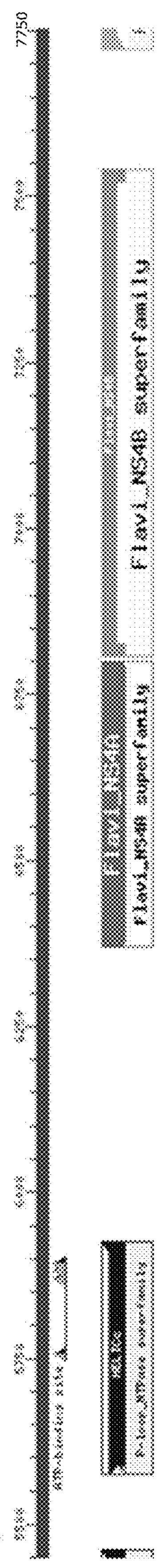
Figure 10D
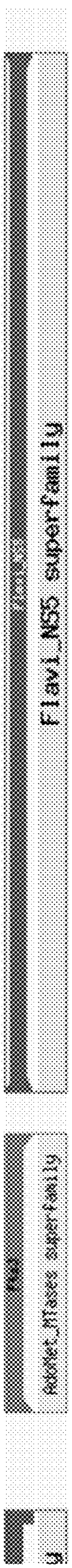

Figure 12

H7N9 Stability at Ambient Temperature

Ambient
Ambient (Fit)

copies / ml

1e+6
5e+5
0e+0

0 100 200 300 400 500 600

Days

SEQUENCE LISTING

```
<160> NUMBER OF SEQ ID NOS: 16

<210> SEQ ID NO 1
<211> LENGTH: 10052
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

attgacggcg tagtacacac tattgaatca aacagccgac caattgcact accatcacaa     60

tggagaagcc agtagtaaac gtagacgtag acccccagag tccgtttgtc gtgcaactgc    120

aaaaaagctt cccgcaattt gaggtagtag cacagcaggt cactccaaat gaccatgcta    180

atgccagagc attttcgcat ctggccagta aactaatcga gctggaggtt cctaccacag    240

cgacgatctt ggacataggc agcgcaccgg ctcgtagaat gttttccgag caccagtatc    300

attgtgtctg ccccatgcgt agtccagaag acccggaccg catgatgaaa tacgccagta    360

aactggcgga aaaagcgtgc aagattacaa acaagaactt gcatgagaag attaaggatc    420

tccggaccgt acttgatacg ccggatgctg aaacaccatc gctctgcttt cacaacgatg    480

ttacctgcaa catgcgtgcc gaatattccg tcatgcagga cgtgtatatc aacgctcccg    540

gaactatcta tcatcaggct atgaaaggcg tgcggaccct gtactggatt ggcttcgaca    600
```

```
ccacccagtt catgttctcg gctatggcag gttcgtaccc tgcgtacaac accaactggg    660
ccgacgagaa agtccttgaa gcgcgtaaca tcggactttg cagcacaaag ctgagtgaag    720
gtaggacagg aaaattgtcg ataatgagga agaaggagtt gaagcccggg tcgcgggttt    780
atttctccgt aggatcgaca ctttatccag aacacagagc cagcttgcag agctggcatc    840
ttccatcggt gttccacttg aatggaaagc agtcgtacac ttgccgctgt gatacagtgg    900
tgagttgcga aggctacgta gtgaagaaaa tcaccatcag tcccgggatc acgggagaaa    960
ccgtgggata cgcggttaca cacaatagcg agggcttctt gctatgcaaa gttactgaca   1020
cagtaaaagg agaacgggta tcgttccctg tgtgcacgta catcccggcc accatatgcg   1080
atcagatgac tggtataatg gccacggata tatcacctga cgatgcacaa aaacttctgg   1140
ttgggctcaa ccagcgaatt gtcattaacg gtaggactaa caggaacacc aacaccatgc   1200
aaaattacct tctgccgatc atagcacaag ggttcagcaa atgggctaag gagcgcaagg   1260
atgatcttga taacgagaaa atgctgggta ctagagaacg caagcttacg tatggctgct   1320
tgtgggcgtt tcgcactaag aaagtacatt cgttttatcg cccacctgga acgcagacct   1380
gcgtaaaagt cccagcctct tttagcgctt ttcccatgtc gtccgtatgg acgacctctt   1440
tgcccatgtc gctgaggcag aaattgaaac tggcattgca accaaagaag gaggaaaaac   1500
tgctgcaggt ctcggaggaa ttagtcatgg aggccaaggc tgcttttgag gatgctcagg   1560
aggaagccag agcggagaag ctccgagaag cacttccacc attagtggca gacaaaggca   1620
tcgaggcagc cgcagaagtt gtctgcgaag tggaggggct ccaggcggac atcggagcag   1680
cattagttga aaccccgcgc ggtcacgtaa ggataatacc tcaagcaaat gaccgtatga   1740
tcggacagta tatcgttgtc tcgccaaact ctgtgctgaa gaatgccaaa ctcgcaccag   1800
cgcacccgct agcagatcag gttaagatca taacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga aagaaaattg tcgcgaaatt gaggccgacg   2340
tgctaagact gaggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
ccatgcaatg cggattcttc aacatgatgc aactaaaggt acatttcaat caccctgaaa   2580
aagacatatg caccaagaca ttctacaagt atatctcccg gcgttgcaca cagccagtta   2640
cagctattgt atcgacactg cattacgatg gaaagatgaa aaccacgaac ccgtgcaaga   2700
agaacattga aatcgatatt acaggggcca caaagccgaa gccaggggat atcatcctga   2760
catgtttccg cgggtgggtt aagcaattgc aaatcgacta tcccggacat gaagtaatga   2820
cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag cccactaaca   3000
```

```
tacctaaagg aaactttcag gctactatag aggactggga agctgaacac aagggaataa   3060
ttgctgcaat aaacagcccc actccccgtg ccaatccgtt cagctgcaag accaacgttt   3120
gctgggcgaa agcattggaa ccgatactag ccacggccgg tatcgtactt accggttgcc   3180
agtggagcga actgttccca cagtttgcgg atgacaaacc acattcggcc atttacgcct   3240
tagacgtaat ttgcattaag tttttcggca tggacttgac aagcggactg ttttctaaac   3300
agagcatccc actaacgtac catcccgccg attcagcgag gccggtagct cattgggaca   3360
acagcccagg aacccgcaag tatgggtacg atcacgccat tgccgccgaa ctctcccgta   3420
gatttccggt gttccagcta gctgggaagg gcacacaact tgatttgcag acggggagaa   3480
ccagagttat ctctgcacag cataacctgg tcccggtgaa ccgcaatctt cctcacgcct   3540
tagtccccga gtacaaggag aagcaacccg gcccggtcaa aaaattcttg aaccagttca   3600
aacaccactc agtacttgtg gtatcagagg aaaaaattga agctccccgt aagagaatcg   3660
aatggatcgc cccgattggc atagccggtg cagataagaa ctacaacctg gctttcgggt   3720
ttccgccgca ggcacggtac gacctggtgt tcatcaacat tggaactaaa tacagaaacc   3780
accactttca gcagtgcgaa gaccatgcgg cgaccttaaa aaccctttcg cgttcggccc   3840
tgaattgcct taacccagga ggcaccctcg tggtgaagtc ctatggctac gccgaccgca   3900
acagtgagga cgtagtcacc gctcttgcca gaaagtttgt cagggtgtct gcagcgagac   3960
cagattgtgt ctcaagcaat acagaaatgt acctgatttt ccgacaacta gacaacagcc   4020
gtacacggca attcaccccg caccatctga attgcgtgat ttcgtccgtg tatgagggta   4080
caagagatgg agttggagcc gcgccgtcat accgcaccaa aagggagaat attgctgact   4140
gtcaagagga agcagttgtc aacgcagcca atccgctggg tagaccaggc gaaggagtct   4200
gccgtgccat ctataaacgt tggccgacca gttttaccga ttcagccacg gagacaggca   4260
ccgcaagaat gactgtgtgc ctaggaaaga aagtgatcca cgcggtcggc cctgatttcc   4320
ggaagcaccc agaagcagaa gccttgaaat tgctacaaaa cgcctaccat gcagtggcag   4380
acttagtaaa tgaacataac atcaagtctg tcgccattcc actgctatct acaggcattt   4440
acgcagccgg aaaagaccgc cttgaagtat cacttaactg cttgacaacc gcgctagaca   4500
gaactgacgc ggacgtaacc atctattgcc tggataagaa gtggaaggaa agaatcgacg   4560
cggcactcca acttaaggag tctgtaacag agctgaagga tgaagatatg gagatcgacg   4620
atgagttagt atggattcat ccagacagtt gcttgaaggg aagaaaggga ttcagtacta   4680
caaaaggaaa attgtattcg tacttcgaag gcaccaaatt ccatcaagca gcaaaagaca   4740
tggcggagat aaaggtcctg ttccctaatg accaggaaag taatgaacaa ctgtgtgcct   4800
acatattggg tgagaccatg gaagcaatcc gcgaaaagtg cccggtcgac cataacccgt   4860
cgtctagccc gcccaaaacg ttgccgtgcc tttgcatgta tgccatgacg ccagaaaggg   4920
tccacagact tagaagcaat aacgtcaaag aagttacagt atgctcctcc acccccccttc  4980
ctaagcacaa aattaagaat gttcagaagg ttcagtgcac gaaagtagtc ctgtttaatc   5040
cgcacactcc cgcattcgtt cccgcccgta agtacataga agtgccagaa cagcctaccg   5100
ctcctcctgc acaggccgag gaggccccccg aagttgtagc gacaccgtca ccatctacag  5160
ctgataacac ctcgcttgat gtcacagaca tctcactgga tatggatgac agtagcgaag   5220
gctcactttt ttcgagcttt agcggatcgg acaactctat tactagtatg gacagttggt   5280
cgtcaggacc tagttcacta gagatagtag accgaaggca ggtggtggtg gctgacgttc   5340
```

-continued

```
atgccgtcca agagcctgcc cctattccac cgccaaggct aaagaagatg gcccgcctgg   5400
cagcggcaag aaaagagccc actccaccgg caagcaatag ctctgagtcc ctccacctct   5460
cttttggtgg ggtatccatg tccctcggat caattttcga cggagagacg gcccgccagg   5520
cagcggtaca acccctggca acaggcccca cggatgtgcc tatgtctttc ggatcgtttt   5580
ccgacggaga gattgatgag ctgagccgca gagtaactga gtccgaaccc gtcctgtttg   5640
gatcatttga accgggcgaa gtgaactcaa ttatatcgtc ccgatcagcc gtatcttttc   5700
cactacgcaa gcagagacgt agacgcagga gcaggaggac tgaatactga ctaaccgggg   5760
taggtgggta catattttcg acggacacag gccctgggca cttgcaaaag aagtccgttc   5820
tgcagaacca gcttacagaa ccgaccttgg agcgcaatgt cctggaaaga attcatgccc   5880
cggtgctcga cacgtcgaaa gaggaacaac tcaaactcag gtaccagatg atgcccaccg   5940
aagccaacaa aagtaggtac cagtctcgta aagtagaaaa tcagaaagcc ataaccactg   6000
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact tggatatggt agacgggaca gtcgcctgcc   6240
tggatactgc aaccttctgc cccgctaagc ttagaagtta cccgaaaaaa catgagtata   6300
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgac attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
aagaagtgcc tatggataga ttcgtcatgg acatgaaaag agacgtgaaa gttacaccag   6660
gcacgaaaca cacagaagaa agaccgaaag tacaagtgat acaagccgca gaacccctgg   6720
cgactgctta cttatgcggg attcaccggg aattagtgcg taggcttacg gccgtcttgc   6780
ttccaaacat tcacacgctt tttgacatgt cggcggagga ttttgatgca atcatagcag   6840
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga aatccggaat gttcctcaca ctttttgtca   7080
acacagtttt gaatgtcgtt atcgccagca gagtactaga agagcggctt aaaacgtcca   7140
gatgtgcagc gttcattggc gacgacaaca tcatacatgg agtagtatct gacaaagaaa   7200
tggctgagag gtgcgccacc tggctcaaca tggaggttaa gatcatcgac gcagtcatcg   7260
gtgagagacc accttacttc tgcggcggat ttatcttgca agattcggtt acttccacag   7320
cgtgccgcgt ggcggatccc ctgaaaaggc tgtttaagtt gggtaaaccg ctcccagccg   7380
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt ttgcccagag caaaagagca ttccaagcca   7560
tcagagggga aataaagcat ctctacggtg gtcctaaata gtcagcatag tacatttcat   7620
ctgactaata ctacaacacc accacctcta gagtttaaac aggcctggcg cgccacgtga   7680
cgcgtgcatg catttaaata tcgagggcag gagcgagagg gccaaggcca gggagggcgg   7740
```

```
ccaccaccat caccaccatc accattagta atgaggtaac cgtggggccc aatgatccga   7800
ccagcaaaac tcgatgtact tccgaggaac tgatgtgcat aatgcatcag gctggtacat   7860
tagatccccg cttaccgcgg gcaatatagc aacactaaaa actcgatgta cttccgagga   7920
agcgcagtgc ataatgctgc gcagtgttgc cacataacca ctatattaac catttatcta   7980
gcggacgcca aaaactcaat gtatttctga ggaagcgtgg tgcataatgc cacgcagcgt   8040
ctgcataact tttattattt cttttattaa tcaacaaaat tttgttttta acatttcaaa   8100
aaaaaaaaaa aaaaaaaaaa aaaaaaaaaa aaaagggaat tcctcgatta attaagcggc   8160
cgctcgaggg gaattaattc ttgaagacga aagggccagg tggcactttt cggggaaatg   8220
tgcgcggaac ccctatttgt ttatttttct aaatacattc aaatatgtat ccgctcatga   8280
gacaataacc ctgataaatg cttcaataat attgaaaaag gaagagtatg agtattcaac   8340
atttccgtgt cgcccttatt cccttttttg cggcattttg ccttcctgtt tttgctcacc   8400
cagaaacgct ggtgaaagta aaagatgctg aagatcagtt gggtgcacga gtgggttaca   8460
tcgaactgga tctcaacagc ggtaagatcc ttgagagttt tcgccccgaa gaacgttttc   8520
caatgatgag cacttttaaa gttctgctat gtggcgcggt attatcccgt gttgacgccg   8580
ggcaagagca actcggtcgc cgcatacact attctcagaa tgacttggtt gagtactcac   8640
cagtcacaga aaagcatctt acggatggca tgacagtaag agaattatgc agtgctgcca   8700
taaccatgag tgataacact gcggccaact tacttctgac aacgatcgga ggaccgaagg   8760
agctaaccgc ttttttgcac aacatggggg atcatgtaac tcgccttgat cgttgggaac   8820
cggagctgaa tgaagccata ccaaacgacg agcgtgacac cacgatgcct gtagcaatgg   8880
caacaacgtt gcgcaaacta ttaactggcg aactacttac tctagcttcc cggcaacaat   8940
taatagactg gatggaggcg gataaagttg caggaccact tctgcgctcg gcccttccgg   9000
ctggctggtt tattgctgat aaatctggag ccggtgagcg tgggtctcgc ggtatcattg   9060
cagcactggg gccagatggt aagccctccc gtatcgtagt tatctacacg acggggagtc   9120
aggcaactat ggatgaacga aatagacaga tcgctgagat aggtgcctca ctgattaagc   9180
attggtaact gtcagaccaa gtttactcat atatacttta gattgattta aaacttcatt   9240
tttaatttaa aaggatctag gtgaagatcc tttttgataa tctcatgacc aaaatccctt   9300
aacgtgagtt ttcgttccac tgagcgtcag accccgtaga aaagatcaaa ggatcttctt   9360
gagatccttt ttttctgcgc gtaatctgct gcttgcaaac aaaaaaacca ccgctaccag   9420
cggtggtttg tttgccggat caagagctac caactctttt tccgaaggta actggcttca   9480
gcagagcgca gataccaaat actgtccttc tagtgtagcc gtagttaggc caccacttca   9540
agaactctgt agcaccgcct acatacctcg ctctgctaat cctgttacca gtggctgctg   9600
ccagtggcga taagtcgtgt cttaccgggt tggactcaag acgatagtta ccggataagg   9660
cgcagcggtc gggctgaacg gggggttcgt gcacacagcc cagcttggag cgaacgacct   9720
acaccgaact gagataccta cagcgtgagc attgagaaag cgccacgctt cccgaaggga   9780
gaaaggcgga caggtatccg gtaagcggca gggtcggaac aggagagcgc acgagggagc   9840
ttccaggggg aaacgcctgg tatctttata gtcctgtcgg gtttcgccac ctctgacttg   9900
agcgtcgatt tttgtgatgc tcgtcagggg ggcggagcct atggaaaaac gccagcaacg   9960
cgagctcgta tggacatatt gtcgttagaa cgcggctaca attaatacat aaccttatgt  10020
atcatacaca tacgatttag ggacactat ag                                10052
```

<210> SEQ ID NO 2
<211> LENGTH: 1950
<212> TYPE: DNA
<213> ORGANISM: Zaire ebolavirus

<400> SEQUENCE: 2

```
aggaatattg cagttacctc gtgatcgatt caagaggaca tcattctttc tttgggtaat      60
tatccttttc caaagaacat tttccatccc gcttggagtt atccacaata gtacattaca     120
ggttagtgat gtcgacaaac tagtttgtcg tgacaaactg tcatccacaa atcaattgag     180
atcagttgga ctgaatctcg aggggaatgg agtggcaact gacgtgccat ctgcgactaa     240
aagatggggc ttcaggtccg gtgtcccacc aaaggtggtc aattatgaag ctggtgaatg     300
ggctgaaaac tgctacaatc ttgaaatcaa aaaacctgac gggagtgagt gtctaccagc     360
agcgccagac gggattcggg gcttcccccg gtgccggtat gtgcacaaag tatcaggaac     420
gggaccatgt gccggagact ttgccttcca caaagagggt gctttcttcc tgtatgatcg     480
acttgcttcc acagttatct accgaggaac gactttcgct gaaggtgtcg ttgcatttct     540
gatactgccc caagctaaga aggacttctt cagctcacac cccttgagag agccggtcaa     600
tgcaacggag gacccgtcga gtggctatta ttctaccaca attagatatc aggctaccgg     660
ttttggaact aatgagacag agtacttgtt cgaggttgac aatttgacct acgtccaact     720
tgaatcaaga ttcacaccac agtttctgct ccagctgaat gagacaatat atgcaagtgg     780
gaagaggagc aacaccacgg gaaaactaat ttggaaggtc aaccccgaaa ttgatacaac     840
aatcggggag tgggccttca gggaaactaa aaaaacctca ctagaaaaat tcgcagtgaa     900
gagttgtctt tcacagctgt atcaaacgga cccaaaaaca tcagtggtca gagtccggcg     960
cgaacttctt ccgacccaga gaccaacaca acaaatgaag accacaaaat catggcttca    1020
gaaaattcct ctgcaatggt tcaagtgcac agtcaaggaa ggaaagctgc agtgtcgcat    1080
ctgacaaccc ttgccacaat ctccacgagt cctcaacctc ccacaaccaa aacaggtccg    1140
gacaacagca cccataatac acccgtgtat aaacttgaca tctctgaggc aactcaagtt    1200
ggacaacatc accgtagagc agacaacgac agcacagcct ccgacactcc ccccgccacg    1260
accgcagccg gacccttaaa agcagagaac accaacacga gtaagagcgc tgactccctg    1320
gacctcgcca ccacgataag cccccaaaac tacagcgaga ctgctggcaa caacaacact    1380
catcaccaag ataccggaga agagagtgcc agcagcggga agctaggctt aattaccaat    1440
actattgctg gagtagcagg actgatcaca ggcgggagaa ggactcgaag agaagtaatt    1500
gtcaatgctc aacccaaatg caaccccaat ttacattact ggactactca ggatgaaggt    1560
gctgcaatcg gattggcctg gataccatat ttcgggccag cagccgaagg aatttacaca    1620
gaggggctaa tgcacaacca agatggttta atctgtgggt tgaggcagct ggccaacgaa    1680
acgactcaag ctctccaact gttcctgaga gccacaactg agctgcgaac cttttcaatc    1740
ctcaaccgta aggcaattga cttcctgctg cagcgatggg gtggcacatg ccacattttg    1800
ggaccggact gctgtatcga accacatgat tggaccaaga acataacaga caaaattgat    1860
cagattattc atgattttgt tgataaaacc cttccggacc aggggggacaa tgacaattgg    1920
tggacaggat ggagacaatg gataccggca                                    1950
```

<210> SEQ ID NO 3
<211> LENGTH: 2217
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: MISC_FEATURE
<222> LOCATION: (1)..(1577)
<223> OTHER INFORMATION: Ebola NP gene sequence
<220> FEATURE:
<221> NAME/KEY: MISC_FEATURE
<222> LOCATION: (1578)..(2127)
<223> OTHER INFORMATION: Ebola VP24 sequence
<220> FEATURE:
<221> NAME/KEY: MISC_FEATURE
<222> LOCATION: (2128)..(2217)
<223> OTHER INFORMATION: Human RNAse P internal control sequence

<400> SEQUENCE: 3

```
tactgtaatc atacctggtt tgtttcagag ccatatcacc aagatagaga acaacctagg     60
tctccggagg gggcaagggc atcagtgtgc tcagttgaaa atcccttgtc aacatctagg    120
ccttatcaca tcacaagttc cgccttaaac tctgcagggt gatccaacaa ccttaatagc    180
aacattattg ttaaaggaca gcattagttc acagtcaaac aagcaagatt gagaattaac    240
tttgattttg aacctgaaca cccagaggac tggagactca acaaccctaa agcctggggt    300
aaaacattag aaatagttta aagacaaatt gctcggaatc acaaaattcc gagtatggat    360
tctcgtcctc agaaagtctg gtagacgccg agtctcactg aatctgacat ggattaccac    420
aagatcttga cagcaggtct gtccgttcaa caggggattg ttcggcaaag agtcatccca    480
gtgtatcaag taaacaatct tgaggaaatt tgccaactta tcatacaggc ctttgaagct    540
ggtgttgatt ttcaagagag tgcggacagt ttccttctca tgctttgtct tcatcatgcg    600
taccaaggag attacaaact tttcttggaa agtggcgcag tcaagtattt ggaagggcac    660
gggttccgtt ttgaagtcaa gaagcgtgat ggagtgaagc gccttgagga attgctgcca    720
gcagtatcta gtgggagaaa cattaagaga acacttgctg ccatgccgga agaggagacg    780
acttaatgcc ggacatgatg ccaacgatgc tgtgatttca aattcagtgg ctcaagctcg    840
tttttcaggt ctattgattg tcaaaacagt acttgatcat atcctacaaa agacagaacg    900
aggagttcgt ctccatcctc ttgcaaggac cgccaaggta aaaaatgagg tgaactcctt    960
caaggctgca ctcagctccc tggccaagca tggagagtat gctcctttcg cccgactttt   1020
gaacctttct ggagtaaata atcttgagca tggtcttttc cctcaactgt cggcaattgc   1080
actcggagtc gccacagccc acgggagcac cctcgcagga gtaaatgttg gagaacagta   1140
tcaacagctc agagaggcag ccactgaggc tgagaagcaa ctccaacaat atgcggagtc   1200
tcgtgaactt gaccatcttg gacttgatga tcaggaaaag aaaattctta tgaacttcca   1260
tcagaaaaag aacgaaatca gcttccagca aacaaacgcg atggtaactc taagaaaaga   1320
gcgcctggcc aagctgacag aagctatcac tgctgcatca ctgcccaaaa caagtggaca   1380
ttacgatgat gatgacgaca ttccctttcc aggacccatc aatgatgacg acaatcctgg   1440
ccatcaagat gatgatccga ctgactcaca ggatacgacc attcccgatg tggtagttga   1500
tcccgatgat ggaggctacg gcgaatacca aagttactcg gaaaacggca tgagtgcacc   1560
agatgacttg gtcctatgtc ttttagctgt ataccagttg cccctgagat acgccacaaa   1620
agtgtctctg agctaaagtg gtctgtacac atctcataca ttgtattagg ggcaataata   1680
tctaattgaa cttagccatt taaaatttag tgcataaatc tgggctaact ccaccaggtc   1740
aactccattg gctgaaaaga agcccaccta caacgaacat tactttgagc gccctcacaa   1800
ttaaaaaata agagcgtcgt tccaacaatc gagcgcaagg ttacaaggtt gaactgagag   1860
```

```
tgtctagaca acaaaatatc gatactccag acaccaagca agacctgaga aaaaaccatg   1920

gccaaagcta cgggacgata caatctaata tcgcccaaaa aggacctgga gaaaggggtt   1980

gtcttaagcg acctctgtaa cttcttagtt agtcaaacta ttcaagggtg gaaagtttat   2040

tgggctggta ttgagtttga tgtgactcac aaaggaatgg ccctattgca tagactgaaa   2100

actaatgact ttgcccctgc atggtcatgg cggtgtttgc agatttggac ctgcgagcgg   2160

gttctgacct gaaggctctg cgcggacttg tggagacagc cgctcacctt ggctatt      2217
```

<210> SEQ ID NO 4
<211> LENGTH: 9719
<212> TYPE: DNA
<213> ORGANISM: Human immunodeficiency virus

<400> SEQUENCE: 4

```
tggaagggct aattcactcc caacgaagac aagatatcct tgatctgtgg atctaccaca     60

cacaaggcta cttccctgat tagcagaact acacaccagg gccagggatc agatatccac    120

tgacctttgg atggtgctac aagctagtac cagttgagcc agagaagtta gaagaagcca    180

acaaaggaga gaacaccagc ttgttacacc ctgtgagcct gcatggaatg gatgacccgg    240

agagagaagt gttagagtgg aggtttgaca gccgcctagc atttcatcac atggcccgag    300

agctgcatcc ggagtacttc aagaactgct gacatcgagc ttgctacaag ggactttccg    360

ctggggactt tccagggagg cgtggcctgg gcgggactgg ggagtggcga gccctcagat    420

cctgcatata agcagctgct ttttgcctgt actgggtctc tctggttaga ccagatctga    480

gcctgggagc tctctggcta actagggaac ccactgctta agcctcaata aagcttgcct    540

tgagtgcttc aagtagtgtg tgcccgtctg ttgtgtgact ctggtaacta gagatccctc    600

agaccctttt agtcagtgtg gaaaatctct agcagtggcg cccgaacagg gacctgaaag    660

cgaaagggaa accagaggag ctctctcgac gcaggactcg gcttgctgaa gcgcgcacgg    720

caagaggcga ggggcggcga ctggtgagta cgccaaaaat tttgactagc ggaggctaga    780

aggagagaga tgggtgcgag agcgtcagta ttaagcgggg gagaattaga tcgatgggaa    840

aaaattcggt taaggccagg gggaaagaaa aaatataaat taaaacatat agtatgggca    900

agcagggagc tagaacgatt cgcagttaat cctggcctgt tagaaacatc agaaggctgt    960

agacaaatac tgggacagct acaaccatcc cttcagacag gatcagaaga acttagatca   1020

ttatataata cagtagcaac cctctattgt gtgcatcaaa ggatagagat aaaagacacc   1080

aaggaagctt tagacaagat agaggaagag caaaacaaaa gtaagaaaaa agcacagcaa   1140

gcagcagctg acacaggaca cagcaatcag gtcagccaaa attaccctat agtgcagaac   1200

atccaggggc aaatggtaca tcaggccata tcacctagaa ctttaaatgc atgggtaaaa   1260

gtagtagaag agaaggcttt cagcccagaa gtgataccca tgttttcagc attatcagaa   1320

ggagccaccc cacaagattt aaacaccatg ctaaacacag tggggggaca tcaagcagcc   1380

atgcaaatgt taaaagagac catcaatgag gaagctgcag aatgggatag agtgcatcca   1440

gtgcatgcag ggcctattgc accaggccag atgagagaac caaggggaag tgacatagca   1500

ggaactacta gtacccttca ggaacaaata ggatggatga caaataatcc acctatccca   1560

gtaggagaaa tttataaaag atggataatc ctgggattaa ataaaatagt aagaatgtat   1620

agccctacca gcattctgga cataagacaa ggaccaaagg aaccctttag agactatgta   1680

gaccggttct ataaaactct aagagccgag caagcttcac aggaggtaaa aaattggatg   1740
```

-continued

```
acagaaacct tgttggtcca aaatgcgaac ccagattgta agactatttt aaaagcattg   1800
ggaccagcgg ctacactaga agaaatgatg acagcatgtc agggagtagg aggacccggc   1860
cataaggcaa gagttttggc tgaagcaatg agccaagtaa caaattcagc taccataatg   1920
atgcagagag gcaattttag gaaccaaaga aagattgtta agtgtttcaa ttgtggcaaa   1980
gaagggcaca cagccagaaa ttgcagggcc cctaggaaaa agggctgttg gaaatgtgga   2040
aaggaaggac accaaatgaa agattgtact gagagacagg ctaatttttt agggaagatc   2100
tggccttcct acaagggaag gccagggaat tttcttcaga gcagaccaga gccaacagcc   2160
ccaccagaag agagcttcag gtctggggta gagacaacaa ctccccctca gaagcaggag   2220
ccgatagaca aggaactgta tcctttaact tccctcaggt cactctttgg caacgacccc   2280
tcgtcacaat aaagataggg gggcaactaa aggaagctct attagataca ggagcagatg   2340
atacagtatt agaagaaatg agtttgccag gaagatggaa accaaaaatg atagggggaa   2400
ttggaggttt tatcaaagta agacagtatg atcagatact catagaaatc tgtggacata   2460
aagctatagg tacagtatta gtaggaccta cacctgtcaa cataattgga agaaatctgt   2520
tgactcagat tggttgcact ttaaattttc ccattagccc tattgagact gtaccagtaa   2580
aattaaagcc aggaatggat ggcccaaaag ttaaacaatg gccattgaca gaagaaaaaa   2640
taaaagcatt agtagaaatt tgtacagaga tggaaaagga agggaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagacttc tgggaagttc   2820
aattaggaat accacatccc gcagggttaa aaaagaaaaa atcagtaaca gtactggatg   2880
tgggtgatgc atatttttca gttcccttag atgaagactt caggaagtat actgcattta   2940
ccatacctag tataaacaat gagacaccag ggattagata tcagtacaat gtgcttccac   3000
agggatggaa aggatcacca gcaatattcc aaagtagcat gacaaaaatc ttagagcctt   3060
ttagaaaaca aaatccagac atagttatct atcaatacat ggatgatttg tatgtaggat   3120
ctgacttaga aatagggcag catagaacaa aaatagagga gctgagacaa catctgttga   3180
ggtggggact taccacacca gacaaaaaac atcagaaaga acctccattc ctttggatgg   3240
gttatgaact ccatcctgat aaatggacag tacagcctat agtgctgcca gaaaaagaca   3300
gctggactgt caatgacata cagaagttag tggggaaatt gaattgggca agtcagattt   3360
acccagggat taaagtaagg caattatgta aactccttag aggaaccaaa gcactaacag   3420
aagtaatacc actaacagaa gaagcagagc tagaactggc agaaaacaga gagattctaa   3480
aagaaccagt acatggagtg tattatgacc catcaaaaga cttaatagca gaaatacaga   3540
agcaggggca aggccaatgg acatatcaaa tttatcaaga gccatttaaa aatctgaaaa   3600
caggaaaata tgcaagaatg aggggtgccc acactaatga tgtaaaacaa ttaacagagg   3660
cagtgcaaaa aataaccaca gaaagcatag taatatgggg aaagactcct aaatttaaac   3720
tgcccataca aaaggaaaca tgggaaacat ggtggacaga gtattggcaa gccacctgga   3780
ttcctgagtg ggagtttgtt aatacccctc ccttagtgaa attatggtac cagttagaga   3840
aagaacccat agtaggagca gaaaccttct atgtagatgg ggcagctaac agggagacta   3900
aattaggaaa agcaggatat gttactaata gaggaagaca aaaagttgtc accctaactg   3960
acacaacaaa tcagaagact gagttacaag caatttatct agctttgcag gattcgggat   4020
tagaagtaaa catagtaaca gactcacaat atgcattagg aatcattcaa gcacaaccag   4080
atcaaagtga atcagagtta gtcaatcaaa taatagagca gttaataaaa aaggaaaagg   4140
```

-continued

```
tctatctggc atgggtacca gcacacaaag gaattggagg aaatgaacaa gtagataaat   4200
tagtcagtgc tggaatcagg aaagtactat ttttagatgg aatagataag gcccaagatg   4260
aacatgagaa atatcacagt aattggagag caatggctag tgattttaac ctgccacctg   4320
tagtagcaaa agaaatagta gccagctgtg ataaatgtca gctaaaagga gaagccatgc   4380
atggacaagt agactgtagt ccaggaatat ggcaactaga ttgtacacat ttagaaggaa   4440
aagttatcct ggtagcagtt catgtagcca gtggatatat agaagcagaa gttattccag   4500
cagaaacagg gcaggaaaca gcatattttc ttttaaaatt agcaggaaga tggccagtaa   4560
aaacaataca tactgacaat ggcagcaatt tcaccggtgc tacggttagg gccgcctgtt   4620
ggtgggcggg aatcaagcag gaatttggaa ttccctacaa tccccaaagt caaggagtag   4680
tagaatctat gaataaagaa ttaaagaaaa ttataggaca ggtaagagat caggctgaac   4740
atcttaagac agcagtacaa atggcagtat tcatccacaa ttttaaaaga aaagggggga   4800
ttggggggta cagtgcaggg gaaagaatag tagacataat agcaacagac atacaaacta   4860
aagaattaca aaaacaaatt acaaaaattc aaaattttcg ggtttattac agggacagca   4920
gaaatccact ttggaaagga ccagcaaagc tcctctggaa aggtgaaggg gcagtagtaa   4980
tacaagataa tagtgacata aaagtagtgc caagaagaaa agcaaagatc attagggatt   5040
atggaaaaca gatggcaggt gatgattgtg tggcaagtag acaggatgag gattagaaca   5100
tggaaaagtt tagtaaaaca ccatatgtat gtttcaggga aagctagggg atggttttat   5160
agacatcact atgaaagccc tcatccaaga ataagttcag aagtacacat cccactaggg   5220
gatgctagat tggtaataac aacatattgg ggtctgcata caggagaaag agactggcat   5280
ttgggtcagg gagtctccat agaatggagg aaaaagagat atagcacaca agtagaccct   5340
gaactagcag accaactaat tcatctgtat tactttgact gtttttcaga ctctgctata   5400
agaaaggcct tattaggaca catagttagc cctaggtgtg aatatcaagc aggacataac   5460
aaggtaggat ctctacaata cttggcacta gcagcattaa taacaccaaa aaagataaag   5520
ccacctttgc ctagtgttac gaaactgaca gaggatagat ggaacaagcc ccagaagacc   5580
aagggccaca gagggagcca cacaatgaat ggacactaga gcttttagag gagcttaaga   5640
atgaagctgt tagacatttt cctaggattt ggctccatgg cttagggcaa catatctatg   5700
aaacttatgg ggatacttgg gcaggagtgg aagccataat aagaattctg caacaactgc   5760
tgtttatcca ttttcagaat tgggtgtcga catagcagaa taggcgttac tcgacagagg   5820
agagcaagaa atggagccag tagatcctag actagagccc tggaagcatc caggaagtca   5880
gcctaaaact gcttgtacca attgctattg taaaaagtgt tgctttcatt gccaagtttg   5940
tttcataaca aaagccttag gcatctccta tggcaggaag aagcggagac agcgacgaag   6000
agctcatcag aacagtcaga ctcatcaagc ttctctatca aagcagtaag tagtacatgt   6060
aacgcaacct ataccaatag tagcaatagt agcattagta gtagcaataa taatagcaat   6120
agttgtgtgg tccatagtaa tcatagaata taggaaaata ttaagacaaa gaaaaataga   6180
caggttaatt gatagactaa tagaaagagc agaagacagt ggcaatgaga gtgaaggaga   6240
aatatcagca cttgtggaga tgggggtgga gatggggcac catgctcctt gggatgttga   6300
tgatctgtag tgctacagaa aaattgtggg tcacagtcta ttatggggta cctgtgtgga   6360
aggaagcaac caccactcta ttttgtgcat cagatgctaa agcatatgat acagaggtac   6420
ataatgtttg ggccacacat gcctgtgtac ccacagaccc caacccacaa gaagtagtat   6480
```

-continued

```
tggtaaatgt gacagaaaat tttaacatgt ggaaaaatga catggtagaa cagatgcatg   6540
aggatataat cagtttatgg gatcaaagcc taaagccatg tgtaaaatta accccactct   6600
gtgttagttt aaagtgcact gatttgaaga atgatactaa taccaatagt agtagcggga   6660
gaatgataat ggagaaagga gagataaaaa actgctcttt caatatcagc acaagcataa   6720
gaggtaaggt gcagaaagaa tatgcatttt tttataaact tgatataata ccaatagata   6780
atgatactac cagctataag ttgacaagtt gtaacacctc agtcattaca caggcctgtc   6840
caaaggtatc ctttgagcca attcccatac attattgtgc cccggctggt tttgcgattc   6900
taaaatgtaa taataagacg ttcaatggaa caggaccatg tacaaatgtc agcacagtac   6960
aatgtacaca tggaattagg ccagtagtat caactcaact gctgttaaat ggcagtctag   7020
cagaagaaga ggtagtaatt agatctgtca atttcacgga caatgctaaa accataatag   7080
tacagctgaa cacatctgta gaaattaatt gtacaagacc caacaacaat acaagaaaaa   7140
gaatccgtat ccagagagga ccagggagag catttgttac aataggaaaa ataggaaata   7200
tgagacaagc acattgtaac attagtagag caaaatggaa taacacttta aaacagatag   7260
ctagcaaatt aagagaacaa tttggaaata ataaaacaat aatctttaag caatcctcag   7320
gaggggaccc agaaattgta acgcacagtt ttaattgtgg aggggaattt ttctactgta   7380
attcaacaca actgtttaat agtacttggt ttaatagtac ttggagtact gaagggtcaa   7440
ataacactga aggaagtgac acaatcaccc tcccatgcag aataaaacaa attataaaca   7500
tgtggcagaa agtaggaaaa gcaatgtatg cccctcccat cagtggacaa attagatgtt   7560
catcaaatat tacagggctg ctattaacaa gagatggtgg taatagcaac aatgagtccg   7620
agatcttcag acctggagga ggagatatga gggacaattg gagaagtgaa ttatataaat   7680
ataaagtagt aaaaattgaa ccattaggag tagcacccac caaggcaaag agaagagtgg   7740
tgcagagaga aaaaagagca gtgggaatag gagctttgtt ccttgggttc ttgggagcag   7800
caggaagcac tatgggcgca gcctcaatga cgctgacggt acaggccaga caattattgt   7860
ctggtatagt gcagcagcag aacaatttgc tgagggctat tgaggcgcaa cagcatctgt   7920
tgcaactcac agtctggggc atcaagcagc tccaggcaag aatcctggct gtggaaagat   7980
acctaaagga tcaacagctc ctggggattt ggggttgctc tggaaaactc atttgcacca   8040
ctgctgtgcc ttggaatgct agttggagta ataaatctct ggaacagatt tggaatcaca   8100
cgacctggat ggagtgggac agagaaatta acaattacac aagcttaata cactccttaa   8160
ttgaagaatc gcaaaaccag caagaaaaga atgaacaaga attattggaa ttagataaat   8220
gggcaagttt gtggaattgg tttaacataa caaattggct gtggtatata aaattattca   8280
taatgatagt aggaggcttg gtaggtttaa gaatagtttt tgctgtactt tctatagtga   8340
atagagttag gcagggatat tcaccattat cgtttcagac ccacctccca accccgaggg   8400
gacccgacag gcccgaagga atagaagaag aaggtggaga gagagacaga gacagatcca   8460
ttcgattagt gaacggatcc ttggcactta tctgggacga tctgcggagc ctgtgcctct   8520
tcagctacca ccgcttgaga gacttactct tgattgtaac gaggattgtg gaacttctgg   8580
gacgcagggg gtgggaagcc ctcaaatatt ggtggaatct cctacagtat tggagtcagg   8640
aactaaagaa tagtgctgtt agcttgctca atgccacagc catagcagta gctgagggga   8700
cagatagggt tatagaagta gtacaaggag cttgtagagc tattcgccac atacctagaa   8760
gaataagaca gggcttggaa aggattttgc tataagatgg gtggcaagtg gtcaaaaagt   8820
agtgtgattg gatggcctac tgtaagggaa agaatgagac gagctgagcc agcagcagat   8880
```

```
agggtgggag cagcatctcg agacctggaa aaacatggag caatcacaag tagcaataca   8940

gcagctacca atgctgcttg tgcctggcta gaagcacaag aggaggagga ggtgggtttt   9000

ccagtcacac ctcaggtacc tttaagacca atgacttaca aggcagctgt agatcttagc   9060

cactttttaa aagaaaaggg gggactggaa gggctaattc actcccaaag aagacaagat   9120

atccttgatc tgtggatcta ccacacacaa ggctacttcc ctgattagca gaactacaca   9180

ccagggccag gggtcagata tccactgacc tttggatggt gctacaagct agtaccagtt   9240

gagccagata agatagaaga ggccaataaa ggagagaaca ccagcttgtt acaccctgtg   9300

agcctgcatg ggatggatga cccggagaga gaagtgttag agtggaggtt tgacagccgc   9360

ctagcatttc atcacgtggc ccgagagctg catccggagt acttcaagaa ctgctgacat   9420

cgagcttgct acaagggact ttccgctggg gactttccag ggaggcgtgg cctgggcggg   9480

actggggagt ggcgagccct cagatcctgc atataagcag ctgctttttg cctgtactgg   9540

gtctctctgg ttagaccaga tctgagcctg ggagctctct ggctaactag ggaacccact   9600

gcttaagcct caataaagct tgccttgagt gcttcaagta gtgtgtgccc gtctgttgtg   9660

tgactctggt aactagagat ccctcagacc cttttagtca gtgtggaaaa tctctagca    9719
```

<210> SEQ ID NO 5
<211> LENGTH: 3506
<212> TYPE: DNA
<213> ORGANISM: Human immunodeficiency virus
<220> FEATURE:
<221> NAME/KEY: MISC_FEATURE
<222> LOCATION: (1)..(650)
<223> OTHER INFORMATION: HXB2 Protease gene nt 1900 through 2549
<220> FEATURE:
<221> NAME/KEY: MISC_FEATURE
<222> LOCATION: (651)..(2336)
<223> OTHER INFORMATION: HXB2 RT gene nt 2550 through 4229
<220> FEATURE:
<221> NAME/KEY: MISC_FEATURE
<222> LOCATION: (2337)..(3506)
<223> OTHER INFORMATION: HXB2 INT gene nt 4230 through 5400

<400> SEQUENCE: 5

```
acaaattcag ctaccataat gatgcagaga ggcaatttta ggaaccaaag aaagattgtt     60

aagtgtttca attgtggcaa agaagggcac acagccagaa attgcagggc ccctaggaaa    120

aagggctgtt ggaaatgtgg aaaggaagga caccaaatga aagattgtac tgagagacag    180

gctaattttt tagggaagat ctggccttcc tacaagggaa ggccagggaa ttttcttcag    240

agcagaccag agccaacagc cccaccagaa gagagcttca ggtctggggt agagacaaca    300

actccccctc agaagcagga gccgatagac aaggaactgt atcctttaac ttccctcagg    360

tcactctttg gcaacgaccc ctcgtcacaa taaagatagg ggggcaacta aaggaagctc    420

taatataaac aggagcagat aatacaatat tagaagaaat gagtttgcca ggaagatgga    480

aaccaaaaat actagtggga gttggaggtt ttatgaaagt aagacagtat gatcagatac    540

tcatagaaat ctgtggacat aaagctatat ctacagtagt agtaggacct acacctgcca    600

acgtaattgg aagagatctg atgactcaga ttggttgcac tttaaatttt cccattagcc    660

ctattgagac tgtaccagta aaattaaagc caggaatgga tggcccaaaa gttaaacaat    720

ggccattgac agaagaaaaa ataaaagcat tagtagaaat ttgtacagag ttggaaaagg    780

aagggaaaat ttcaaaaatt gggcctgaaa atccatacaa tactccagta tttgccataa    840

agagaaaaaa cagttcttcc tccagatgga gaaaagtagt agatctcaga gaacttaata    900
```

-continued

```
agagaactca agacttctgg gaagttcaat taggaatacc acatcccgca gggatagaaa    960
agaacaaatc agcaacaata ctgtaagtgg gtgatgcatt ttattcagtt cccttagatg   1020
aagacttcag gaagtatact gcatttacca tacctagtat aaacaatgag acaccaggga   1080
ttagatatca gtacaatgtg cttccaatgg gatggaaagg atcaccagca atattccaaa   1140
gtagcatgac aaaaatctta gagcctttta gaaaacaaaa tccagacata gttatctgtc   1200
aatacgtgga tgatttgtta gtagcatctg acttagaaat agggcagcat agaacaaaaa   1260
tagaggagct gagacaacat ctgtggaggt ggggacttta cacaccagac caaaaacatc   1320
agaaagaaca tccattcctt tggctgggtt atgaactcca tcctgataaa tggacagtac   1380
agcctatagt gctgccagaa aaagacagct ggactgtcaa tgacatacag aagttagtgg   1440
ggaaattgaa ttgggcaagt cagatttacc cagggattaa agtaaggcaa ttatgtaaac   1500
tccttagagg aaccaaagca ctaacagaag taataccact aacagaagaa gcagagctag   1560
aactggcaga aaacagagag attctaaaag aaccagtaca tggagtgtat tatgacccat   1620
caaaagactt aatagcagaa atacagaagc aggggcaagg ccaatggaca tatcaaattt   1680
atcaagagcc atttaaaaat ctgaaaacag gaaaatatgc aagaatgagg ggtgcccaca   1740
ctaatgatgt aaaacaatta acagaggcag tgcaaaaaat aaccacagaa agcatagtaa   1800
tatggggaaa gactcctaaa tttaaactgc ccatacaaaa ggaaacatgg gaaacatggt   1860
ggacagagta ttggcaagcc acctggattc ctgagtggga gtttgttaat acccctccct   1920
tagtgaaatt atggtaccag ttagagaaag aacccatagt aggagcagaa accttctatg   1980
tagatggggc agctaacagg gagactaaat taggaaaagc aggatatgtt actaatagag   2040
gaagacaaaa agttgtcacc ctaactgaca caacaaatca gaagactgag ttacaagcaa   2100
tttatctagc tttgcaggat tcgggattag aagtaaacat agtaacagac tcacaatatg   2160
cattaggaat cattcaagca caaccagatc aaagtgaatc agagttagtc aatcaaataa   2220
tagagcagtt aataaaaaag gaaaaggtct atctggcatg ggtaccagca cacaaaggaa   2280
ttggaggaaa tgaacaagta gataaattag tcagtgctgg aatcaggaaa gtactatttt   2340
tagatggaat agataaggcc caagatgaac atgagaaata tcacagtaat tggagagcaa   2400
tggctagtga ttttaacctg ccacctgtag tagcaaaaga aatagtagcc agctgtgata   2460
aatgtcagct aaaaggagaa gccatgcatg gacaagtaga ctgtagtcca ggaatatggc   2520
aactagattg tatacattta gaaggaaaag ttatcatggt agcagttcat gtagccagtg   2580
gatatataga agcagaagtt attccagcac aaacagggca ggaagcagca tattttcttt   2640
taaaattagc aggaagatgg ccagtaaaaa caatacatac tgacaatggc agcaatttca   2700
ccggtgctac ggttagggcc gcctgttggt gggcgggaat caagcaggca ttttcaattc   2760
cccgcaatcc ccaaagtcac ggagtagtat aatctatgca taaagaatta aagaaaatta   2820
taggacaggt aagagatcag gctgaacatc ttaagacagc agtacaaatg gcagtattca   2880
tccacaattt taaaagaaaa ggggggattg gggggtacag tgcaggggaa agaatagtag   2940
acataatagc aacagacata caaactaaag aattacaaaa acaaattaca aaaattcaaa   3000
attttcgggt ttattacagg gacagcagaa atccactttg gaaaggacca gcaaagctcc   3060
tctggaaagg tgaaggggca gtagtaatac aagataatag tgacataaaa gtagtgccaa   3120
gaagaaaagc aaagatcatt agggattatg gaaaacagat ggcaggtgat gattgtgtgg   3180
caagtagaca ggatgaggat tagaacatgg aaaagtttag taaaacacca tatgtatgtt   3240
tcagggaaag ctaggggatg gttttataga catcactatg aaagccctca tccaagaata   3300
```

```
agttcagaag tacacatccc actaggggat gctagattgg taataacaac atattggggt   3360

ctgcatacag gagaaagaga ctggcatttg ggtcagggag tctccataga atggaggaaa   3420

aagagatata gcacacaagt agaccctgaa ctagcagacc aactaattca tctgtattac   3480

tttgactgtt tttcagactc tgctat                                        3506


<210> SEQ ID NO 6
<211> LENGTH: 3500
<212> TYPE: DNA
<213> ORGANISM: Human immunodeficiency virus
<220> FEATURE:
<221> NAME/KEY: MISC_FEATURE
<222> LOCATION: (1)..(650)
<223> OTHER INFORMATION: HXB2 Protease gene nt 1900 through 2549
<220> FEATURE:
<221> NAME/KEY: MISC_FEATURE
<222> LOCATION: (651)..(2330)
<223> OTHER INFORMATION: HXB2 RT gene nt 2550 through 4229
<220> FEATURE:
<221> NAME/KEY: MISC_FEATURE
<222> LOCATION: (2331)..(3500)
<223> OTHER INFORMATION: HXB2 INT gene nt 4230 through 5400

<400> SEQUENCE: 6

acaaattcag ctaccataat gatgcagaga ggcaatttta ggaaccaaag aaagattgtt     60

aagtgtttca attgtggcaa agaagggcac acagccagaa attgcagggc ccctaggaaa    120

aagggctgtt ggaaatgtgg aaaggaagga caccaaatga aagattgtac tgagagacag    180

gctaattttt tagggaagat ctggccttcc tacaagggaa ggccagggaa ttttcttcag    240

agcagaccag agccaacagc cccaccagaa gagagcttca ggtctggggt agagacaaca    300

actccccctc agaagcagga gccgatagac aaggaactgt atcctttaac ttccctcagg    360

tcactctttg gcaacgaccc ctcgtcacaa taaagatagg ggggcaacta aaggaagctc    420

tattataaac aggagcagat gatacagtat tagaagaaat gagtttgcca ggaagatgga    480

aaccaaaaat gataggggga attggaggtt ttatcaaagt aagacagtat gatcagatac    540

tcatagaaat ctgtggacat aaagctatag gtacagtatt agtaggacct acacctgtca    600

acataattgg aagaaatctg ttgactcaga ttggttgcac tttaaatttt cccattagcc    660

ctattgagac tgtaccagta aaattaaagc caggaatgga tggcccaaaa gttaaacaat    720

ggccattgac agaagaaaaa ataaaagcat tagtagaaat ttgtacagag atggaaaagg    780

aagggaaaat ttcaaaaatt gggcctgaaa atccatacaa tactccagta tttgccataa    840

agaaaaaaga cagtactaaa tggagaaaat tagtagattt cagagaactt aataagagaa    900

ctcaagactt ctgggaagtt caattaggaa taccacatcc cgcagggtta aaaaagaaaa    960

aatcagtaac agtactgtaa gtgggtgatg catatttttc agttccctta gatgaagact   1020

tcaggaagta tactgcattt accataccta gtataaacaa tgagacacca gggattagat   1080

atcagtacaa tgtgcttcca cagggatgga aaggatcacc agcaatattc caaagtagca   1140

tgacaaaaat cttagagcct tttagaaaac aaaatccaga catagttatc tatcaataca   1200

tggatgattt gtatgtagga tctgacttag aaatagggca gcatagaaca aaaatagagg   1260

agctgagaca acatctgttg aggtggggac ttaccacacc agacaaaaaa catcagaaag   1320

aacctccatt cctttggatg ggttatgaac tccatcctga taaatggaca gtacagccta   1380

tagtgctgcc agaaaaagac agctggactg tcaatgacat acagaagtta gtggggaaat   1440

tgaattgggc aagtcagatt tacccaggga ttaaagtaag gcaattatgt aaactcctta   1500
```

```
gaggaaccaa agcactaaca gaagtaatac cactaacaga agaagcagag ctagaactgg   1560
cagaaaacag agagattcta aaagaaccag tacatggagt gtattatgac ccatcaaaag   1620
acttaatagc agaaatacag aagcaggggc aaggccaatg gacatatcaa atttatcaag   1680
agccatttaa aaatctgaaa acaggaaaat atgcaagaat gaggggtgcc cacactaatg   1740
atgtaaaaca attaacagag gcagtgcaaa aaataaccac agaaagcata gtaatatggg   1800
gaaagactcc taaatttaaa ctgcccatac aaaaggaaac atgggaaaca tggtggacag   1860
agtattggca agccacctgg attcctgagt gggagtttgt taatacccct cccttagtga   1920
aattatggta ccagttagag aaagaaccca tagtaggagc agaaaccttc tatgtagatg   1980
gggcagctaa cagggagact aaattaggaa aagcaggata tgttactaat agaggaagac   2040
aaaaagttgt caccctaact gacacaacaa atcagaagac tgagttacaa gcaatttatc   2100
tagctttgca ggattcggga ttagaagtaa acatagtaac agactcacaa tatgcattag   2160
gaatcattca agcacaacca gatcaaagtg aatcagagtt agtcaatcaa ataatagagc   2220
agttaataaa aaaggaaaag gtctatctgg catgggtacc agcacacaaa ggaattggag   2280
gaaatgaaca agtagataaa ttagtcagtg ctggaatcag gaaagtacta tttttagatg   2340
gaatagataa ggcccaagat gaacatgaga aatatcacag taattggaga gcaatggcta   2400
gtgattttaa cctgccacct gtagtagcaa aagaaatagt agccagctgt gataaatgtc   2460
agctaaaagg agaagccatg catggacaag tagactgtag tccaggaata tggcaactag   2520
attgtacaca tttagaagga aaagttatcc tggtagcagt tcatgtagcc agtggatata   2580
tagaagcaga agttattcca gcagaaacag ggcaggaaac agcatatttt cttttaaaat   2640
tagcaggaag atggccagta aaaacaatac atactgacaa tggcagcaat ttcaccggtg   2700
ctacggttag ggccgcctgt tggtgggcgg gaatcaagca ggaatttgga attccctaca   2760
atccccaaag tcaaggagta gtataatcta tgaataaaga attaaagaaa attataggac   2820
aggtaagaga tcaggctgaa catcttaaga cagcagtaca aatggcagta ttcatccaca   2880
attttaaaag aaaagggggg attggggggt acagtgcagg ggaaagaata gtagacataa   2940
tagcaacaga catacaaact aaagaattac aaaaacaaat tacaaaaatt caaaattttc   3000
gggtttatta cagggacagc agaaatccac tttggaaagg accagcaaag ctcctctgga   3060
aaggtgaagg ggcagtagta atacaagata atagtgacat aaaagtagtg ccaagaagaa   3120
aagcaaagat cattagggat tatggaaaac agatggcagg tgatgattgt gtggcaagta   3180
gacaggatga ggattagaac atggaaaagt ttagtaaaac accatatgta tgtttcaggg   3240
aaagctaggg gatggtttta tagacatcac tatgaaagcc ctcatccaag aataagttca   3300
gaagtacaca tcccactagg ggatgctaga ttggtaataa caacatattg gggtctgcat   3360
acaggagaaa gagactggca tttgggtcag ggagtctcca tagaatggag gaaaaagaga   3420
tatagcacac aagtagaccc tgaactagca gaccaactaa ttcatctgta ttactttgac   3480
tgtttttcag actctgctat                                               3500
```

<210> SEQ ID NO 7
<211> LENGTH: 1526
<212> TYPE: DNA
<213> ORGANISM: Human immunodeficiency virus

<400> SEQUENCE: 7

```
atgatctgta gtgctacaga aaaattgtgg gtcacagtct attatggggt acctgtgtgg     60
aaggaagcaa ccaccactct attttgtgca tcagatgcta aagcatatga tacagaggta    120
```

```
cataatgttt gggccacaca tgcctgtgta cccacagacc ccaacccaca agaagtagta    180
ttggtaaatg tgacagaaaa ttttaacatg tggaaaaatg acatggtaga acagatgcat    240
gaggatataa tcagtttatg ggatcaaagc ctaaagccat gtgtaaaatt aaccccactc    300
tgtgttagtt taaagtgcac tgatttgaag aatgatacta ataccaatag tagtagcggg    360
agaatgataa tggagaaagg agagataaaa aactgctctt tcaatatcag cacaagcata    420
agaggtaagg tgcagaaaga atatgcattt ttttataaac ttgatataat accaatagat    480
aatgatacta ccagctataa gttgacaagt tgtaacacct cagtcattac acaggcctgt    540
ccaaaggtat cctttgagcc aattcccata cattattgtg ccccggctgg ttttgcgatt    600
ctaaaatgta ataataagac gttcaatgga acaggaccat gtacaaatgt cagcacagta    660
caatgtacac atggaattag gccagtagta tcaactcaac tgctgttaaa tggcagtcta    720
gcagaagaag aggtagtaat tagatctgtc aatttcacgg acaatgctaa aaccataata    780
gtacagctga acacatctgt agaaattaat tgtacaagac ccaacaacaa tacaagaaaa    840
agaatccgta tccagagagg accagggaga gcatttgtta caataggaaa aataggaaat    900
atgagacaag cacattgtaa cattagtaga gcaaaatgga ataacacttt aaaacagata    960
gctagcaaat taagagaaca atttggaaat aataaaacaa taatctttaa gcaatcctca   1020
ggaggggacc cagaaattgt aacgcacagt tttaattgtg gaggggaatt tttctactgt   1080
aattcaacac aactgtttaa tagtacttgg tttaatagta cttggagtac tgaagggtca   1140
aataacactg aaggaagtga cacaatcacc ctcccatgca gaataaaaca aattataaac   1200
atgtggcaga aagtaggaaa agcaatgtat gcccctccca tcagtggaca aattagatgt   1260
tcatcaaata ttacagggct gctattaaca agagatggtg gtaatagcaa caatgagtcc   1320
gagatcttca gacctggagg aggagatatg agggacaatt ggagaagtga attatataaa   1380
tataaagtag taaaaattga accattagga gtagcaccca ccaaggcaaa gagaagagtg   1440
gtgcagagag aaaaaagagc agtgggaata ggagctttgt tccttgggtt cttgggagca   1500
gcaggaagca ctatgggcgc agcctc                                        1526
```

<210> SEQ ID NO 8
<211> LENGTH: 1520
<212> TYPE: DNA
<213> ORGANISM: Human immunodeficiency virus

<400> SEQUENCE: 8

```
atgatctgta gtgctacaga aaaattgtgg gtcacagtct attatggggt acctgtgtgg     60
aaagaagcaa ccaccactct attttgtgca tcagatgcta aagcatatga tacagaggta    120
cataatgttt gggccacaca tgcctgtgta cccacagacc ccaacccaca agaagtagaa    180
ttggaaaatg tgacagaaaa ttttaacatg tggaaaaata acatggtaga acagatgcat    240
gaggatataa tcagtttatg ggatcaaagc ctaaagccat gtgtaaaatt aactccactc    300
tgtgttactt taaattgcac tgatttgagg aatgctacta atgggaatga cactaatacc    360
actagtagta gcagggaaat gatgggggga ggagaaatga aaaattgctc tttcaaaatc    420
accacaaaca taagaggtaa ggtgcagaaa gaatatgcac tttttataa acttgatata     480
gtaccaatag ataataatag taataataga tataggttga taagttgtaa cacctcagtc    540
attacacagg cctgtccaaa gatatccttt gagccaattc ccatacatta ttgtgccccg    600
gctggttttg cgattctaaa gtgtaaagat aagaagttca atggaaaagg accatgttca    660
```

```
aatgtcagca cagtacaatg tacacatggg attaggccag tagtatcaac tcaactgctg    720

ttaaatggca gtctagcaga agaagaggta gtaattagat ccgaaaattt cgcggacaat    780

gctaaaacca taatagtaca gctgaatgaa tctgtagaaa ttaattgtac aagacccaac    840

aacaatacaa gaaaaagtat acatatagga ccaggcagag cattatatac aacaggaaaa    900

ataataggag atataagaca agcacattgt aaccttagta gagcaaaatg gaatgacact    960

ttaaataaaa tagttataaa attaagagaa caatttggga ataaaacaat agtctttaag   1020

cattcctcag gaggggaccc agaaattgtg acgcacagtt ttaattgtgg aggggaattt   1080

ttctactgta attcaacaca actgtttaat agtacttgga atgttactga agagtcaaat   1140

aacactgtag aaaataacac aatcacactc ccatgcagaa taaaacaaat tataaacatg   1200

tggcagaaag taggaagagc aatgtatgcc cctcccatca gaggacaaat tagatgttca   1260

tcaaatatta cagggctgct attaacaaga gatggtggtc cagaggacaa caagaccgag   1320

gtcttcagac ctggaggagg agatatgagg gacaattgga gaagtgaatt atataaatat   1380

aaagtagtaa aaattgaacc attaggagta gcacccacca aggcaaagag aagagtggtg   1440

cagagagaaa aaagagcagt gggaatagga gctgtgttcc ttgggttctt gggagcagca   1500

ggaagcacta tgggcgcagc                                                1520
```

```
<210> SEQ ID NO 9
<211> LENGTH: 10080
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: MISC_FEATURE
<222> LOCATION: (1)..(7652)
<223> OTHER INFORMATION: Sindbis gene sequence
<220> FEATURE:
<221> NAME/KEY: MISC_FEATURE
<222> LOCATION: (7653)..(9707)
<223> OTHER INFORMATION: Ebola GP insert sequence
<220> FEATURE:
<221> NAME/KEY: MISC_FEATURE
<222> LOCATION: (9708)..(10080)
<223> OTHER INFORMATION: Sindbis gene sequence

<400> SEQUENCE: 9
```

```
attgacggcg tagtacacac tattgaatca aacagccgac caattgcact accatcacaa     60

tggagaagcc agtagtaaac gtagacgtag acccccagag tccgtttgtc gtgcaactgc    120

aaaaaagctt cccgcaattt gaggtagtag cacagcaggt cactccaaat gaccatgcta    180

atgccagagc attttcgcat ctggccagta aactaatcga gctggaggtt cctaccacag    240

cgacgatctt ggacataggc agcgcaccgg ctcgtagaat gttttccgag caccagtatc    300

attgtgtctg ccccatgcgt agtccagaag acccggaccg catgatgaaa tacgccagta    360

aactggcgga aaaagcgtgc aagattacaa acaagaactt gcatgagaag attaaggatc    420

tccggaccgt acttgatacg ccggatgctg aaacaccatc gctctgcttt cacaacgatg    480

ttacctgcaa catgcgtgcc gaatattccg tcatgcagga cgtgtatatc aacgctcccg    540

gaactatcta tcatcaggct atgaaaggcg tgcggaccct gtactggatt ggcttcgaca    600

ccacccagtt catgttctcg gctatggcag gttcgtaccc tgcgtacaac accaactggg    660

ccgacgagaa agtccttgaa gcgcgtaaca tcggactttg cagcacaaag ctgagtgaag    720

gtaggacagg aaaattgtcg ataatgagga agaaggagtt gaagcccggg tcgcgggttt    780
```

```
atttctccgt aggatcgaca ctttatccag aacacagagc cagcttgcag agctggcatc    840
ttccatcggt gttccacttg aatggaaagc agtcgtacac ttgccgctgt gatacagtgg    900
tgagttgcga aggctacgta gtgaagaaaa tcaccatcag tcccgggatc acgggagaaa    960
ccgtgggata cgcggttaca cacaatagcg agggcttctt gctatgcaaa gttactgaca   1020
cagtaaaagg agaacgggta tcgttccctg tgtgcacgta catcccggcc accatatgcg   1080
atcagatgac tggtataatg gccacggata tatcacctga cgatgcacaa aaacttctgg   1140
ttgggctcaa ccagcgaatt gtcattaacg gtaggactaa caggaacacc aacaccatgc   1200
aaaattacct tctgccgatc atagcacaag ggttcagcaa atgggctaag gagcgcaagg   1260
atgatcttga taacgagaaa atgctgggta ctagagaacg caagcttacg tatggctgct   1320
tgtgggcgtt tcgcactaag aaagtacatt cgttttatcg cccacctgga acgcagacct   1380
gcgtaaaagt cccagcctct tttagcgctt ttcccatgtc gtccgtatgg acgacctctt   1440
tgcccatgtc gctgaggcag aaattgaaac tggcattgca accaaagaag gaggaaaaac   1500
tgctgcaggt ctcggaggaa ttagtcatgg aggccaaggc tgcttttgag gatgctcagg   1560
aggaagccag agcggagaag ctccgagaag cacttccacc attagtggca gacaaaggca   1620
tcgaggcagc cgcagaagtt gtctgcgaag tggaggggct ccaggcggac atcggagcag   1680
cattagttga aaccccgcgc ggtcacgtaa ggataatacc tcaagcaaat gaccgtatga   1740
tcggacagta tatcgttgtc tcgccaaact ctgtgctgaa gaatgccaaa ctcgcaccag   1800
cgcacccgct agcagatcag gttaagatca taacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga aagaaaattg tcgcgaaatt gaggccgacg   2340
tgctaagact gaggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
ccatgcaatg cggattcttc aacatgatgc aactaaaggt acatttcaat caccctgaaa   2580
aagacatatg caccaagaca ttctacaagt atatctcccg gcgttgcaca cagccagtta   2640
cagctattgt atcgacactg cattacgatg gaaagatgaa aaccacgaac ccgtgcaaga   2700
agaacattga aatcgatatt acaggggcca caaagccgaa gccaggggat atcatcctga   2760
catgtttccg cgggtgggtt aagcaattgc aaatcgacta tcccggacat gaagtaatga   2820
cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag cccactaaca   3000
tacctaaagg aaactttcag gctactatag aggactggga agctgaacac aagggaataa   3060
ttgctgcaat aaacagcccc actccccgtg ccaatccgtt cagctgcaag accaacgttt   3120
gctgggcgaa agcattggaa ccgatactag ccacggccgg tatcgtactt accggttgcc   3180
```

```
agtggagcga actgttccca cagtttgcgg atgacaaacc acattcggcc atttacgcct   3240
tagacgtaat ttgcattaag tttttcggca tggacttgac aagcggactg ttttctaaac   3300
agagcatccc actaacgtac catcccgccg attcagcgag gccggtagct cattgggaca   3360
acagcccagg aacccgcaag tatgggtacg atcacgccat tgccgccgaa ctctcccgta   3420
gatttccggt gttccagcta gctgggaagg gcacacaact tgatttgcag acggggagaa   3480
ccagagttat ctctgcacag cataacctgg tcccggtgaa ccgcaatctt cctcacgcct   3540
tagtccccga gtacaaggag aagcaacccg gcccggtcaa aaaattcttg aaccagttca   3600
aacaccactc agtacttgtg gtatcagagg aaaaaattga agctccccgt aagagaatcg   3660
aatggatcgc cccgattggc atagccggtg cagataagaa ctacaacctg gctttcgggt   3720
ttccgccgca ggcacggtac gacctggtgt tcatcaacat tggaactaaa tacagaaacc   3780
accactttca gcagtgcgaa gaccatgcgg cgaccttaaa aaccctttcg cgttcggccc   3840
tgaattgcct taacccagga ggcaccctcg tggtgaagtc ctatggctac gccgaccgca   3900
acagtgagga cgtagtcacc gctcttgcca gaaagtttgt cagggtgtct gcagcgagac   3960
cagattgtgt ctcaagcaat acagaaatgt acctgatttt ccgacaacta gacaacagcc   4020
gtacacggca attcaccccg caccatctga attgcgtgat ttcgtccgtg tatgagggta   4080
caagagatgg agttggagcc gcgccgtcat accgcaccaa aagggagaat attgctgact   4140
gtcaagagga agcagttgtc aacgcagcca atccgctggg tagaccaggc gaaggagtct   4200
gccgtgccat ctataaacgt tggccgacca gttttaccga ttcagccacg gagacaggca   4260
ccgcaagaat gactgtgtgc ctaggaaaga aagtgatcca cgcggtcggc cctgatttcc   4320
ggaagcaccc agaagcagaa gccttgaaat tgctacaaaa cgcctaccat gcagtggcag   4380
acttagtaaa tgaacataac atcaagtctg tcgccattcc actgctatct acaggcattt   4440
acgcagccgg aaaagaccgc cttgaagtat cacttaactg cttgacaacc gcgctagaca   4500
gaactgacgc ggacgtaacc atctattgcc tggataagaa gtggaaggaa agaatcgacg   4560
cggcactcca acttaaggag tctgtaacag agctgaagga tgaagatatg gagatcgacg   4620
atgagttagt atggattcat ccagacagtt gcttgaaggg aagaaaggga ttcagtacta   4680
caaaaggaaa attgtattcg tacttcgaag gcaccaaatt ccatcaagca gcaaaagaca   4740
tggcggagat aaaggtcctg ttccctaatg accaggaaag taatgaacaa ctgtgtgcct   4800
acatattggg tgagaccatg gaagcaatcc gcgaaaagtg cccggtcgac cataacccgt   4860
cgtctagccc gcccaaaacg ttgccgtgcc tttgcatgta tgccatgacg ccagaaaggg   4920
tccacagact tagaagcaat aacgtcaaag aagttacagt atgctcctcc acccccccttc   4980
ctaagcacaa aattaagaat gttcagaagg ttcagtgcac gaaagtagtc ctgtttaatc   5040
cgcacactcc cgcattcgtt cccgcccgta agtacataga agtgccagaa cagcctaccg   5100
ctcctcctgc acaggccgag gaggcccccg aagttgtagc gacaccgtca ccatctacag   5160
ctgataacac ctcgcttgat gtcacagaca tctcactgga tatggatgac agtagcgaag   5220
gctcactttt ttcgagcttt agcggatcgg acaactctat tactagtatg gacagttggt   5280
cgtcaggacc tagttcacta gagatagtag accgaaggca ggtggtggtg gctgacgttc   5340
atgccgtcca agagcctgcc cctattccac cgccaaggct aaagaagatg gcccgcctgg   5400
cagcggcaag aaaagagccc actccaccgg caagcaatag ctctgagtcc ctccacctct   5460
cttttggtgg ggtatccatg tccctcggat caattttcga cggagagacg gcccgccagg   5520
```

```
cagcggtaca accccctggca acaggcccca cggatgtgcc tatgtctttc ggatcgtttt   5580
ccgacggaga gattgatgag ctgagccgca gagtaactga gtccgaaccc gtcctgtttg   5640
gatcatttga accgggcgaa gtgaactcaa ttatatcgtc ccgatcagcc gtatcttttc   5700
cactacgcaa gcagagacgt agacgcagga gcaggaggac tgaatactga ctaaccgggg   5760
taggtgggta catattttcg acggacacag gccctgggca cttgcaaaag aagtccgttc   5820
tgcagaacca gcttacagaa ccgaccttgg agcgcaatgt cctggaaaga attcatgccc   5880
cggtgctcga cacgtcgaaa gaggaacaac tcaaactcag gtaccagatg atgcccaccg   5940
aagccaacaa aagtaggtac cagtctcgta aagtagaaaa tcagaaagcc ataaccactg   6000
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact tggatatggt agacgggaca gtcgcctgcc   6240
tggatactgc aaccttctgc cccgctaagc ttagaagtta cccgaaaaaa catgagtata   6300
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgac attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
aagaagtgcc tatggataga ttcgtcatgg acatgaaaag agacgtgaaa gttacaccag   6660
gcacgaaaca cacagaagaa agaccgaaag tacaagtgat acaagccgca gaacccctgg   6720
cgactgctta cttatgcggg attcaccggg aattagtgcg taggcttacg gccgtcttgc   6780
ttccaaacat tcacacgctt tttgacatgt cggcggagga ttttgatgca atcatagcag   6840
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga aatccggaat gttcctcaca ctttttgtca   7080
acacagtttt gaatgtcgtt atcgccagca gagtactaga agagcggctt aaaacgtcca   7140
gatgtgcagc gttcattggc gacgacaaca tcatacatgg agtagtatct gacaaagaaa   7200
tggctgagag gtgcgccacc tggctcaaca tggaggttaa gatcatcgac gcagtcatcg   7260
gtgagagacc accttacttc tgcggcggat ttatcttgca agattcggtt acttccacag   7320
cgtgccgcgt ggcggatccc ctgaaaaggc tgtttaagtt gggtaaaccg ctcccagccg   7380
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt ttgcccagag caaaagagca ttccaagcca   7560
tcagagggga aataaagcat ctctacggtg gtcctaaata gtcagcatag tacatttcat   7620
ctgactaata ctacaacacc accacctcta gatctagaag gaatattgca gttacctcgt   7680
gatcgattca agaggacatc attctttctt tgggtaatta tcctttttcca aagaacattt   7740
tccatcccgc ttggagttat ccacaatagt acattacagg ttagtgatgt cgacaaacta   7800
gtttgtcgtg acaaactgtc atccacaaat caattgagat cagttggact gaatctcgag   7860
gggaatggag tggcaactga cgtgccatct gcgactaaaa gatggggctt caggtccggt   7920
```

```
gtcccaccaa aggtggtcaa ttatgaagct ggtgaatggg ctgaaaactg ctacaatctt   7980
gaaatcaaaa aacctgacgg gagtgagtgt ctaccagcag cgccagacgg gattcggggc   8040
ttcccccggt gccggtatgt gcacaaagta tcaggaacgg gaccatgtgc cggagacttt   8100
gccttccaca aagagggtgc tttcttcctg tatgatcgac ttgcttccac agttatctac   8160
cgaggaacga ctttcgctga aggtgtcgtt gcatttctga tactgcccca agctaagaag   8220
gacttcttca gctcacaccc cttgagagag ccggtcaatg caacggagga cccgtcgagt   8280
ggctattatt ctaccacaat tagatatcag gctaccggtt ttggaactaa tgagacagag   8340
tacttgttcg aggttgacaa tttgacctac gtccaacttg aatcaagatt cacaccacag   8400
tttctgctcc agctgaatga gacaatatat gcaagtggga agaggagcaa caccacggga   8460
aaactaattt ggaaggtcaa ccccgaaatt gatacaacaa tcggggagtg ggccttcagg   8520
gaaactaaaa aaacctcact agaaaaattc gcagtgaaga gttgtctttc acagctgtat   8580
caaacggacc caaaaacatc agtggtcaga gtccggcgcg aacttcttcc gacccagaga   8640
ccaacacaac aaatgaagac cacaaaatca tggcttcaga aaattcctct gcaatggttc   8700
aagtgcacag tcaaggaagg aaagctgcag tgtcgcatct gacaaccctt gccacaatct   8760
ccacgagtcc tcaacctccc acaaccaaaa caggtccgga caacagcacc cataatacac   8820
ccgtgtataa acttgacatc tctgaggcaa ctcaagttgg acaacatcac cgtagagcag   8880
acaacgacag cacagcctcc gacactcccc ccgccacgac cgcagccgga cccttaaaag   8940
cagagaacac caacacgagt aagagcgctg actccctgga cctcgccacc acgataagcc   9000
cccaaaacta cagcgagact gctggcaaca acaacactca tcaccaagat accggagaag   9060
agagtgccag cagcgggaag ctaggcttaa ttaccaatac tattgctgga gtagcaggac   9120
tgatcacagg cgggagaagg actcgaagag aagtaattgt caatgctcaa cccaaatgca   9180
accccaattt acattactgg actactcagg atgaaggtgc tgcaatcgga ttggcctgga   9240
taccatattt cgggccagca gccgaaggaa tttacacaga ggggctaatg cacaaccaag   9300
atggtttaat ctgtgggttg aggcagctgg ccaacgaaac gactcaagct ctccaactgt   9360
tcctgagagc cacaactgag ctgcgaacct tttcaatcct caaccgtaag gcaattgact   9420
tcctgctgca gcgatggggt ggcacatgcc acattttggg accggactgc tgtatcgaac   9480
cacatgattg gaccaagaac ataacagaca aaattgatca gattattcat gattttgttg   9540
ataaaaccct tccggaccag gggacaatg acaattggtg gacaggatgg agacaatgga   9600
taccggcaat ttaaatatcg agggcaggag cgagagggcc aaggccaggg agggcggcca   9660
ccaccatcac caccatcacc attagtaatg aggtaaccgt ggggcccaat gatccgacca   9720
gcaaaactcg atgtacttcc gaggaactga tgtgcataat gcatcaggct ggtacattag   9780
atccccgctt accgcgggca atatagcaac actaaaaact cgatgtactt ccgaggaagc   9840
gcagtgcata atgctgcgca gtgttgccac ataaccacta tattaaccat ttatctagcg   9900
gacgccaaaa actcaatgta tttctgagga agcgtggtgc ataatgccac gcagcgtctg   9960
cataactttt attatttctt ttattaatca acaaaatttt gtttttaaca tttcaaaaaa  10020
aaaaaaaaaa aaaaaaaaaa aaaaaaaaaa agggaattcc tcgattaatt aagcggccgc  10080
```

<210> SEQ ID NO 10
<211> LENGTH: 10348
<212> TYPE: DNA
<213> ORGANISM: Artificial Sequence
<220> FEATURE:

<223> OTHER INFORMATION: Description of Artificial Sequence: Synthetic polynucleotide
<220> FEATURE:
<221> NAME/KEY: MISC_FEATURE
<222> LOCATION: (1)..(7652)
<223> OTHER INFORMATION: Sindbis gene sequence
<220> FEATURE:
<221> NAME/KEY: MISC_FEATURE
<222> LOCATION: (7653)..(9975)
<223> OTHER INFORMATION: Ebola NP/VP24 insert sequence
<220> FEATURE:
<221> NAME/KEY: MISC_FEATURE
<222> LOCATION: (9976)..(10348)
<223> OTHER INFORMATION: Sindbis gene sequence

<400> SEQUENCE: 10

```
attgacggcg tagtacacac tattgaatca aacagccgac caattgcact accatcacaa     60

tggagaagcc agtagtaaac gtagacgtag acccccagag tccgtttgtc gtgcaactgc    120

aaaaaagctt cccgcaattt gaggtagtag cacagcaggt cactccaaat gaccatgcta    180

atgccagagc attttcgcat ctggccagta aactaatcga gctggaggtt cctaccacag    240

cgacgatctt ggacataggc agcgcaccgg ctcgtagaat gttttccgag caccagtatc    300

attgtgtctg ccccatgcgt agtccagaag acccggaccg catgatgaaa tacgccagta    360

aactggcgga aaaagcgtgc aagattacaa acaagaactt gcatgagaag attaaggatc    420

tccggaccgt acttgatacg ccggatgctg aaacaccatc gctctgcttt cacaacgatg    480

ttacctgcaa catgcgtgcc gaatattccg tcatgcagga cgtgtatatc aacgctcccg    540

gaactatcta tcatcaggct atgaaaggcg tgcggaccct gtactggatt ggcttcgaca    600

ccacccagtt catgttctcg gctatggcag gttcgtaccc tgcgtacaac accaactggg    660

ccgacgagaa agtccttgaa gcgcgtaaca tcggactttg cagcacaaag ctgagtgaag    720

gtaggacagg aaaattgtcg ataatgagga agaaggagtt gaagcccggg tcgcgggttt    780

atttctccgt aggatcgaca ctttatccag aacacagagc cagcttgcag agctggcatc    840

ttccatcggt gttccacttg aatggaaagc agtcgtacac ttgccgctgt gatacagtgg    900

tgagttgcga aggctacgta gtgaagaaaa tcaccatcag tcccgggatc acgggagaaa    960

ccgtgggata cgcggttaca cacaatagcg agggcttctt gctatgcaaa gttactgaca   1020

cagtaaaagg agaacgggta tcgttccctg tgtgcacgta catcccggcc accatatgcg   1080

atcagatgac tggtataatg gccacggata tatcacctga cgatgcacaa aaacttctgg   1140

ttgggctcaa ccagcgaatt gtcattaacg gtaggactaa caggaacacc aacaccatgc   1200

aaaattacct tctgccgatc atagcacaag ggttcagcaa atgggctaag gagcgcaagg   1260

atgatcttga taacgagaaa atgctgggta ctagagaacg caagcttacg tatggctgct   1320

tgtgggcgtt tcgcactaag aaagtacatt cgttttatcg cccacctgga acgcagacct   1380

gcgtaaaagt cccagcctct tttagcgctt ttcccatgtc gtccgtatgg acgacctctt   1440

tgcccatgtc gctgaggcag aaattgaaac tggcattgca accaaagaag gaggaaaaac   1500

tgctgcaggt ctcggaggaa ttagtcatgg aggccaaggc tgcttttgag gatgctcagg   1560

aggaagccag agcggagaag ctccgagaag cacttccacc attagtggca gacaaaggca   1620

tcgaggcagc cgcagaagtt gtctgcgaag tggaggggct ccaggcggac atcggagcag   1680

cattagttga aacccccgcgc ggtcacgtaa ggataatacc tcaagcaaat gaccgtatga   1740

tcggacagta tatcgttgtc tcgccaaact ctgtgctgaa gaatgccaaa ctcgcaccag   1800

cgcacccgct agcagatcag gttaagatca taacacactc cggaagatca ggaaggtacg   1860
```

-continued

```
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga aagaaaattg tcgcgaaatt gaggccgacg   2340
tgctaagact gaggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
ccatgcaatg cggattcttc aacatgatgc aactaaaggt acatttcaat caccctgaaa   2580
aagacatatg caccaagaca ttctacaagt atatctcccg gcgttgcaca cagccagtta   2640
cagctattgt atcgacactg cattacgatg gaaagatgaa aaccacgaac ccgtgcaaga   2700
agaacattga aatcgatatt acaggggcca caaagccgaa gccaggggat atcatcctga   2760
catgtttccg cgggtgggtt aagcaattgc aaatcgacta tcccggacat gaagtaatga   2820
cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag cccactaaca   3000
tacctaaagg aaactttcag gctactatag aggactggga agctgaacac aagggaataa   3060
ttgctgcaat aaacagcccc actccccgtg ccaatccgtt cagctgcaag accaacgttt   3120
gctgggcgaa agcattggaa ccgatactag ccacggccgg tatcgtactt accggttgcc   3180
agtggagcga actgttccca cagtttgcgg atgacaaacc acattcggcc atttacgcct   3240
tagacgtaat ttgcattaag tttttcggca tggacttgac aagcggactg ttttctaaac   3300
agagcatccc actaacgtac catcccgccg attcagcgag gccggtagct cattgggaca   3360
acagcccagg aacccgcaag tatgggtacg atcacgccat tgccgccgaa ctctcccgta   3420
gatttccggt gttccagcta gctgggaagg gcacacaact tgatttgcag acggggagaa   3480
ccagagttat ctctgcacag cataacctgg tcccggtgaa ccgcaatctt cctcacgcct   3540
tagtccccga gtacaaggag aagcaacccg gcccggtcaa aaaattcttg aaccagttca   3600
aacaccactc agtacttgtg gtatcagagg aaaaaattga agctccccgt aagagaatcg   3660
aatggatcgc cccgattggc atagccggtg cagataagaa ctacaacctg gctttcgggt   3720
ttccgccgca ggcacggtac gacctggtgt tcatcaacat tggaactaaa tacagaaacc   3780
accactttca gcagtgcgaa gaccatgcgg cgaccttaaa aaccctttcg cgttcggccc   3840
tgaattgcct taacccagga ggcaccctcg tggtgaagtc ctatggctac gccgaccgca   3900
acagtgagga cgtagtcacc gctcttgcca gaaagtttgt cagggtgtct gcagcgagac   3960
cagattgtgt ctcaagcaat acagaaatgt acctgatttt ccgacaacta gacaacagcc   4020
gtacacggca attcaccccg caccatctga attgcgtgat ttcgtccgtg tatgagggta   4080
caagagatgg agttggagcc gcgccgtcat accgcaccaa aagggagaat attgctgact   4140
gtcaagagga agcagttgtc aacgcagcca atccgctggg tagaccaggc gaaggagtct   4200
gccgtgccat ctataaacgt tggccgacca gttttaccga ttcagccacg gagacaggca   4260
```

```
ccgcaagaat gactgtgtgc ctaggaaaga aagtgatcca cgcggtcggc cctgatttcc   4320
ggaagcaccc agaagcagaa gccttgaaat tgctacaaaa cgcctaccat gcagtggcag   4380
acttagtaaa tgaacataac atcaagtctg tcgccattcc actgctatct acaggcattt   4440
acgcagccgg aaaagaccgc cttgaagtat cacttaactg cttgacaacc gcgctagaca   4500
gaactgacgc ggacgtaacc atctattgcc tggataagaa gtggaaggaa agaatcgacg   4560
cggcactcca acttaaggag tctgtaacag agctgaagga tgaagatatg gagatcgacg   4620
atgagttagt atggattcat ccagacagtt gcttgaaggg aagaaaggga ttcagtacta   4680
caaaaggaaa attgtattcg tacttcgaag gcaccaaatt ccatcaagca gcaaaagaca   4740
tggcggagat aaaggtcctg ttccctaatg accaggaaag taatgaacaa ctgtgtgcct   4800
acatattggg tgagaccatg gaagcaatcc gcgaaaagtg cccggtcgac cataacccgt   4860
cgtctagccc gcccaaaacg ttgccgtgcc tttgcatgta tgccatgacg ccagaaaggg   4920
tccacagact tagaagcaat aacgtcaaag aagttacagt atgctcctcc acccccccttc  4980
ctaagcacaa aattaagaat gttcagaagg ttcagtgcac gaaagtagtc ctgtttaatc   5040
cgcacactcc cgcattcgtt cccgcccgta agtacataga agtgccagaa cagcctaccg   5100
ctcctcctgc acaggccgag gaggcccccg aagttgtagc gacaccgtca ccatctacag   5160
ctgataacac ctcgcttgat gtcacagaca tctcactgga tatggatgac agtagcgaag   5220
gctcactttt ttcgagcttt agcggatcgg acaactctat tactagtatg gacagttggt   5280
cgtcaggacc tagttcacta gagatagtag accgaaggca ggtggtggtg gctgacgttc   5340
atgccgtcca agagcctgcc cctattccac cgccaaggct aaagaagatg gcccgcctgg   5400
cagcggcaag aaaagagccc actccaccgg caagcaatag ctctgagtcc ctccacctct   5460
cttttggtgg ggtatccatg tccctcggat caattttcga cggagagacg gcccgccagg   5520
cagcggtaca acccctggca acaggcccca cggatgtgcc tatgtctttc ggatcgtttt   5580
ccgacggaga gattgatgag ctgagccgca gagtaactga gtccgaaccc gtcctgtttg   5640
gatcatttga accgggcgaa gtgaactcaa ttatatcgtc ccgatcagcc gtatcttttc   5700
cactacgcaa gcagagacgt agacgcagga gcaggaggac tgaatactga ctaaccgggg   5760
taggtgggta catattttcg acggacacag gccctgggca cttgcaaaag aagtccgttc   5820
tgcagaacca gcttacagaa ccgaccttgg agcgcaatgt cctggaaaga attcatgccc   5880
cggtgctcga cacgtcgaaa gaggaacaac tcaaactcag gtaccagatg atgcccaccg   5940
aagccaacaa aagtaggtac cagtctcgta aagtagaaaa tcagaaagcc ataaccactg   6000
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact tggatatggt agacgggaca gtcgcctgcc   6240
tggatactgc aaccttctgc cccgctaagc ttagaagtta cccgaaaaaa catgagtata   6300
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgac attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
```

```
aagaagtgcc tatggataga ttcgtcatgg acatgaaaag agacgtgaaa gttacaccag   6660
gcacgaaaca cacagaagaa agaccgaaag tacaagtgat acaagccgca gaacccctgg   6720
cgactgctta cttatgcggg attcaccggg aattagtgcg taggcttacg gccgtcttgc   6780
ttccaaacat tcacacgctt tttgacatgt cggcggagga ttttgatgca atcatagcag   6840
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga aatccggaat gttcctcaca ctttttgtca   7080
acacagtttt gaatgtcgtt atcgccagca gagtactaga agagcggctt aaaacgtcca   7140
gatgtgcagc gttcattggc gacgacaaca tcatacatgg agtagtatct gacaaagaaa   7200
tggctgagag gtgcgccacc tggctcaaca tggaggttaa gatcatcgac gcagtcatcg   7260
gtgagagacc accttacttc tgcggcggat ttatcttgca agattcggtt acttccacag   7320
cgtgccgcgt ggcggatccc ctgaaaaggc tgtttaagtt gggtaaaccg ctcccagccg   7380
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt ttgcccagag caaaagagca ttccaagcca   7560
tcagagggga aataaagcat ctctacggtg gtcctaaata gtcagcatag tacatttcat   7620
ctgactaata ctacaacacc accacctcta gatctagaat actgtaatca tacctggttt   7680
gtttcagagc catatcacca agatagagaa caacctaggt ctccggaggg ggcaagggca   7740
tcagtgtgct cagttgaaaa tcccttgtca acatctaggc cttatcacat cacaagttcc   7800
gccttaaact ctgcagggtg atccaacaac cttaatagca acattattgt taaaggacag   7860
cattagttca cagtcaaaca agcaagattg agaattaact ttgattttga acctgaacac   7920
ccagaggact ggagactcaa caaccctaaa gcctggggta aaacattaga aatagtttaa   7980
agacaaattg ctcggaatca caaaattccg agtatggatt ctcgtcctca gaaagtctgg   8040
tagacgccga gtctcactga atctgacatg gattaccaca agatcttgac agcaggtctg   8100
tccgttcaac aggggattgt tcggcaaaga gtcatcccag tgtatcaagt aaacaatctt   8160
gaggaaattt gccaacttat catacaggcc tttgaagctg gtgttgattt tcaagagagt   8220
gcggacagtt tccttctcat gctttgtctt catcatgcgt accaaggaga ttacaaactt   8280
ttcttggaaa gtggcgcagt caagtatttg gaagggcacg ggttccgttt tgaagtcaag   8340
aagcgtgatg gagtgaagcg ccttgaggaa ttgctgccag cagtatctag tgggagaaac   8400
attaagagaa cacttgctgc catgccggaa gaggagacga cttaatgccg gacatgatgc   8460
caacgatgct gtgatttcaa attcagtggc tcaagctcgt tttcaggtc tattgattgt   8520
caaaacagta cttgatcata tcctacaaaa gacagaacga ggagttcgtc tccatcctct   8580
tgcaaggacc gccaaggtaa aaaatgaggt gaactccttc aaggctgcac tcagctccct   8640
ggccaagcat ggagagtatg ctcctttcgc ccgacttttg aacctttctg gagtaaataa   8700
tcttgagcat ggtcttttcc ctcaactgtc ggcaattgca ctcggagtcg ccacagccca   8760
cgggagcacc ctcgcaggag taaatgttgg agaacagtat caacagctca gagaggcagc   8820
cactgaggct gagaagcaac tccaacaata tgcggagtct cgtgaacttg accatcttgg   8880
acttgatgat caggaaaaga aaattcttat gaacttccat cagaaaaaga acgaaatcag   8940
cttccagcaa acaaacgcga tggtaactct aagaaaagag cgcctggcca agctgacaga   9000
```

```
agctatcact gctgcatcac tgcccaaaac aagtggacat tacgatgatg atgacgacat   9060

tccctttcca ggacccatca atgatgacga caatcctggc catcaagatg atgatccgac   9120

tgactcacag gatacgacca ttcccgatgt ggtagttgat cccgatgatg gaggctacgg   9180

cgaataccaa agttactcgg aaaacggcat gagtgcacca gatgacttgg tcctatgtct   9240

tttagctgta taccagttgc cctgagata cgccacaaaa gtgtctctga gctaaagtgg   9300

tctgtacaca tctcatacat tgtattaggg gcaataatat ctaattgaac ttagccattt   9360

aaaatttagt gcataaatct gggctaactc caccaggtca actccattgg ctgaaaagaa   9420

gcccacctac aacgaacatt actttgagcg ccctcacaat taaaaaataa gagcgtcgtt   9480

ccaacaatcg agcgcaaggt tacaaggttg aactgagagt gtctagacaa caaaatatcg   9540

atactccaga caccaagcaa gacctgagaa aaaaccatgg ccaaagctac gggacgatac   9600

aatctaatat cgcccaaaaa ggacctggag aaaggggttg tcttaagcga cctctgtaac   9660

ttcttagtta gtcaaactat tcaagggtgg aaagtttatt gggctggtat tgagtttgat   9720

gtgactcaca aaggaatggc cctattgcat agactgaaaa ctaatgactt tgcccctgca   9780

tggtcatggc ggtgtttgca gatttggacc tgcgagcggg ttctgacctg aaggctctgc   9840

gcggacttgt ggagacagcc gctcaccttg gctattattt aaatatcgag ggcaggagcg   9900

agagggccaa ggccagggag ggcggccacc accatcacca ccatcaccat tagtaatgag   9960

gtaaccgtgg ggcccaatga tccgaccagc aaaactcgat gtacttccga ggaactgatg  10020

tgcataatgc atcaggctgg tacattagat ccccgcttac cgcgggcaat atagcaacac  10080

taaaaactcg atgtacttcc gaggaagcgc agtgcataat gctgcgcagt gttgccacat  10140

aaccactata ttaaccattt atctagcgga cgccaaaaac tcaatgtatt tctgaggaag  10200

cgtggtgcat aatgccacgc agcgtctgca taacttttat tatttctttt attaatcaac  10260

aaaattttgt ttttaacatt tcaaaaaaaa aaaaaaaaaa aaaaaaaaaa aaaaaaaaag  10320

ggaattcctc gattaattaa gcggccgc                                     10348
```

<210> SEQ ID NO 11
<211> LENGTH: 11655
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: MISC_FEATURE
<222> LOCATION: (1)..(7646)
<223> OTHER INFORMATION: Sindbis gene sequence
<220> FEATURE:
<221> NAME/KEY: MISC_FEATURE
<222> LOCATION: (7647)..(11166)
<223> OTHER INFORMATION: Multi-mutant HIV-1 insert sequence
<220> FEATURE:
<221> NAME/KEY: MISC_FEATURE
<222> LOCATION: (11167)..(11655)
<223> OTHER INFORMATION: Sindbis gene sequence

<400> SEQUENCE: 11

```
attgacggcg tagtacacac tattgaatca aacagccgac caattgcact accatcacaa     60

tggagaagcc agtagtaaac gtagacgtag acccccagag tccgtttgtc gtgcaactgc    120

aaaaaagctt cccgcaattt gaggtagtag cacagcaggt cactccaaat gaccatgcta    180

atgccagagc attttcgcat ctggccagta aactaatcga gctggaggtt cctaccacag    240

cgacgatctt ggacataggc agcgcaccgg ctcgtagaat gttttccgag caccagtatc    300
```

```
attgtgtctg ccccatgcgt agtccagaag acccggaccg catgatgaaa tacgccagta    360
aactggcgga aaaagcgtgc aagattacaa acaagaactt gcatgagaag attaaggatc    420
tccggaccgt acttgatacg ccggatgctg aaacaccatc gctctgcttt cacaacgatg    480
ttacctgcaa catgcgtgcc gaatattccg tcatgcagga cgtgtatatc aacgctcccg    540
gaactatcta tcatcaggct atgaaaggcg tgcggaccct gtactggatt ggcttcgaca    600
ccacccagtt catgttctcg gctatggcag gttcgtaccc tgcgtacaac accaactggg    660
ccgacgagaa agtccttgaa gcgcgtaaca tcggactttg cagcacaaag ctgagtgaag    720
gtaggacagg aaaattgtcg ataatgagga agaaggagtt gaagcccggg tcgcgggttt    780
atttctccgt aggatcgaca ctttatccag aacacagagc cagcttgcag agctggcatc    840
ttccatcggt gttccacttg aatggaaagc agtcgtacac ttgccgctgt gatacagtgg    900
tgagttgcga aggctacgta gtgaagaaaa tcaccatcag tcccgggatc acgggagaaa    960
ccgtgggata cgcggttaca cacaatagcg agggcttctt gctatgcaaa gttactgaca   1020
cagtaaaagg agaacgggta tcgttccctg tgtgcacgta catcccggcc accatatgcg   1080
atcagatgac tggtataatg gccacggata tatcacctga cgatgcacaa aaacttctgg   1140
ttgggctcaa ccagcgaatt gtcattaacg gtaggactaa caggaacacc aacaccatgc   1200
aaaattacct tctgccgatc atagcacaag ggttcagcaa atgggctaag gagcgcaagg   1260
atgatcttga taacgagaaa atgctgggta ctagagaacg caagcttacg tatggctgct   1320
tgtgggcgtt tcgcactaag aaagtacatt cgttttatcg cccacctgga acgcagacct   1380
gcgtaaaagt cccagcctct tttagcgctt ttcccatgtc gtccgtatgg acgacctctt   1440
tgcccatgtc gctgaggcag aaattgaaac tggcattgca accaaagaag gaggaaaaac   1500
tgctgcaggt ctcggaggaa ttagtcatgg aggccaaggc tgcttttgag gatgctcagg   1560
aggaagccag agcggagaag ctccgagaag cacttccacc attagtggca gacaaaggca   1620
tcgaggcagc cgcagaagtt gtctgcgaag tggaggggct ccaggcggac atcggagcag   1680
cattagttga aaccccgcgc ggtcacgtaa ggataatacc tcaagcaaat gaccgtatga   1740
tcggacagta tatcgttgtc tcgccaaact ctgtgctgaa gaatgccaaa ctcgcaccag   1800
cgcacccgct agcagatcag gttaagatca taacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga aagaaaattg tcgcgaaatt gaggccgacg   2340
tgctaagact gaggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
ccatgcaatg cggattcttc aacatgatgc aactaaaggt acatttcaat caccctgaaa   2580
aagacatatg caccaagaca ttctacaagt atatctcccg gcgttgcaca cagccagtta   2640
```

```
cagctattgt atcgacactg cattacgatg gaaagatgaa aaccacgaac ccgtgcaaga   2700
agaacattga aatcgatatt acaggggcca caaagccgaa gccaggggat atcatcctga   2760
catgtttccg cgggtgggtt aagcaattgc aaatcgacta tcccggacat gaagtaatga   2820
cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag cccactaaca   3000
tacctaaagg aaactttcag gctactatag aggactggga agctgaacac aagggaataa   3060
ttgctgcaat aaacagcccc actccccgtg ccaatccgtt cagctgcaag accaacgttt   3120
gctgggcgaa agcattggaa ccgatactag ccacggccgg tatcgtactt accggttgcc   3180
agtggagcga actgttccca cagtttgcgg atgacaaacc acattcggcc atttacgcct   3240
tagacgtaat ttgcattaag tttttcggca tggacttgac aagcggactg ttttctaaac   3300
agagcatccc actaacgtac catcccgccg attcagcgag gccggtagct cattgggaca   3360
acagcccagg aacccgcaag tatgggtacg atcacgccat tgccgccgaa ctctcccgta   3420
gatttccggt gttccagcta gctgggaagg gcacacaact tgatttgcag acggggagaa   3480
ccagagttat ctctgcacag cataacctgg tcccggtgaa ccgcaatctt cctcacgcct   3540
tagtccccga gtacaaggag aagcaacccg gcccggtcaa aaaattcttg aaccagttca   3600
aacaccactc agtacttgtg gtatcagagg aaaaaattga agctccccgt aagagaatcg   3660
aatggatcgc cccgattggc atagccggtg cagataagaa ctacaacctg gctttcgggt   3720
ttccgccgca ggcacggtac gacctggtgt tcatcaacat tggaactaaa tacagaaacc   3780
accactttca gcagtgcgaa gaccatgcgg cgaccttaaa aaccctttcg cgttcggccc   3840
tgaattgcct taacccagga ggcaccctcg tggtgaagtc ctatggctac gccgaccgca   3900
acagtgagga cgtagtcacc gctcttgcca gaaagtttgt cagggtgtct gcagcgagac   3960
cagattgtgt ctcaagcaat acagaaatgt acctgatttt ccgacaacta gacaacagcc   4020
gtacacggca attcaccccg caccatctga attgcgtgat ttcgtccgtg tatgagggta   4080
caagagatgg agttggagcc gcgccgtcat accgcaccaa aagggagaat attgctgact   4140
gtcaagagga agcagttgtc aacgcagcca atccgctggg tagaccaggc gaaggagtct   4200
gccgtgccat ctataaacgt tggccgacca gttttaccga ttcagccacg gagacaggca   4260
ccgcaagaat gactgtgtgc ctaggaaaga aagtgatcca cgcggtcggc cctgatttcc   4320
ggaagcaccc agaagcagaa gccttgaaat tgctacaaaa cgcctaccat gcagtggcag   4380
acttagtaaa tgaacataac atcaagtctg tcgccattcc actgctatct acaggcattt   4440
acgcagccgg aaaagaccgc cttgaagtat cacttaactg cttgacaacc gcgctagaca   4500
gaactgacgc ggacgtaacc atctattgcc tggataagaa gtggaaggaa agaatcgacg   4560
cggcactcca acttaaggag tctgtaacag agctgaagga tgaagatatg gagatcgacg   4620
atgagttagt atggattcat ccagacagtt gcttgaaggg aagaaaggga ttcagtacta   4680
caaaaggaaa attgtattcg tacttcgaag gcaccaaatt ccatcaagca gcaaaagaca   4740
tggcggagat aaaggtcctg ttccctaatg accaggaaag taatgaacaa ctgtgtgcct   4800
acatattggg tgagaccatg gaagcaatcc gcgaaaagtg cccggtcgac cataacccgt   4860
cgtctagccc gcccaaaacg ttgccgtgcc tttgcatgta tgccatgacg ccagaaaggg   4920
tccacagact tagaagcaat aacgtcaaag aagttacagt atgctcctcc acccccttc    4980
ctaagcacaa aattaagaat gttcagaagg ttcagtgcac gaaagtagtc ctgtttaatc   5040
```

```
cgcacactcc cgcattcgtt cccgcccgta agtacataga agtgccagaa cagcctaccg   5100
ctcctcctgc acaggccgag gaggcccccg aagttgtagc gacaccgtca ccatctacag   5160
ctgataacac ctcgcttgat gtcacagaca tctcactgga tatggatgac agtagcgaag   5220
gctcactttt ttcgagcttt agcggatcgg acaactctat tactagtatg gacagttggt   5280
cgtcaggacc tagttcacta gagatagtag accgaaggca ggtggtggtg gctgacgttc   5340
atgccgtcca agagcctgcc cctattccac cgccaaggct aaagaagatg gcccgcctgg   5400
cagcggcaag aaaagagccc actccaccgg caagcaatag ctctgagtcc ctccacctct   5460
cttttggtgg ggtatccatg tccctcggat caattttcga cggagagacg gcccgccagg   5520
cagcggtaca acccctggca acaggcccca cggatgtgcc tatgtctttc ggatcgtttt   5580
ccgacggaga gattgatgag ctgagccgca gagtaactga gtccgaaccc gtcctgtttg   5640
gatcatttga accgggcgaa gtgaactcaa ttatatcgtc ccgatcagcc gtatcttttc   5700
cactacgcaa gcagagacgt agacgcagga gcaggaggac tgaatactga ctaaccgggg   5760
taggtgggta catattttcg acggacacag gccctgggca cttgcaaaag aagtccgttc   5820
tgcagaacca gcttacagaa ccgaccttgg agcgcaatgt cctggaaaga attcatgccc   5880
cggtgctcga cacgtcgaaa gaggaacaac tcaaactcag gtaccagatg atgcccaccg   5940
aagccaacaa aagtaggtac cagtctcgta aagtagaaaa tcagaaagcc ataaccactg   6000
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact tggatatggt agacgggaca gtcgcctgcc   6240
tggatactgc aaccttctgc cccgctaagc ttagaagtta cccgaaaaaa catgagtata   6300
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgac attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
aagaagtgcc tatggataga ttcgtcatgg acatgaaaag agacgtgaaa gttacaccag   6660
gcacgaaaca cacagaagaa agaccgaaag tacaagtgat acaagccgca gaacccctgg   6720
cgactgctta cttatgcggg attcaccggg aattagtgcg taggcttacg gccgtcttgc   6780
ttccaaacat tcacacgctt tttgacatgt cggcggagga ttttgatgca atcatagcag   6840
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga aatccggaat gttcctcaca ctttttgtca   7080
acacagtttt gaatgtcgtt atcgccagca gagtactaga agagcggctt aaaacgtcca   7140
gatgtgcagc gttcattggc gacgacaaca tcatacatgg agtagtatct gacaaagaaa   7200
tggctgagag gtgcgccacc tggctcaaca tggaggttaa gatcatcgac gcagtcatcg   7260
gtgagagacc accttacttc tgcggcggat ttatcttgca agattcggtt acttccacag   7320
cgtgccgcgt ggcggatccc ctgaaaaggc tgtttaagtt gggtaaaccg ctcccagccg   7380
```

```
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt ttgcccagag caaaagagca ttccaagcca   7560
tcagagggga aataaagcat ctctacggtg gtcctaaata gtcagcatag tacatttcat   7620
ctgactaata ctacaacacc accacctcta gaacaaattc agctaccata atgatgcaga   7680
gaggcaattt taggaaccaa agaaagattg ttaagtgttt caattgtggc aaagaagggc   7740
acacagccag aaattgcagg gcccctagga aaaagggctg ttggaaatgt ggaaaggaag   7800
gacaccaaat gaaagattgt actgagagac aggctaattt tttagggaag atctggcctt   7860
cctacaaggg aaggccaggg aattttcttc agagcagacc agagccaaca gccccaccag   7920
aagagagctt caggtctggg gtagagacaa caactccccc tcagaagcag gagccgatag   7980
acaaggaact gtatccttta acttccctca ggtcactctt tggcaacgac ccctcgtcac   8040
aataaagata ggggggcaac taaaggaagc tctaatataa acaggagcag ataatacaat   8100
attagaagaa atgagtttgc caggaagatg gaaaccaaaa atactagtgg gagttggagg   8160
ttttatgaaa gtaagacagt atgatcagat actcatagaa atctgtggac ataaagctat   8220
atctacagta gtagtaggac ctacacctgc caacgtaatt ggaagagatc tgatgactca   8280
gattggttgc actttaaatt ttcccattag ccctattgag actgtaccag taaaattaaa   8340
gccaggaatg gatggcccaa aagttaaaca atggccattg acagaagaaa aaataaaagc   8400
attagtagaa atttgtacag agttggaaaa ggaagggaaa atttcaaaaa ttgggcctga   8460
aaatccatac aatactccag tatttgccat aaagagaaaa aacagttctt cctccagatg   8520
gagaaaagta gtagatctca gagaacttaa taagagaact caagacttct gggaagttca   8580
attaggaata ccacatcccg cagggataga aaagaacaaa tcagcaacaa tactgtaagt   8640
gggtgatgca ttttattcag ttcccttaga tgaagacttc aggaagtata ctgcatttac   8700
catacctagt ataaacaatg agacaccagg gattagatat cagtacaatg tgcttccaat   8760
gggatggaaa ggatcaccag caatattcca aagtagcatg acaaaaatct tagagccttt   8820
tagaaaacaa aatccagaca tagttatctg tcaatacgtg gatgatttgt tagtagcatc   8880
tgacttagaa atagggcagc atagaacaaa aatagaggag ctgagacaac atctgtggag   8940
gtggggactt tacacaccag accaaaaaca tcagaaagaa catccattcc tttggctggg   9000
ttatgaactc catcctgata aatggacagt acagcctata gtgctgccag aaaaagacag   9060
ctggactgtc aatgacatac agaagttagt ggggaaattg aattgggcaa gtcagattta   9120
cccagggatt aaagtaaggc aattatgtaa actccttaga ggaaccaaag cactaacaga   9180
agtaatacca ctaacagaag aagcagagct agaactggca gaaaacagag agattctaaa   9240
agaaccagta catggagtgt attatgaccc atcaaaagac ttaatagcag aaatacagaa   9300
gcaggggcaa ggccaatgga catatcaaat ttatcaagag ccatttaaaa atctgaaaac   9360
aggaaaatat gcaagaatga ggggtgccca cactaatgat gtaaaacaat taacagaggc   9420
agtgcaaaaa ataaccacag aaagcatagt aatatgggga aagactccta aatttaaact   9480
gcccatacaa aaggaaacat gggaaacatg gtggacagag tattggcaag ccacctggat   9540
tcctgagtgg gagtttgtta atacccctcc cttagtgaaa ttatggtacc agttagagaa   9600
agaacccata gtaggagcag aaaccttcta tgtagatggg gcagctaaca gggagactaa   9660
attaggaaaa gcaggatatg ttactaatag aggaagacaa aaagttgtca ccctaactga   9720
cacaacaaat cagaagactg agttacaagc aatttatcta gctttgcagg attcgggatt   9780
```

```
agaagtaaac atagtaacag actcacaata tgcattagga atcattcaag cacaaccaga   9840
tcaaagtgaa tcagagttag tcaatcaaat aatagagcag ttaataaaaa aggaaaaggt   9900
ctatctggca tgggtaccag cacacaaagg aattggagga aatgaacaag tagataaatt   9960
agtcagtgct ggaatcagga aagtactatt tttagatgga atagataagg cccaagatga  10020
acatgagaaa tatcacagta attggagagc aatggctagt gattttaacc tgccacctgt  10080
agtagcaaaa gaaatagtag ccagctgtga taaatgtcag ctaaaaggag aagccatgca  10140
tggacaagta gactgtagtc caggaatatg gcaactagat tgtatacatt tagaaggaaa  10200
agttatcatg gtagcagttc atgtagccag tggatatata gaagcagaag ttattccagc  10260
acaaacaggg caggaagcag catattttct tttaaaatta gcaggaagat ggccagtaaa  10320
aacaatacat actgacaatg gcagcaattt caccggtgct acggttaggg ccgcctgttg  10380
gtgggcggga atcaagcagg cattttcaat tccccgcaat ccccaaagtc acggagtagt  10440
ataatctatg cataaagaat taaagaaaat tataggacag gtaagagatc aggctgaaca  10500
tcttaagaca gcagtacaaa tggcagtatt catccacaat tttaaaagaa aaggggggat  10560
tggggggtac agtgcagggg aaagaatagt agacataata gcaacagaca tacaaactaa  10620
agaattacaa aaacaaatta caaaaattca aaattttcgg gtttattaca gggacagcag  10680
aaatccactt tggaaaggac cagcaaagct cctctggaaa ggtgaagggg cagtagtaat  10740
acaagataat agtgacataa aagtagtgcc aagaagaaaa gcaaagatca ttagggatta  10800
tggaaaacag atggcaggtg atgattgtgt ggcaagtaga caggatgagg attagaacat  10860
ggaaaagttt agtaaaacac catatgtatg tttcagggaa agctagggga tggttttata  10920
gacatcacta tgaaagccct catccaagaa taagttcaga agtacacatc ccactagggg  10980
atgctagatt ggtaataaca acatattggg gtctgcatac aggagaaaga gactggcatt  11040
tgggtcaggg agtctccata gaatggagga aaaagagata tagcacacaa gtagaccctg  11100
aactagcaga ccaactaatt catctgtatt actttgactg tttttcagac tctgctatgg  11160
cgcgccacgt gacgcgtgca tgcatttaaa tatcgagggc aggagcgaga gggccaaggc  11220
cagggagggc ggccaccacc atcaccacca tcaccattag taatgaggta accgtggggc  11280
ccaatgatcc gaccagcaaa actcgatgta cttccgagga actgatgtgc ataatgcatc  11340
aggctggtac attagatccc cgcttaccgc gggcaatata gcaacactaa aaactcgatg  11400
tacttccgag gaagcgcagt gcataatgct gcgcagtgtt gccacataac cactatatta  11460
accatttatc tagcggacgc caaaaactca atgtatttct gaggaagcgt ggtgcataat  11520
gccacgcagc gtctgcataa cttttattat ttcttttatt aatcaacaaa attttgtttt  11580
taacatttca aaaaaaaaaa aaaaaaaaaa aaaaaaaaaa aaaaaaggga attcctcgat  11640
taattaagcg gccgc                                                   11655
```

<210> SEQ ID NO 12
<211> LENGTH: 11649
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: MISC_FEATURE
<222> LOCATION: (1)..(7646)
<223> OTHER INFORMATION: Sindbis gene sequence
<220> FEATURE:
<221> NAME/KEY: MISC_FEATURE
<222> LOCATION: (7647)..(11160)
<223> OTHER INFORMATION: Wild-type HIV-1 insert sequence
<220> FEATURE:
<221> NAME/KEY: MISC_FEATURE
<222> LOCATION: (11161)..(11649)
<223> OTHER INFORMATION: Sindbis gene sequence

<400> SEQUENCE: 12

```
attgacggcg tagtacacac tattgaatca aacagccgac caattgcact accatcacaa     60
tggagaagcc agtagtaaac gtagacgtag acccccagag tccgtttgtc gtgcaactgc    120
aaaaaagctt cccgcaattt gaggtagtag cacagcaggt cactccaaat gaccatgcta    180
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tacgccagta    360
aactggcgga aaaagcgtgc aagattacaa acaagaactt gcatgagaag attaaggatc    420
tccggaccgt acttgatacg ccggatgctg aaacaccatc gctctgcttt cacaacgatg    480
ttacctgcaa catgcgtgcc gaatattccg tcatgcagga cgtgtatatc aacgctcccg    540
gaactatcta tcatcaggct atgaaaggcg tgcggaccct gtactggatt ggcttcgaca    600
ccacccagtt catgttctcg gctatggcag gttcgtaccc tgcgtacaac accaactggg    660
ccgacgagaa agtccttgaa gcgcgtaaca tcggactttg cagcacaaag ctgagtgaag    720
gtaggacagg aaaattgtcg ataatgagga agaaggagtt gaagcccggg tcgcgggttt    780
atttctccgt aggatcgaca ctttatccag aacacagagc cagcttgcag agctggcatc    840
ttccatcggt gttccacttg aatggaaagc agtcgtacac ttgccgctgt gatacagtgg    900
tgagttgcga aggctacgta gtgaagaaaa tcaccatcag tcccgggatc acgggagaaa    960
ccgtgggata cgcggttaca cacaatagcg agggcttctt gctatgcaaa gttactgaca   1020
cagtaaaagg agaacgggta tcgttccctg tgtgcacgta catcccggcc accatatgcg   1080
atcagatgac tggtataatg gccacggata tatcacctga cgatgcacaa aaacttctgg   1140
ttgggctcaa ccagcgaatt gtcattaacg gtaggactaa caggaacacc aacaccatgc   1200
aaaattacct tctgccgatc atagcacaag ggttcagcaa atgggctaag gagcgcaagg   1260
atgatcttga taacgagaaa atgctgggta ctagagaacg caagcttacg tatggctgct   1320
tgtgggcgtt tcgcactaag aaagtacatt cgttttatcg cccacctgga acgcagacct   1380
gcgtaaaagt cccagcctct tttagcgctt ttcccatgtc gtccgtatgg acgacctctt   1440
tgcccatgtc gctgaggcag aaattgaaac tggcattgca accaaagaag gaggaaaaac   1500
tgctgcaggt ctcggaggaa ttagtcatgg aggccaaggc tgcttttgag gatgctcagg   1560
aggaagccag agcggagaag ctccgagaag cacttccacc attagtggca gacaaaggca   1620
tcgaggcagc cgcagaagtt gtctgcgaag tggaggggct ccaggcggac atcggagcag   1680
cattagttga aaccccgcgc ggtcacgtaa ggataatacc tcaagcaaat gaccgtatga   1740
tcggacagta tatcgttgtc tcgccaaact ctgtgctgaa gaatgccaaa ctcgcaccag   1800
cgcacccgct agcagatcag gttaagatca taacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
```

-continued

```
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga aagaaaattg tcgcgaaatt gaggccgacg   2340
tgctaagact gaggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
ccatgcaatg cggattcttc aacatgatgc aactaaaggt acatttcaat caccctgaaa   2580
aagacatatg caccaagaca ttctacaagt atatctcccg gcgttgcaca cagccagtta   2640
cagctattgt atcgacactg cattacgatg gaaagatgaa aaccacgaac ccgtgcaaga   2700
agaacattga aatcgatatt acaggggcca caaagccgaa gccaggggat atcatcctga   2760
catgtttccg cgggtgggtt aagcaattgc aaatcgacta tcccggacat gaagtaatga   2820
cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag cccactaaca   3000
tacctaaagg aaactttcag gctactatag aggactggga agctgaacac aagggaataa   3060
ttgctgcaat aaacagcccc actccccgtg ccaatccgtt cagctgcaag accaacgttt   3120
gctgggcgaa agcattggaa ccgatactag ccacggccgg tatcgtactt accggttgcc   3180
agtggagcga actgttccca cagtttgcgg atgacaaacc acattcggcc atttacgcct   3240
tagacgtaat ttgcattaag tttttcggca tggacttgac aagcggactg ttttctaaac   3300
agagcatccc actaacgtac catcccgccg attcagcgag gccggtagct cattgggaca   3360
acagcccagg aacccgcaag tatgggtacg atcacgccat tgccgccgaa ctctcccgta   3420
gatttccggt gttccagcta gctgggaagg gcacacaact tgatttgcag acggggagaa   3480
ccagagttat ctctgcacag cataacctgg tcccggtgaa ccgcaatctt cctcacgcct   3540
tagtccccga gtacaaggag aagcaacccg gcccggtcaa aaaattcttg aaccagttca   3600
aacaccactc agtacttgtg gtatcagagg aaaaaattga agctccccgt aagagaatcg   3660
aatggatcgc cccgattggc atagccggtg cagataagaa ctacaacctg gctttcgggt   3720
ttccgccgca ggcacggtac gacctggtgt tcatcaacat tggaactaaa tacagaaacc   3780
accactttca gcagtgcgaa gaccatgcgg cgaccttaaa aaccctttcg cgttcggccc   3840
tgaattgcct taacccagga ggcaccctcg tggtgaagtc ctatggctac gccgaccgca   3900
acagtgagga cgtagtcacc gctcttgcca gaaagtttgt cagggtgtct gcagcgagac   3960
cagattgtgt ctcaagcaat acagaaatgt acctgatttt ccgacaacta gacaacagcc   4020
gtacacggca attcaccccg caccatctga attgcgtgat ttcgtccgtg tatgagggta   4080
caagagatgg agttggagcc gcgccgtcat accgcaccaa aagggagaat attgctgact   4140
gtcaagagga agcagttgtc aacgcagcca atccgctggg tagaccaggc gaaggagtct   4200
gccgtgccat ctataaacgt tggccgacca gttttaccga ttcagccacg gagacaggca   4260
ccgcaagaat gactgtgtgc ctaggaaaga aagtgatcca cgcggtcggc cctgatttcc   4320
ggaagcaccc agaagcagaa gccttgaaat tgctacaaaa cgcctaccat gcagtggcag   4380
acttagtaaa tgaacataac atcaagtctg tcgccattcc actgctatct acaggcattt   4440
acgcagccgg aaaagaccgc cttgaagtat cacttaactg cttgacaacc gcgctagaca   4500
```

```
gaactgacgc ggacgtaacc atctattgcc tggataagaa gtggaaggaa agaatcgacg   4560
cggcactcca acttaaggag tctgtaacag agctgaagga tgaagatatg gagatcgacg   4620
atgagttagt atggattcat ccagacagtt gcttgaaggg aagaaaggga ttcagtacta   4680
caaaaggaaa attgtattcg tacttcgaag gcaccaaatt ccatcaagca gcaaaagaca   4740
tggcggagat aaaggtcctg ttccctaatg accaggaaag taatgaacaa ctgtgtgcct   4800
acatattggg tgagaccatg gaagcaatcc gcgaaaagtg cccggtcgac cataacccgt   4860
cgtctagccc gcccaaaacg ttgccgtgcc tttgcatgta tgccatgacg ccagaaaggg   4920
tccacagact tagaagcaat aacgtcaaag aagttacagt atgctcctcc acccccettc   4980
ctaagcacaa aattaagaat gttcagaagg ttcagtgcac gaaagtagtc ctgtttaatc   5040
cgcacactcc cgcattcgtt cccgcccgta agtacataga agtgccagaa cagcctaccg   5100
ctcctcctgc acaggccgag gaggcccccg aagttgtagc gacaccgtca ccatctacag   5160
ctgataacac ctcgcttgat gtcacagaca tctcactgga tatggatgac agtagcgaag   5220
gctcactttt ttcgagcttt agcggatcgg acaactctat tactagtatg gacagttggt   5280
cgtcaggacc tagttcacta gagatagtag accgaaggca ggtggtggtg gctgacgttc   5340
atgccgtcca agagcctgcc cctattccac cgccaaggct aaagaagatg gcccgcctgg   5400
cagcggcaag aaaagagccc actccaccgg caagcaatag ctctgagtcc ctccacctct   5460
cttttggtgg ggtatccatg tccctcggat caattttcga cggagagacg gcccgccagg   5520
cagcggtaca acccctggca acaggcccca cggatgtgcc tatgtctttc ggatcgtttt   5580
ccgacggaga gattgatgag ctgagccgca gagtaactga gtccgaaccc gtcctgtttg   5640
gatcatttga accgggcgaa gtgaactcaa ttatatcgtc ccgatcagcc gtatcttttc   5700
cactacgcaa gcagagacgt agacgcagga gcaggaggac tgaatactga ctaaccgggg   5760
taggtgggta catattttcg acggacacag gccctgggca cttgcaaaag aagtccgttc   5820
tgcagaacca gcttacagaa ccgaccttgg agcgcaatgt cctggaaaga attcatgccc   5880
cggtgctcga cacgtcgaaa gaggaacaac tcaaactcag gtaccagatg atgcccaccg   5940
aagccaacaa aagtaggtac cagtctcgta aagtagaaaa tcagaaagcc ataaccactg   6000
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact tggatatggt agacgggaca gtcgcctgcc   6240
tggatactgc aaccttctgc cccgctaagc ttagaagtta cccgaaaaaa catgagtata   6300
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgac attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
aagaagtgcc tatggataga ttcgtcatgg acatgaaaag agacgtgaaa gttacaccag   6660
gcacgaaaca cacagaagaa agaccgaaag tacaagtgat acaagccgca gaacccctgg   6720
cgactgctta cttatgcggg attcaccggg aattagtgcg taggcttacg gccgtcttgc   6780
ttccaaacat tcacacgctt tttgacatgt cggcggagga ttttgatgca atcatagcag   6840
```

-continued

```
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga aatccggaat gttcctcaca ctttttgtca   7080
acacagtttt gaatgtcgtt atcgccagca gagtactaga agagcggctt aaaacgtcca   7140
gatgtgcagc gttcattggc gacgacaaca tcatacatgg agtagtatct gacaaagaaa   7200
tggctgagag gtgcgccacc tggctcaaca tggaggttaa gatcatcgac gcagtcatcg   7260
gtgagagacc accttacttc tgcggcggat ttatcttgca agattcggtt acttccacag   7320
cgtgccgcgt ggcggatccc ctgaaaaggc tgtttaagtt gggtaaaccg ctcccagccg   7380
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt ttgcccagag caaaagagca ttccaagcca   7560
tcagagggga aataaagcat ctctacggtg gtcctaaata gtcagcatag tacatttcat   7620
ctgactaata ctacaacacc accacctcta gaacaaattc agctaccata atgatgcaga   7680
gaggcaattt taggaaccaa agaaagattg ttaagtgttt caattgtggc aaagaagggc   7740
acacagccag aaattgcagg gcccctagga aaaagggctg ttggaaatgt ggaaaggaag   7800
gacaccaaat gaaagattgt actgagagac aggctaattt tttagggaag atctggcctt   7860
cctacaaggg aaggccaggg aattttcttc agagcagacc agagccaaca gccccaccag   7920
aagagagctt caggtctggg gtagagacaa caactccccc tcagaagcag gagccgatag   7980
acaaggaact gtatccttta acttccctca ggtcactctt tggcaacgac ccctcgtcac   8040
aataaagata ggggggcaac taaaggaagc tctattataa acaggagcag atgatacagt   8100
attagaagaa atgagtttgc caggaagatg gaaaccaaaa atgatagggg gaattggagg   8160
ttttatcaaa gtaagacagt atgatcagat actcatagaa atctgtggac ataaagctat   8220
aggtacagta ttagtaggac ctacacctgt caacataatt ggaagaaatc tgttgactca   8280
gattggttgc actttaaatt ttcccattag ccctattgag actgtaccag taaaattaaa   8340
gccaggaatg gatggcccaa aagttaaaca atggccattg acagaagaaa aaataaaagc   8400
attagtagaa atttgtacag agatggaaaa ggaagggaaa atttcaaaaa ttgggcctga   8460
aaatccatac aatactccag tatttgccat aaagaaaaaa gacagtacta aatggagaaa   8520
attagtagat ttcagagaac ttaataagag aactcaagac ttctgggaag ttcaattagg   8580
aataccacat cccgcagggt taaaaaagaa aaaatcagta acagtactgt aagtgggtga   8640
tgcatatttt tcagttccct tagatgaaga cttcaggaag tatactgcat ttaccatacc   8700
tagtataaac aatgagacac cagggattag atatcagtac aatgtgcttc cacagggatg   8760
gaaaggatca ccagcaatat tccaaagtag catgacaaaa atcttagagc cttttagaaa   8820
acaaaatcca gacatagtta tctatcaata catggatgat ttgtatgtag gatctgactt   8880
agaaataggg cagcatagaa caaaaataga ggagctgaga caacatctgt tgaggtgggg   8940
acttaccaca ccagacaaaa aacatcagaa agaacctcca ttcctttgga tgggttatga   9000
actccatcct gataaatgga cagtacagcc tatagtgctg ccagaaaaag acagctggac   9060
tgtcaatgac atacagaagt tagtggggaa attgaattgg gcaagtcaga tttacccagg   9120
gattaaagta aggcaattat gtaaactcct tagaggaacc aaagcactaa cagaagtaat   9180
accactaaca gaagaagcag agctagaact ggcagaaaac agagagattc taaaagaacc   9240
```

```
agtacatgga gtgtattatg acccatcaaa agacttaata gcagaaatac agaagcaggg   9300
gcaaggccaa tggacatatc aaatttatca agagccattt aaaaatctga aaacaggaaa   9360
atatgcaaga atgaggggtg cccacactaa tgatgtaaaa caattaacag aggcagtgca   9420
aaaaataacc acagaaagca tagtaatatg ggaaagact  cctaaattta aactgcccat   9480
acaaaaggaa acatgggaaa catggtggac agagtattgg caagccacct ggattcctga   9540
gtgggagttt gttaataccc ctcccttagt gaaattatgg taccagttag agaaagaacc   9600
catagtagga gcagaaacct tctatgtaga tggggcagct aacagggaga ctaaattagg   9660
aaaagcagga tatgttacta atagaggaag acaaaaagtt gtcaccctaa ctgacacaac   9720
aaatcagaag actgagttac aagcaattta tctagctttg caggattcgg gattagaagt   9780
aaacatagta acagactcac aatatgcatt aggaatcatt caagcacaac cagatcaaag   9840
tgaatcagag ttagtcaatc aaataataga gcagttaata aaaaaggaaa aggtctatct   9900
ggcatgggta ccagcacaca aaggaattgg aggaaatgaa caagtagata aattagtcag   9960
tgctggaatc aggaaagtac tatttttaga tggaatagat aaggcccaag atgaacatga  10020
gaaatatcac agtaattgga gagcaatggc tagtgatttt aacctgccac ctgtagtagc  10080
aaaagaaata gtagccagct gtgataaatg tcagctaaaa ggagaagcca tgcatggaca  10140
agtagactgt agtccaggaa tatggcaact agattgtaca catttagaag gaaaagttat  10200
cctggtagca gttcatgtag ccagtggata tatagaagca gaagttattc cagcagaaac  10260
agggcaggaa acagcatatt ttcttttaaa attagcagga agatggccag taaaaacaat  10320
acatactgac aatggcagca atttcaccgg tgctacggtt agggccgcct gttggtgggc  10380
gggaatcaag caggaatttg gaattcccta caatccccaa agtcaaggag tagtataatc  10440
tatgaataaa gaattaaaga aaattatagg acaggtaaga gatcaggctg aacatcttaa  10500
gacagcagta caaatggcag tattcatcca caattttaaa agaaaagggg ggattggggg  10560
gtacagtgca ggggaaagaa tagtagacat aatagcaaca gacatacaaa ctaaagaatt  10620
acaaaaacaa attacaaaaa ttcaaaattt tcgggtttat tacagggaca gcagaaatcc  10680
actttggaaa ggaccagcaa agctcctctg gaaaggtgaa ggggcagtag taatacaaga  10740
taatagtgac ataaaagtag tgccaagaag aaaagcaaag atcattaggg attatggaaa  10800
acagatggca ggtgatgatt gtgtggcaag tagacaggat gaggattaga acatggaaaa  10860
gtttagtaaa acaccatatg tatgtttcag ggaaagctag gggatggttt tatagacatc  10920
actatgaaag ccctcatcca agaataagtt cagaagtaca catcccacta ggggatgcta  10980
gattggtaat aacaacatat tggggtctgc atacaggaga aagagactgg catttgggtc  11040
agggagtctc catagaatgg aggaaaaaga gatatagcac acaagtagac cctgaactag  11100
cagaccaact aattcatctg tattactttg actgtttttc agactctgct atggcgcgcc  11160
acgtgacgcg tgcatgcatt taaatatcga gggcaggagc gagagggcca aggccaggga  11220
gggcggccac caccatcacc accatcacca ttagtaatga ggtaaccgtg gggcccaatg  11280
atccgaccag caaaactcga tgtacttccg aggaactgat gtgcataatg catcaggctg  11340
gtacattaga tccccgctta ccgcgggcaa tatagcaaca ctaaaaactc gatgtacttc  11400
cgaggaagcg cagtgcataa tgctgcgcag tgttgccaca taaccactat attaaccatt  11460
tatctagcgg acgccaaaaa ctcaatgtat ttctgaggaa gcgtggtgca taatgccacg  11520
cagcgtctgc ataactttta ttatttcttt tattaatcaa caaaattttg tttttaacat  11580
```

```
ttcaaaaaaa aaaaaaaaaa aaaaaaaaaa aaaaaaaaaa gggaattcct cgattaatta  11640

agcggccgc                                                          11649


<210> SEQ ID NO 13
<211> LENGTH: 9675
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: MISC_FEATURE
<222> LOCATION: (1)..(7646)
<223> OTHER INFORMATION: Sindbis gene sequence
<220> FEATURE:
<221> NAME/KEY: MISC_FEATURE
<222> LOCATION: (7647)..(9186)
<223> OTHER INFORMATION: Mutant HIV-1 insert sequence
<220> FEATURE:
<221> NAME/KEY: MISC_FEATURE
<222> LOCATION: (9187)..(9675)
<223> OTHER INFORMATION: Sindbis gene sequence

<400> SEQUENCE: 13

attgacggcg tagtacacac tattgaatca aacagccgac caattgcact accatcacaa     60

tggagaagcc agtagtaaac gtagacgtag acccccagag tccgtttgtc gtgcaactgc    120

aaaaaagctt cccgcaattt gaggtagtag cacagcaggt cactccaaat gaccatgcta    180

atgccagagc attttcgcat ctggccagta aactaatcga gctggaggtt cctaccacag    240

cgacgatctt ggacataggc agcgcaccgg ctcgtagaat gttttccgag caccagtatc    300

attgtgtctg ccccatgcgt agtccagaag acccggaccg catgatgaaa tacgccagta    360

aactggcgga aaaagcgtgc aagattacaa acaagaactt gcatgagaag attaaggatc    420

tccggaccgt acttgatacg ccggatgctg aaacaccatc gctctgcttt cacaacgatg    480

ttacctgcaa catgcgtgcc gaatattccg tcatgcagga cgtgtatatc aacgctcccg    540

gaactatcta tcatcaggct atgaaaggcg tgcggaccct gtactggatt ggcttcgaca    600

ccacccagtt catgttctcg gctatggcag gttcgtaccc tgcgtacaac accaactggg    660

ccgacgagaa agtccttgaa gcgcgtaaca tcggactttg cagcacaaag ctgagtgaag    720

gtaggacagg aaaattgtcg ataatgagga agaaggagtt gaagcccggg tcgcgggttt    780

atttctccgt aggatcgaca ctttatccag aacacagagc cagcttgcag agctggcatc    840

ttccatcggt gttccacttg aatggaaagc agtcgtacac ttgccgctgt gatacagtgg    900

tgagttgcga aggctacgta gtgaagaaaa tcaccatcag tcccgggatc acgggagaaa    960

ccgtgggata cgcggttaca cacaatagcg agggcttctt gctatgcaaa gttactgaca   1020

cagtaaaagg agaacgggta tcgttccctg tgtgcacgta catcccggcc accatatgcg   1080

atcagatgac tggtataatg gccacggata tatcacctga cgatgcacaa aaacttctgg   1140

ttgggctcaa ccagcgaatt gtcattaacg gtaggactaa caggaacacc aacaccatgc   1200

aaaattacct tctgccgatc atagcacaag ggttcagcaa atgggctaag gagcgcaagg   1260

atgatcttga taacgagaaa atgctgggta ctagagaacg caagcttacg tatggctgct   1320

tgtgggcgtt tcgcactaag aaagtacatt cgttttatcg cccacctgga acgcagacct   1380

gcgtaaaagt cccagcctct tttagcgctt ttcccatgtc gtccgtatgg acgacctctt   1440

tgcccatgtc gctgaggcag aaattgaaac tggcattgca accaaagaag gaggaaaaac   1500

tgctgcaggt ctcggaggaa ttagtcatgg aggccaaggc tgcttttgag gatgctcagg   1560
```

```
aggaagccag agcggagaag ctccgagaag cacttccacc attagtggca gacaaaggca   1620
tcgaggcagc cgcagaagtt gtctgcgaag tggaggggct ccaggcggac atcggagcag   1680
cattagttga aaccccgcgc ggtcacgtaa ggataatacc tcaagcaaat gaccgtatga   1740
tcggacagta tatcgttgtc tcgccaaact ctgtgctgaa gaatgccaaa ctcgcaccag   1800
cgcacccgct agcagatcag gttaagatca taacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga aagaaaattg tcgcgaaatt gaggccgacg   2340
tgctaagact gaggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
ccatgcaatg cggattcttc aacatgatgc aactaaaggt acatttcaat caccctgaaa   2580
aagacatatg caccaagaca ttctacaagt atatctcccg gcgttgcaca cagccagtta   2640
cagctattgt atcgacactg cattacgatg gaaagatgaa aaccacgaac ccgtgcaaga   2700
agaacattga aatcgatatt acaggggcca caaagccgaa gccaggggat atcatcctga   2760
catgtttccg cgggtgggtt aagcaattgc aaatcgacta tcccggacat gaagtaatga   2820
cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag cccactaaca   3000
tacctaaagg aaactttcag gctactatag aggactggga agctgaacac aagggaataa   3060
ttgctgcaat aaacagcccc actccccgtg ccaatccgtt cagctgcaag accaacgttt   3120
gctgggcgaa agcattggaa ccgatactag ccacggccgg tatcgtactt accggttgcc   3180
agtggagcga actgttccca cagtttgcgg atgacaaacc acattcggcc atttacgcct   3240
tagacgtaat ttgcattaag tttttcggca tggacttgac aagcggactg ttttctaaac   3300
agagcatccc actaacgtac catcccgccg attcagcgag gccggtagct cattgggaca   3360
acagcccagg aacccgcaag tatgggtacg atcacgccat tgccgccgaa ctctcccgta   3420
gatttccggt gttccagcta gctgggaagg gcacacaact tgatttgcag acggggagaa   3480
ccagagttat ctctgcacag cataacctgg tcccggtgaa ccgcaatctt cctcacgcct   3540
tagtccccga gtacaaggag aagcaacccg gcccggtcaa aaaattcttg aaccagttca   3600
aacaccactc agtacttgtg gtatcagagg aaaaaattga agctccccgt aagagaatcg   3660
aatggatcgc cccgattggc atagccggtg cagataagaa ctacaacctg gctttcgggt   3720
ttccgccgca ggcacggtac gacctggtgt tcatcaacat tggaactaaa tacagaaacc   3780
accactttca gcagtgcgaa gaccatgcgg cgaccttaaa aaccctttcg cgttcggccc   3840
tgaattgcct taacccagga ggcaccctcg tggtgaagtc ctatggctac gccgaccgca   3900
acagtgagga cgtagtcacc gctcttgcca gaaagtttgt cagggtgtct gcagcgagac   3960
```

```
cagattgtgt ctcaagcaat acagaaatgt acctgatttt ccgacaacta gacaacagcc   4020
gtacacggca attcaccccg caccatctga attgcgtgat ttcgtccgtg tatgagggta   4080
caagagatgg agttggagcc gcgccgtcat accgcaccaa aagggagaat attgctgact   4140
gtcaagagga agcagttgtc aacgcagcca atccgctggg tagaccaggc gaaggagtct   4200
gccgtgccat ctataaacgt tggccgacca gttttaccga ttcagccacg gagacaggca   4260
ccgcaagaat gactgtgtgc ctaggaaaga aagtgatcca cgcggtcggc cctgatttcc   4320
ggaagcaccc agaagcagaa gccttgaaat tgctacaaaa cgcctaccat gcagtggcag   4380
acttagtaaa tgaacataac atcaagtctg tcgccattcc actgctatct acaggcattt   4440
acgcagccgg aaaagaccgc cttgaagtat cacttaactg cttgacaacc gcgctagaca   4500
gaactgacgc ggacgtaacc atctattgcc tggataagaa gtggaaggaa agaatcgacg   4560
cggcactcca acttaaggag tctgtaacag agctgaagga tgaagatatg gagatcgacg   4620
atgagttagt atggattcat ccagacagtt gcttgaaggg aagaaaggga ttcagtacta   4680
caaaaggaaa attgtattcg tacttcgaag gcaccaaatt ccatcaagca gcaaaagaca   4740
tggcggagat aaaggtcctg ttccctaatg accaggaaag taatgaacaa ctgtgtgcct   4800
acatattggg tgagaccatg gaagcaatcc gcgaaaagtg cccggtcgac cataacccgt   4860
cgtctagccc gcccaaaacg ttgccgtgcc tttgcatgta tgccatgacg ccagaaaggg   4920
tccacagact tagaagcaat aacgtcaaag aagttacagt atgctcctcc acccccttc    4980
ctaagcacaa aattaagaat gttcagaagg ttcagtgcac gaaagtagtc ctgtttaatc   5040
cgcacactcc cgcattcgtt cccgcccgta agtacataga agtgccagaa cagcctaccg   5100
ctcctcctgc acaggccgag gaggcccccg aagttgtagc gacaccgtca ccatctacag   5160
ctgataacac ctcgcttgat gtcacagaca tctcactgga tatggatgac agtagcgaag   5220
gctcactttt ttcgagcttt agcggatcgg acaactctat tactagtatg gacagttggt   5280
cgtcaggacc tagttcacta gagatagtag accgaaggca ggtggtggtg gctgacgttc   5340
atgccgtcca agagcctgcc cctattccac cgccaaggct aaagaagatg gcccgcctgg   5400
cagcggcaag aaaagagccc actccaccgg caagcaatag ctctgagtcc ctccacctct   5460
cttttggtgg ggtatccatg tccctcggat caattttcga cggagagacg gcccgccagg   5520
cagcggtaca acccctggca acaggcccca cggatgtgcc tatgtctttc ggatcgtttt   5580
ccgacggaga gattgatgag ctgagccgca gagtaactga gtccgaaccc gtcctgtttg   5640
gatcatttga accgggcgaa gtgaactcaa ttatatcgtc ccgatcagcc gtatcttttc   5700
cactacgcaa gcagagacgt agacgcagga gcaggaggac tgaatactga ctaaccgggg   5760
taggtgggta catattttcg acggacacag gccctgggca cttgcaaaag aagtccgttc   5820
tgcagaacca gcttacagaa ccgaccttgg agcgcaatgt cctggaaaga attcatgccc   5880
cggtgctcga cacgtcgaaa gaggaacaac tcaaactcag gtaccagatg atgcccaccg   5940
aagccaacaa aagtaggtac cagtctcgta aagtagaaaa tcagaaagcc ataaccactg   6000
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact tggatatggt agacgggaca gtcgcctgcc   6240
tggatactgc aaccttctgc cccgctaagc ttagaagtta cccgaaaaaa catgagtata   6300
```

```
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgac attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
aagaagtgcc tatggataga ttcgtcatgg acatgaaaag agacgtgaaa gttacaccag   6660
gcacgaaaca cacagaagaa agaccgaaag tacaagtgat acaagccgca gaacccctgg   6720
cgactgctta cttatgcggg attcaccggg aattagtgcg taggcttacg gccgtcttgc   6780
ttccaaacat tcacacgctt tttgacatgt cggcggagga ttttgatgca atcatagcag   6840
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga aatccggaat gttcctcaca ctttttgtca   7080
acacagtttt gaatgtcgtt atcgccagca gagtactaga agagcggctt aaaacgtcca   7140
gatgtgcagc gttcattggc gacgacaaca tcatacatgg agtagtatct gacaaagaaa   7200
tggctgagag gtgcgccacc tggctcaaca tggaggttaa gatcatcgac gcagtcatcg   7260
gtgagagacc accttacttc tgcggcggat ttatcttgca agattcggtt acttccacag   7320
cgtgccgcgt ggcggatccc ctgaaaaggc tgtttaagtt gggtaaaccg ctcccagccg   7380
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt ttgcccagag caaaagagca ttccaagcca   7560
tcagagggga aataaagcat ctctacggtg gtcctaaata gtcagcatag tacatttcat   7620
ctgactaata ctacaacacc accacctcta gaatgatctg tagtgctaca gaaaaattgt   7680
gggtcacagt ctattatggg gtacctgtgt ggaaggaagc aaccaccact ctattttgtg   7740
catcagatgc taaagcatat gatacagagg tacataatgt ttgggccaca catgcctgtg   7800
tacccacaga ccccaaccca caagaagtag tattggtaaa tgtgacagaa aattttaaca   7860
tgtggaaaaa tgacatggta gaacagatgc atgaggatat aatcagttta tgggatcaaa   7920
gcctaaagcc atgtgtaaaa ttaaccccac tctgtgttag tttaaagtgc actgatttga   7980
agaatgatac taataccaat agtagtagcg ggagaatgat aatggagaaa ggagagataa   8040
aaaactgctc tttcaatatc agcacaagca taagaggtaa ggtgcagaaa gaatatgcat   8100
ttttttataa acttgatata ataccaatag ataatgatac taccagctat aagttgacaa   8160
gttgtaacac ctcagtcatt acacaggcct gtccaaaggt atcctttgag ccaattccca   8220
tacattattg tgccccggct ggttttgcga ttctaaaatg taataataag acgttcaatg   8280
gaacaggacc atgtacaaat gtcagcacag tacaatgtac acatggaatt aggccagtag   8340
tatcaactca actgctgtta aatggcagtc tagcagaaga agaggtagta attagatctg   8400
tcaatttcac ggacaatgct aaaaccataa tagtacagct gaacacatct gtagaaatta   8460
attgtacaag acccaacaac aatacaagaa aaagaatccg tatccagaga ggaccaggga   8520
gagcatttgt tacaatagga aaaataggaa atatgagaca agcacattgt aacattagta   8580
gagcaaaatg gaataacact ttaaaacaga tagctagcaa attaagagaa caatttggaa   8640
ataataaaac aataatcttt aagcaatcct caggaggggga cccagaaatt gtaacgcaca   8700
```

```
gttttaattg tggaggggaa tttttctact gtaattcaac acaactgttt aatagtactt   8760
ggtttaatag tacttggagt actgaagggt caaataacac tgaaggaagt gacacaatca   8820
ccctcccatg cagaataaaa caaattataa acatgtggca gaaagtagga aaagcaatgt   8880
atgcccctcc catcagtgga caaattagat gttcatcaaa tattacaggg ctgctattaa   8940
caagagatgg tggtaatagc aacaatgagt ccgagatctt cagacctgga ggaggagata   9000
tgagggacaa ttggagaagt gaattatata aatataaagt agtaaaaatt gaaccattag   9060
gagtagcacc caccaaggca aagagaagag tggtgcagag agaaaaaaga gcagtgggaa   9120
taggagcttt gttccttggg ttcttgggag cagcaggaag cactatgggc gcagcctcgg   9180
cgcgccacgt gacgcgtgca tgcatttaaa tatcgagggc aggagcgaga gggccaaggc   9240
cagggagggc ggccaccacc atcaccacca tcaccattag taatgaggta accgtggggc   9300
ccaatgatcc gaccagcaaa actcgatgta cttccgagga actgatgtgc ataatgcatc   9360
aggctggtac attagatccc cgcttaccgc gggcaatata gcaacactaa aaactcgatg   9420
tacttccgag gaagcgcagt gcataatgct gcgcagtgtt gccacataac cactatatta   9480
accatttatc tagcggacgc caaaaactca atgtatttct gaggaagcgt ggtgcataat   9540
gccacgcagc gtctgcataa cttttattat ttcttttatt aatcaacaaa attttgtttt   9600
taacatttca aaaaaaaaaa aaaaaaaaaa aaaaaaaaaa aaaaaaggga attcctcgat   9660
taattaagcg gccgc                                                    9675
```

```
<210> SEQ ID NO 14
<211> LENGTH: 9670
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: MISC_FEATURE
<222> LOCATION: (1)..(7646)
<223> OTHER INFORMATION: Sindbis gene sequence
<220> FEATURE:
<221> NAME/KEY: MISC_FEATURE
<222> LOCATION: (7647)..(9181)
<223> OTHER INFORMATION: Wild-type HIV-1 insert sequence
<220> FEATURE:
<221> NAME/KEY: MISC_FEATURE
<222> LOCATION: (9182)..(9670)
<223> OTHER INFORMATION: Sindbis gene sequence

<400> SEQUENCE: 14
```

```
attgacggcg tagtacacac tattgaatca aacagccgac caattgcact accatcacaa     60
tggagaagcc agtagtaaac gtagacgtag acccccagag tccgtttgtc gtgcaactgc    120
aaaaaagctt cccgcaattt gaggtagtag cacagcaggt cactccaaat gaccatgcta    180
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tacgccagta    360
aactggcgga aaaagcgtgc aagattacaa acaagaactt gcatgagaag attaaggatc    420
tccggaccgt acttgatacg ccggatgctg aaacaccatc gctctgcttt cacaacgatg    480
ttacctgcaa catgcgtgcc gaatattccg tcatgcagga cgtgtatatc aacgctcccg    540
gaactatcta tcatcaggct atgaaaggcg tgcggaccct gtactggatt ggcttcgaca    600
ccacccagtt catgttctcg gctatggcag gttcgtaccc tgcgtacaac accaactggg    660
```

```
ccgacgagaa agtccttgaa gcgcgtaaca tcggactttg cagcacaaag ctgagtgaag    720
gtaggacagg aaaattgtcg ataatgagga agaaggagtt gaagcccggg tcgcgggttt    780
atttctccgt aggatcgaca ctttatccag aacacagagc cagcttgcag agctggcatc    840
ttccatcggt gttccacttg aatggaaagc agtcgtacac ttgccgctgt gatacagtgg    900
tgagttgcga aggctacgta gtgaagaaaa tcaccatcag tcccgggatc acgggagaaa    960
ccgtgggata cgcggttaca cacaatagcg agggcttctt gctatgcaaa gttactgaca   1020
cagtaaaagg agaacgggta tcgttccctg tgtgcacgta catcccggcc accatatgcg   1080
atcagatgac tggtataatg gccacggata tatcacctga cgatgcacaa aaacttctgg   1140
ttgggctcaa ccagcgaatt gtcattaacg gtaggactaa caggaacacc aacaccatgc   1200
aaaattacct tctgccgatc atagcacaag ggttcagcaa atgggctaag gagcgcaagg   1260
atgatcttga taacgagaaa atgctgggta ctagagaacg caagcttacg tatggctgct   1320
tgtgggcgtt tcgcactaag aaagtacatt cgttttatcg cccacctgga acgcagacct   1380
gcgtaaaagt cccagcctct tttagcgctt ttcccatgtc gtccgtatgg acgacctctt   1440
tgcccatgtc gctgaggcag aaattgaaac tggcattgca accaaagaag gaggaaaaac   1500
tgctgcaggt ctcggaggaa ttagtcatgg aggccaaggc tgcttttgag gatgctcagg   1560
aggaagccag agcggagaag ctccgagaag cacttccacc attagtggca gacaaaggca   1620
tcgaggcagc cgcagaagtt gtctgcgaag tggaggggct ccaggcggac atcggagcag   1680
cattagttga aaccccgcgc ggtcacgtaa ggataatacc tcaagcaaat gaccgtatga   1740
tcggacagta tatcgttgtc tcgccaaact ctgtgctgaa gaatgccaaa ctcgcaccag   1800
cgcacccgct agcagatcag gttaagatca taacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga aagaaaattg tcgcgaaatt gaggccgacg   2340
tgctaagact gaggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
ccatgcaatg cggattcttc aacatgatgc aactaaaggt acatttcaat caccctgaaa   2580
aagacatatg caccaagaca ttctacaagt atatctcccg gcgttgcaca cagccagtta   2640
cagctattgt atcgacactg cattacgatg gaaagatgaa aaccacgaac ccgtgcaaga   2700
agaacattga aatcgatatt acaggggcca caaagccgaa gccaggggat atcatcctga   2760
catgtttccg cgggtgggtt aagcaattgc aaatcgacta tcccggacat gaagtaatga   2820
cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag cccactaaca   3000
```

-continued

```
tacctaaagg aaactttcag gctactatag aggactggga agctgaacac aagggaataa   3060
ttgctgcaat aaacagcccc actccccgtg ccaatccgtt cagctgcaag accaacgttt   3120
gctgggcgaa agcattggaa ccgatactag ccacggccgg tatcgtactt accggttgcc   3180
agtggagcga actgttccca cagtttgcgg atgacaaacc acattcggcc atttacgcct   3240
tagacgtaat ttgcattaag tttttcggca tggacttgac aagcggactg ttttctaaac   3300
agagcatccc actaacgtac catcccgccg attcagcgag gccggtagct cattgggaca   3360
acagcccagg aacccgcaag tatgggtacg atcacgccat tgccgccgaa ctctcccgta   3420
gatttccggt gttccagcta gctgggaagg gcacacaact tgatttgcag acggggagaa   3480
ccagagttat ctctgcacag cataacctgg tcccggtgaa ccgcaatctt cctcacgcct   3540
tagtccccga gtacaaggag aagcaacccg gcccggtcaa aaaattcttg aaccagttca   3600
aacaccactc agtacttgtg gtatcagagg aaaaaattga agctccccgt aagagaatcg   3660
aatggatcgc cccgattggc atagccggtg cagataagaa ctacaacctg gctttcgggt   3720
ttccgccgca ggcacggtac gacctggtgt tcatcaacat tggaactaaa tacagaaacc   3780
accactttca gcagtgcgaa gaccatgcgg cgaccttaaa aaccctttcg cgttcggccc   3840
tgaattgcct taacccagga ggcaccctcg tggtgaagtc ctatggctac gccgaccgca   3900
acagtgagga cgtagtcacc gctcttgcca gaaagtttgt cagggtgtct gcagcgagac   3960
cagattgtgt ctcaagcaat acagaaatgt acctgatttt ccgacaacta gacaacagcc   4020
gtacacggca attcaccccg caccatctga attgcgtgat ttcgtccgtg tatgagggta   4080
caagagatgg agttggagcc gcgccgtcat accgcaccaa aagggagaat attgctgact   4140
gtcaagagga agcagttgtc aacgcagcca atccgctggg tagaccaggc gaaggagtct   4200
gccgtgccat ctataaacgt tggccgacca gttttaccga ttcagccacg gagacaggca   4260
ccgcaagaat gactgtgtgc ctaggaaaga aagtgatcca cgcggtcggc cctgatttcc   4320
ggaagcaccc agaagcagaa gccttgaaat tgctacaaaa cgcctaccat gcagtggcag   4380
acttagtaaa tgaacataac atcaagtctg tcgccattcc actgctatct acaggcattt   4440
acgcagccgg aaaagaccgc cttgaagtat cacttaactg cttgacaacc gcgctagaca   4500
gaactgacgc ggacgtaacc atctattgcc tggataagaa gtggaaggaa agaatcgacg   4560
cggcactcca acttaaggag tctgtaacag agctgaagga tgaagatatg gagatcgacg   4620
atgagttagt atggattcat ccagacagtt gcttgaaggg aagaaaggga ttcagtacta   4680
caaaaggaaa attgtattcg tacttcgaag gcaccaaatt ccatcaagca gcaaaagaca   4740
tggcggagat aaaggtcctg ttccctaatg accaggaaag taatgaacaa ctgtgtgcct   4800
acatattggg tgagaccatg gaagcaatcc gcgaaaagtg cccggtcgac cataacccgt   4860
cgtctagccc gcccaaaacg ttgccgtgcc tttgcatgta tgccatgacg ccagaaaggg   4920
tccacagact tagaagcaat aacgtcaaag aagttacagt atgctcctcc acccccttc    4980
ctaagcacaa aattaagaat gttcagaagg ttcagtgcac gaaagtagtc ctgtttaatc   5040
cgcacactcc cgcattcgtt cccgcccgta agtacataga agtgccagaa cagcctaccg   5100
ctcctcctgc acaggccgag gaggcccccg aagttgtagc gacaccgtca ccatctacag   5160
ctgataacac ctcgcttgat gtcacagaca tctcactgga tatggatgac agtagcgaag   5220
gctcactttt ttcgagcttt agcggatcgg acaactctat tactagtatg gacagttggt   5280
cgtcaggacc tagttcacta gagatagtag accgaaggca ggtggtggtg gctgacgttc   5340
atgccgtcca agagcctgcc cctattccac cgccaaggct aaagaagatg gcccgcctgg   5400
```

```
cagcggcaag aaaagagccc actccaccgg caagcaatag ctctgagtcc ctccacctct   5460
cttttggtgg ggtatccatg tccctcggat caattttcga cggagagacg gcccgccagg   5520
cagcggtaca accccctggca acaggcccca cggatgtgcc tatgtctttc ggatcgtttt   5580
ccgacggaga gattgatgag ctgagccgca gagtaactga gtccgaaccc gtcctgtttg   5640
gatcatttga accgggcgaa gtgaactcaa ttatatcgtc ccgatcagcc gtatcttttc   5700
cactacgcaa gcagagacgt agacgcagga gcaggaggac tgaatactga ctaaccgggg   5760
taggtgggta catattttcg acggacacag gccctgggca cttgcaaaag aagtccgttc   5820
tgcagaacca gcttacagaa ccgaccttgg agcgcaatgt cctggaaaga attcatgccc   5880
cggtgctcga cacgtcgaaa gaggaacaac tcaaactcag gtaccagatg atgcccaccg   5940
aagccaacaa aagtaggtac cagtctcgta aagtagaaaa tcagaaagcc ataaccactg   6000
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact tggatatggt agacgggaca gtcgcctgcc   6240
tggatactgc aaccttctgc cccgctaagc ttagaagtta cccgaaaaaa catgagtata   6300
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgac attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
aagaagtgcc tatggataga ttcgtcatgg acatgaaaag agacgtgaaa gttacaccag   6660
gcacgaaaca cacagaagaa agaccgaaag tacaagtgat acaagccgca gaacccctgg   6720
cgactgctta cttatgcggg attcaccggg aattagtgcg taggcttacg gccgtcttgc   6780
ttccaaacat tcacacgctt tttgacatgt cggcggagga ttttgatgca atcatagcag   6840
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga aatccggaat gttcctcaca ctttttgtca   7080
acacagtttt gaatgtcgtt atcgccagca gagtactaga agagcggctt aaaacgtcca   7140
gatgtgcagc gttcattggc gacgacaaca tcatacatgg agtagtatct gacaaagaaa   7200
tggctgagag gtgcgccacc tggctcaaca tggaggttaa gatcatcgac gcagtcatcg   7260
gtgagagacc accttacttc tgcggcggat ttatcttgca agattcggtt acttccacag   7320
cgtgccgcgt ggcggatccc ctgaaaaggc tgtttaagtt gggtaaaccg ctcccagccg   7380
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt ttgcccagag caaaagagca ttccaagcca   7560
tcagagggga aataaagcat ctctacggtg gtcctaaata gtcagcatag tacatttcat   7620
ctgactaata ctacaacacc accacctcta gaatgatctg tagtgctaca gaaaaattgt   7680
gggtcacagt ctattatggg gtacctgtgt ggaaagaagc aaccaccact ctattttgtg   7740
```

```
catcagatgc taaagcatat gatacagagg tacataatgt ttgggccaca catgcctgtg   7800

tacccacaga ccccaaccca caagaagtag aattggaaaa tgtgacagaa aattttaaca   7860

tgtggaaaaa taacatggta gaacagatgc atgaggatat aatcagttta tgggatcaaa   7920

gcctaaagcc atgtgtaaaa ttaactccac tctgtgttac tttaaattgc actgatttga   7980

ggaatgctac taatgggaat gacactaata ccactagtag tagcagggaa atgatggggg   8040

gaggagaaat gaaaaattgc tctttcaaaa tcaccacaaa cataagaggt aaggtgcaga   8100

aagaatatgc actttttat aaacttgata tagtaccaat agataataat agtaataata   8160

gatataggtt gataagttgt aacacctcag tcattacaca ggcctgtcca aagatatcct   8220

ttgagccaat tcccatacat tattgtgccc cggctggttt tgcgattcta aagtgtaaag   8280

ataagaagtt caatggaaaa ggaccatgtt caaatgtcag cacagtacaa tgtacacatg   8340

ggattaggcc agtagtatca actcaactgc tgttaaatgg cagtctagca gaagaagagg   8400

tagtaattag atccgaaaat ttcgcggaca atgctaaaac cataatagta cagctgaatg   8460

aatctgtaga aattaattgt acaagaccca acaacaatac aagaaaaagt atacatatag   8520

gaccaggcag agcattatat acaacaggaa aaataatagg agatataaga caagcacatt   8580

gtaaccttag tagagcaaaa tggaatgaca ctttaaataa aatagttata aaattaagag   8640

aacaatttgg gaataaaaca atagtcttta agcattcctc aggaggggac ccagaaattg   8700

tgacgcacag ttttaattgt ggaggggaat tttctactg taattcaaca caactgttta   8760

atagtacttg gaatgttact gaagagtcaa ataacactgt agaaaataac acaatcacac   8820

tcccatgcag aataaaacaa attataaaca tgtggcagaa agtaggaaga gcaatgtatg   8880

cccctcccat cagaggacaa attagatgtt catcaaatat tacagggctg ctattaacaa   8940

gagatggtgg tccagaggac aacaagaccg aggtcttcag acctggagga ggagatatga   9000

gggacaattg gagaagtgaa ttatataaat ataaagtagt aaaaattgaa ccattaggag   9060

tagcacccac caaggcaaag agaagagtgg tgcagagaga aaaaagagca gtgggaatag   9120

gagctgtgtt ccttgggttc ttgggagcag caggaagcac tatgggcgca gctggcgcgc   9180

cacgtgacgc gtgcatgcat ttaaatatcg agggcaggag cgagagggcc aaggccaggg   9240

agggcggcca ccaccatcac caccatcacc attagtaatg aggtaaccgt ggggcccaat   9300

gatccgacca gcaaaactcg atgtacttcc gaggaactga tgtgcataat gcatcaggct   9360

ggtacattag atccccgctt accgcgggca atatagcaac actaaaaact cgatgtactt   9420

ccgaggaagc gcagtgcata atgctgcgca gtgttgccac ataaccacta tattaaccat   9480

ttatctagcg gacgccaaaa actcaatgta tttctgagga agcgtggtgc ataatgccac   9540

gcagcgtctg cataactttt attatttctt ttattaatca acaaaatttt gtttttaaca   9600

tttcaaaaaa aaaaaaaaaa aaaaaaaaaa aaaaaaaaaa agggaattcc tcgattaatt   9660

aagcggccgc                                                          9670
```

<210> SEQ ID NO 15
<211> LENGTH: 10272
<212> TYPE: DNA
<213> ORGANISM: Zika virus

<400> SEQUENCE: 15

```
atgaaaaacc ccaaagaaga aatccggagg atccggattg tcaatatgct aaaacgcgga     60

gtagcccgtg tgagcccctt tgggggcttg aagaggctgc cagccggact tctgctgggt    120

catgggccca tcaggatggt cttggcgata ctagcctttt tgagattcac ggcaatcaag    180
```

```
ccatcactgg gtctcatcaa tagatggggt tcagtgggga aaaaagaggc tatggaaata    240
ataaagaagt tcaagaaaga tctggctgcc atgctgagaa taatcaatgc taggaaggag    300
aagaagagac gaggcacaga tactagtgtc ggaattgttg gcctcctgct gaccacagcc    360
atggcagtgg aggtcactag acgtgggagt gcatactata tgtacttgga cagaagcgat    420
gctggggagg ccatatcttt tccaaccaca ctggggatga acaagtgtta catacagatc    480
atggatcttg gacacatgtg tgatgccacc atgagctatg aatgccctat gttggatgag    540
ggggtagaac cagatgacgt cgattgttgg tgcaacacga catcaacttg ggttgtgtac    600
ggaacctgcc accacaaaaa aggtgaagca cggagatcta gaagagctgt gacgctcccc    660
tcccattcca ctaggaagct gcaaacgcgg tcgcagacct ggttggaatc aagagaatat    720
acaaagcacc tgattagagt cgaaaattgg atattcagga accctggctt cgcgttagca    780
gcagctgcca tcgcctggct tttgggaagt tcaacgagcc aaaaagtcat atacttggtc    840
atgatactgc tgattgcccc ggcatacagc atcaggtgca taggagtcag caatagggac    900
tttgtggaag gtatgtcagg tgggacttgg gttgatgttg tcttggaaca tggaggttgt    960
gttaccgtaa tggcacagga caaaccggct gtcgacatag agctggttac aacaacagtc   1020
agcaacatgg cggaggtaag atcctattgc tatgaggcat caatatcgga catggcttcg   1080
gacagccgct gcccaacaca aggtgaagcc taccttgaca agcagtcaga cactcaatat   1140
gtctgcaaaa gaacgttagt ggacagaggc tggggaaatg gatgtggact tttggcaaa    1200
gggagcctgg tgacatgcgc taagtttgca tgctccaaga aaatgaccgg gaagagcatc   1260
cagccagaga atctggagta ccggataatg ctgtcagttc atggctccca gcacagtggg   1320
atgatcgtta atgacacagg acatgaaact gatgagaata gagcgaaggt tgagataacg   1380
cccaattcac caagagctga agccaccctg gggggttttg gaagcctagg acttgattgt   1440
gaaccgagga caggccttga cttttcagat ttgtattact tgactatgaa taacaagcac   1500
tggttggttc acaaggagtg gttccacgac attccattac cttggcatgc tggggcagac   1560
accggaactc cacattggaa caacaaagaa gcattggtag agttcaagga cgcacatgcc   1620
aaaaggcaaa ctgtcgtggt tctagggagt caagaaggag cagttcacac ggcccttgct   1680
ggagctctgg aggctgagat ggatggtgca aagggaaggc tgtcctctgg ccacttgaaa   1740
tgtcgcctga aaatggataa acttagattg aagggcgtgt catactcctt gtgtaccgca   1800
gcgttcacat tcaccaagat cccggctgaa acactgcacg ggacagtcac agtggaggta   1860
cagtacgcag ggacagatgg accctgcaag gttccagctc agatggcggt ggacatgcaa   1920
actctgaccc cagttgggag gctgataacc gctaaccctg taatcactga aagcactgag   1980
aactctaaga tgatgctgga acttgatcca ccatttgggg actcttacat tgtcatagga   2040
gtcggggaga agaagatcac ccatcactgg cacaggagtg gcagcaccat tggaaaagca   2100
tttgaagcca ctgtgagagg tgccaagaga atggcagtct tgggagacac agcctgggat   2160
tttggatcag ttggaggtgc tctcaactca ttgggcaagg gcatccatca aatttttgga   2220
gcagctttca aatcattgtt tggaggaatg tcctggttct cacaaattct cattggaacg   2280
ttgctggtgt ggttgggtct gaatacaaag aatggatcta tttcccttac gtgcttggcc   2340
ttagggggag tgttgatctt tttatccaca gccgtctctg ctgatgtggg gtgctcggtg   2400
gacttctcaa agaaggaaac gagatgcggt acgggggtgt tcgtctataa cgacgttgat   2460
gcctggaggg acaggtacaa gtaccatcct gactcccctc gtagattagc agcagcagtc   2520
```

-continued

```
aagcaagcct gggragatgg gatctgtggg atctcctctg tttcaagaat ggaaaacatc   2580
atgtggagat cagtagaagg ggagctcaac gcaatcctgg aagagaatgg agttcaactg   2640
acggtcgttg tgggatctgt aaaaaacccc atgtggagag gtccacagag attgcccgtg   2700
cctgtgaacg agctgcccca cggctggaag gcttgggga aatcgtactt cgtcagagca   2760
gcaaagacaa ataacagctt tgtcgtggat ggtgacacac tgaaggaatg cccactcaaa   2820
catagagcat ggaacagctt tcttgtggag gatcatgggt tcggggtatt tcacactagt   2880
gtctggctca aggttagaga agattattca ttagagtgtg atccagccgt tattggaaca   2940
gctgctaagg gaaaggaggc tgtgcacagt gatctaggct actggattga gagtgagaag   3000
aatgacacat ggaggctgaa gagggcccac ctgatcgaga tgaaaacatg tgaatggcca   3060
aagtcccaca cattgtggac agatggaata gaagaaagtg atctgatcat acccaagtct   3120
ttagctgggc cactcagcca tcacaacacc agagagggct acaggactca aatgaaaggg   3180
ccatggcaca gtgaagagct tgaaattcgg tttgaggaat gcccaggcac taaggtccac   3240
gtggaggaaa catgtggaac aagaggacca tctctgagat caaccactgc aagcggaagg   3300
gtgatcgagg aatggtgctg cagggaatgc acaatgcccc cactgtcgtt ccgggctaaa   3360
gatggctgtt ggtatggaat ggagataagg cccaggaaag aaccagaaag taacttagta   3420
aggtcaatgg tgactgcagg atcaactgat cacatggatc acttctccct tggagtgctt   3480
gtgattctgc tcatggtgca ggaagggctg aagaagagaa tgaccacaaa gatcatcata   3540
agcacatcaa tggcagtgct ggtagctatg atcctgggag gattttcaat gagtgacctg   3600
gccaagcttg caattttgat gggtgccacc tttgcggaaa tgaacactgg aggagatgta   3660
gctcatctgg cgctgatagc ggcattcaaa gtcagacctg cgttgctggt atctttcatc   3720
ttcagagcta attggacacc ccgtgagagc atgctgctgg ccctggcttc gtgtcttctg   3780
caaactgcga tctccgcctt ggaaggcgac ctgatggttc tcatcaatgg ttttgctttg   3840
gcctggttgg caatacgagc gatggttgtt ccacgcactg acaacatcac cttggcaatc   3900
ctgactgcgc tgacaccact ggcccggggc acgctgcttg tggcgtggag agcaggcctt   3960
gctacttgcg gggggttcat gcttctctct ctgaagggga agggcagtgt gaagaagaac   4020
ctaccatttg tcatggcctt gggactcacc gctgtgaggc tggtcgaccc catcaacgtg   4080
gtgggactgc tgttgctcac aaggagtggg aagcggagct ggccccctag tgaagtactc   4140
acagctgttg gtctgatatg cgcgttggcc ggagggttcg ccaaggcgga tatagagatg   4200
gctgggccca tggccgcggt cggtctgcta attgtcagtt acgtggtctc aggaaagagt   4260
gtggacatgt acattgaaag agcaggtgac atcacatggg aaaaagatgc ggaagtcact   4320
ggaaacagtc cccggctcga tgtggcactg gatgagagtg gtgatttctc cctagtggag   4380
gatgatggtc cccccatgag agagatcata ctcaaagtgg tcctgatgac catctgtggc   4440
atgaacccaa tagccatacc ctttgcagct ggagcgtggt acgtgtatgt gaagactgga   4500
aaaaggagtg gtgctctatg ggatgtgcct gctcccaagg aagtaaaaaa gggggagacc   4560
acagatggag tgtacagagt aatgactcgt agactgcttg gttcaacaca agttggagtg   4620
ggagtcatgc aagagggggt cttccacact atgtggcacg tcacaaaagg atccgcgctg   4680
agaagcggtg aagggagact tgatccatac tggggagatg tcaagcagga tctggtgtca   4740
tattgtggtc cgtggaagct agacgccgcc tgggacgggc acagcgaggt gcagctcttg   4800
gccgtgcccc ccggagagag agcgaggaac atccagactc cgcccggaat atttaagaca   4860
aaggatgggg acattggagc agttgcgttg gactacccag caggaacttc aggatctcca   4920
```

```
atcctagaca agtgtgggag agtgatagga ctctatggta atggggtcgt gataaaaaat   4980
gggagttatg ttagtgccat cacccaaggg aggagggagg aagagactcc tgttgagtgc   5040
ttcgagcctt cgatgttgaa gaagaagcag ctaactgtct tagacctgca tcctggagct   5100
gggaaaacca ggagagttct tcctgaaata gtccgtgaag ccataaaaac aagactccgt   5160
actgtgatct tagctccaac cagggttgtc gctgctgaaa tggaggaagc ccttagaggg   5220
cttccagtgc gttatatgac aacagcagtc aatgtcaccc attctgggac agaaattgtt   5280
gacttaatgt gccatgccac cttcacttca cgtctactac aaccaatcag agtccccaac   5340
tataatctgt atattatgga cgaggcccac ttcacagatc cctcaagtat agcagcaaga   5400
ggatacattt caacaagggt tgagatgggc gaggcggccg ccatcttcat gaccgccacc   5460
ccaccaggaa cccgtgacgc attcccggac tccaactcac caattatgga caccgaagtg   5520
gaagtcccag agagagcctg gagctcaggc tttgattggg tgacggatca ttctggaaaa   5580
acagtttggt ttgttccaag cgtgaggaac ggcaatgaga tcgcagcttg tctgacaaag   5640
gctggaaaac gggtcataca gctcagcaga aagacttttg agacagagtt cctgaaaaca   5700
aaaaatcaag agtgggactt cgtcgtgaca actgacattt cagagatggg cgccaacttt   5760
aaagctgacc gtgtcataga ttccaggaga tgcctaaagc cggtcatact tgatggcgag   5820
agagtcattc tggctggacc catgcctgtc acacatgcca gcgctgccca gaggaggggg   5880
cgcataggca ggaatcccaa caaacctgga gatgagtatc tgtatggagg tgggtgcgca   5940
gagactgatg aagaccatgc acactggctt gaagcaagaa tgcttcttga caacatttac   6000
ctccaagatg gcctcatagc ctcgctctat cgacctgagg ccgacaaagt agcagctatt   6060
gagggagagt tcaagcttag gacggagcaa aggaagacct ttgtggaact catgaaaaga   6120
ggagatcttc ctgtttggct ggcctatcag gttgcatctg ccggaataac ctacacagat   6180
agaaaatggt gctttgatgg cacgaccaac aacaccataa tggaagacag tgtgccggca   6240
gaggtgtgga ccagatacgg agagaaaaga gtgctcaaac caaggtggat ggacgccaga   6300
gtttgttcag atcatgcggc cctgaagtca ttcaaagagt ttgccgctgg gaaaagagga   6360
gyggcctttg gagtgatgga agccctggga acattgccgg gacacatgac agagagattc   6420
caggaagcca ttgacaacct cgctgtgctc atgcgggcag agactggaag caggccttac   6480
gaagccgcgg cggcccaatt gccggagacc ttagagacca tcatgctttt ggggttgctg   6540
ggaacagtct cgctgggaat ctttttcgtc ttgatgcgga ataagggcat cgggaagatg   6600
ggctttggaa tggtgactct tggggccagc gcatggctta tgtggctctc ggaaattgag   6660
ccagccagaa ttgcatgtgt cctcattgtt gtgttcctat tgctggtggt gctcatacct   6720
gagccagaaa agcaaagatc tccccaggac aaccaaatgg caatcatcat catgatagca   6780
gtgggtcttc tgggtttgat taccgccaat gaacttggat ggttggaaag aacaaagagt   6840
gacctaagcc atctaatggg aaggagagag gagggggcaa ccataggatt ctcaatggac   6900
attgacctgc ggccagcctc agcttgggct atctatgctg ctctgacaac tttcatcacc   6960
ccagccgtcc aacatgcggt gaccacttca tacaacaact actccttaat ggcgatggcc   7020
acgcaagctg gagtgttgtt tggtatgggt aaagggatgc cattctacgc atgggacttt   7080
ggagtcccgc tgctaatgat gggttgctac tcacaattaa cacccctgac cctaatagtg   7140
gccatcattt tgctcgtggc gcactacatg tacttgatcc cagggctgca ggcagcagct   7200
gcgcgtgctg cccagaagag aacggcagct ggcatcatga agaaccctgt tgtggatgga   7260
```

```
atagtggtga ctgacattga cacaatgaca attgaccacc gagtggagaa aaagatggga   7320
caggtgctac tcatagcagt agccgtctcc agcgccatac tgtcgcggac cgcctggggg   7380
tggggggagg ctggggccct gatcacagct gcaacttcca ctttgtggga aggctctccg   7440
aacaagtact ggaactcctc cacagccact tcactgtgta acatttttag ggaagttac    7500
ttggctggag cttctctaat ctacacagta acaagaaacg ctggcttggt caagagacgt   7560
gggggtggaa cgggagagac cctgggagag aaatggaagg cccgcctgaa ccagatgtcg   7620
gccctagagt tctactccta caaaaagtca ggcatcaccg aggtgtgcag agaagaggcc   7680
cgccgcgccc tcaaggacgg tgtggcaaca ggaggccatg ctgtgtcccg aggaagtgca   7740
aagcttagat ggttggtgga gagaggatac ctgcagccct atggaaaggt cattgatctt   7800
ggatgtggca gagggggctg gagttactac gccgccacca tccgcaaagt tcaagaagtg   7860
aaaggataca caaaaggagg ccctggtcat gaagaaccca tgttggtgca aagctatggg   7920
tggaacatag tccgtcttaa gagtggggtg gacgtctttc atatggcggc tgagccgtgt   7980
gacactttgc tgtgtgatat aggtgagtca tcatctagtc ctgaagtgga agaagcacgg   8040
acgctcagag tcctttccat ggtgggggat tggcttgaaa aaagaccagg agccttttgt   8100
ataaaagtgt tgtgcccata caccagcact atgatggaaa ccctggagcg actgcagcgt   8160
aggtatgggg gaggactggt cagagtgcca ctctcccgca actctacaca tgagatgtac   8220
tgggtctctg gagcgaaaag caacaccata aaaagtgtgt ccaccacgag ccagctcctc   8280
ttggggcgca tggacgggcc caggaggcca gtgaaatatg aggaggatgt gaatctcggc   8340
tccggcacgc gggctgtggt aagctgcgct gaagctccca acatgaagat cattggtaac   8400
cgcattgaga ggatccgcag tgagcacgcg gaaacgtggt tctttgacga gaaccaccca   8460
tataggacat gggcttacca tggaagctat gaggccccta cacaagggtc agcgtcctct   8520
ctaataaacg gggttgtcag gctcctgtca aaaccctggg atgtggtgac tggagtcaca   8580
ggaatagcca tgaccgacac cacaccgtat ggtcagcaaa gagttttcaa ggaaaaagtg   8640
gacactaggg tgccagaccc ccaagaaggc actcgtcagg ttatgagcat ggtctcttcc   8700
tggttatgga aagagctagg caaacacaaa cggccacgag tctgtaccaa agaagagttc   8760
atcaacaagg ttcgtagcaa tgcagcatta ggggcaatat ttgaagagga aaaagagtgg   8820
aagactgcag tggaagctgt gaacgatcca aggttctggg ctctagtgga caaggaaaga   8880
gagcaccacc tgagaggaga gtgtcagagc tgtgtgtaca acatgatggg aaaaagagaa   8940
aagaaacaag gggaatttgg aaaggccaag ggcagccgcg ccatctggta tatgtggcta   9000
ggggctagat tcctggagtt cgaagccctt ggattcttga acgaggatca ctggatgggg   9060
agagagaatt caggaggtgg tgttgaaggg ctgggattac aaagactcgg atatgtccta   9120
gaagagatga gtcgcatacc aggaggaagg atgtatgctg atgacacagc tggctgggac   9180
acccgcatca gcaggtttga tctggagaat gaagctctaa tcaccaacca aatggagaaa   9240
gggcacaggg ccttggcatt ggccataatc aagtacacat accaaaacaa agtggtaaag   9300
gtcctcagac cagctgaaaa agggaagaca gttatggaca ttatttcaag acaagaccaa   9360
agggggagcg gacaagttgt cacttacgct cttaatacat tcaccaacct ggtggtgcag   9420
ctcattcgga atatggaggc tgaggaagtt ctagagatgc aagacttgtg gctgctgcgg   9480
aggtcagaga aagtgaccaa ctggttgcag agcaacggat gggataggct caaacgaatg   9540
gcagtcagtg gagatgattg cgttgtgaaa ccaattgatg ataggtttgc acatgccctc   9600
aggttcttga atgatatggg aaaagtcagg aaggacacac aagagtggaa accctcaact   9660
```

-continued

```
ggatgggaca attgggaaga agttccgttt tgctcccacc acttcaacaa gctccatctc   9720

aaggacggga ggtccattgt ggttccctgc cgccaccaag atgaactgat tggccgagcc   9780

cgcgtctcac caggggcggg atggagcatc cgggagactg cttgcctagc aaaatcatat   9840

gcgcaaatgt ggcagctcct ttatttccac agaagggacc tccgactgat ggccaatgcc   9900

atttgttcat ctgtgccagt tgactgggtt ccaactggga gaactacctg gtcaatccat   9960

ggaaagggag aatggatgac cactgaagac atgcttgtgg tgtggaacag agtgtggatt  10020

gaggagaacg accacatgga agacaagacc ccagttacga aatggacaga cattccctat  10080

ttgggaaaaa gggaagactt gtggtgtgga tctctcatag ggcacagacc gcgcactacc  10140

tgggctgaga acatcaaaaa cacagtcaac atgatgcgca ggatcatagg tgatgaagaa  10200

aagtacatgg actacctatc cacccaagtt cgctacttgg gtgaagaagg gtccacaccc  10260

ggagtgttgt aa                                                      10272


<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 16

His His His His His His His His
1               5
```

SINDBIS CONTROL VIRUS

PRIORITY CLAIM

This application is a divisional of U.S. patent application Ser. No. 15/737,818, filed Dec. 19, 2017; which is the U.S. National Stage Application of PCT/US16/035751, filed Jun. 3, 2016; which claims the benefit of priority to U.S. Provisional Patent Application No. 62/182,104, filed Jun. 19, 2015.

SEQUENCE LISTING

The instant application contains a Sequence Listing which has been submitted electronically in ASCII format and is hereby incorporated by reference in its entirety. Said ASCII copy, created on May 31, 2016, is named SCX_00325_SL.txt and is 144,758 bytes in size.

BACKGROUND

Regulatory agencies, such as the FDA, CLIA and CAP, generally require developers of nucleic acid-based in vitro diagnostic devices for pathogen detection to include quality controls in their regulatory submissions. Such quality control materials are important tools for the detection of analytical errors, the monitoring of long-term performance of diagnostic test kits, and the identification of changes in random or systematic error. A well-designed laboratory quality control program will generally incorporate at least some form of control that provides added confidence in the reliability of results obtained for unknown specimens.

Whole process controls are needed to monitor the entire analytical process, including sample lysis, nucleic acid extraction, amplification, detection and interpretation of results. Such controls can be natural material derived from infected patients, which have the advantage of behaving very similarly to a clinical sample. However, such natural source controls often have limited and unpredictable availability, concentration and stability. The use of cultured virus to generate positive controls alleviates some of these problems, but virus culture is often unavailable or technologically difficult. In addition, the preparation of large amount of human pathogens caries significant safety risks and is expensive.

Positive controls for amplification and detection are often provided as part of diagnostic test kits. The materials often have a known amount of input copy number and verify the integrity of the reaction components and instrument. However, such controls are not usually taken through the sample lysis or nucleic acid extraction process and are therefore unable to detect errors arising from these steps. Examples of this type of control include a non-infectious DNA plasmid containing the target sequence, purified RNA transcripts, or packaged RNA materials such as Armored RNA. These materials often also suffer from their limited stability at ambient temperatures.

Internal controls contain a non-target nucleotide sequence that is co-extracted and co-amplified with the target nucleic acid. Internal controls confirm the integrity of the reagents (e.g., polymerase, primers, etc.), equipment function (e.g., thermal cycler), and the absence of inhibitors in the sample. The internal control can take the form of a non-target organism that is added to the sample prior to sample lysis and extraction. Alternatively, it could be a non-infectious, non-target DNA or RNA sequence that is added to the sample either prior to or after sample lysis and extraction.

Thus, there is a need for improved compositions able to serve as controls in diagnostic assays.

SUMMARY

Provided herein are compositions and methods related to replication deficient Sindbis viruses that are able to function as controls for nucleic acid diagnostic assays (e.g., nucleic acid sequencing based assays and/or nucleic acid amplification based assays).

In certain aspects, disclosed herein is a replication deficient recombinant Sindbis virus comprising a RNA genome comprising (a) an open reading frame (ORF) encoding functional Sindbis non-structural proteins and (b) a heterologous (i.e., non-Sindbis) RNA sequence. In some embodiments, the ORF encoding the functional Sindbis non-structural proteins is located 5' of the heterologous RNA sequence.

In some embodiments, the ORF encoding the Sindbis non-structural proteins encodes a nsP1 protein, a nsP2 protein, a nsP3 protein and a nsP4 protein. In some embodiments, the ORF encoding Sindbis non-structural proteins has a nucleotide sequence that is at least 80%, at least 85%, at least 90%, at least 91%, at least 92%, at least 93%, at least 94%, at least 95%, at least 96%, at least 97%, at least 98%, at least 99% or 100% identical to nucleotides 1-7648 of SEQ ID NO: 1. These nucleotides encode non-structural Sindbis proteins.

In some embodiments, the RNA genome of the replication deficient Sindbis virus lacks a sequence encoding a functional version of one or more of the Sindbis structural proteins (e.g., Sindbis capsid protein, E3 protein, E2 protein, 6k protein and/or E1 protein). In some embodiments, the RNA genome lacks an RNA sequence encoding any functional Sindbis structural proteins. In some embodiments, the heterologous RNA sequence replaces the ORF encoding the Sindbis structural proteins in the RNA genome.

In some embodiments, the replication deficient recombinant Sindbis virus of claim any one of claims 1 to 8, wherein the RNA genome comprises a 26S subgenomic promoter at the 3' end of the ORF encoding the Sindbis non-structural proteins.

In some embodiments, the heterologous RNA sequence in the RNA genome comprises a non-Sindbis RNA virus sequence or a retrovirus sequence. In some embodiments, the heterologous RNA sequence includes at least 10, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900 or 2000 bp of a non-Sindbis RNA virus sequence or a retrovirus sequence. In some embodiments, the heterologous RNA sequence includes 100-300 bp of a non-Sindbis RNA virus sequence or a retrovirus sequence. In some embodiments, the heterologous RNA sequence includes 100-200 bp of a non-Sindbis RNA virus sequence or a retrovirus sequence. In some embodiments, the heterologous RNA sequence is at least 80%, at least 85%, at least 90%, at least 91%, at least 92%, at least 93%, at least 94%, at least 95%, at least 96%, at least 97%, at least 98%, at least 99% or 100% identical to a non-Sindbis RNA virus sequence or a retrovirus sequence. In some embodiments, the non-Sindbis RNA virus sequence or retrovirus sequence comprises one or more mutations that convey a drug resistant phenotype when present in the non-Sindbis RNA virus or the retrovirus. For example, in some embodiments the non-Sindbis RNA virus sequence or retrovirus sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29 or 30 mutations that convey a drug resistant phenotype when present in the non-Sindbis RNA virus or the retrovirus.

In some embodiments, the heterologous RNA sequence comprises a non-Sindbis RNA virus sequence. In some embodiments, the non-Sindbis RNA virus sequence is an Ebolavirus sequence, an influenza virus sequence, a SARS virus sequence, a hepatitis C virus sequence, a West Nile virus sequence, a Zika virus sequence, a poliovirus sequence or a measles virus sequence.

In some embodiments, the non-Sindbis RNA virus sequence is an Ebolavirus sequence (e.g., a Zaire ebolavirus sequence, a Bundibugyo ebolavirus sequence, a Reston ebolavirus sequence, a Sudan ebolavirus sequence or a Tai Forest ebolavirus sequence). In some embodiments, the Ebolavirus sequence comprises at least a portion of an Ebolavirus GP gene sequence, an Ebolavirus NP gene sequence or an Ebolavirus VP24 gene sequence. In some embodiments, the heterologous RNA sequence does not encode a functional Ebola protein (e.g., the heterologous RNA sequence encodes truncated Ebola proteins, Ebola proteins with frame-shift mutations and/or Ebola protein sequences lacking a start codon). In some embodiments, the heterologous RNA sequence comprises a sequence at least 80%, at least 85%, at least 90%, at least 91%, at least 92%, at least 93%, at least 94%, at least 95%, at least 96%, at least 97%, at least 98%, at least 99% or 100% identical to SEQ ID NO: 2 or SEQ ID NO: 3. SEQ ID NO: 2 is the nucleotide sequence of a GP Ebola target sequence used in an exemplary Ebola Sindbis control virus described in Example 1. SEQ ID NO: 3 is the nucleotide sequence of a NP/VP24 Ebola target sequence used in an exemplary Ebola Sindbis control virus described in Example 1. The portion of the Ebola NP gene consists of nucleotides 1 to 1577 of SEQ ID NO: 3, the portion of the Ebola VP24 gene consists of nucleotides 1578 to 2127 and the sequence of the human RNAse P internal control consists of nucleotides 2128 to 2217.

In some-embodiments, the heterologous RNA sequence comprises a retrovirus sequence. In some embodiments, the retrovirus sequence is an HIV-1 sequence, an HIV-2 sequence, an HTLV-I sequence, or an HTLV-II sequence.

In some embodiments, the heterologous RNA sequence comprises an HIV-1 sequence. In some embodiments, the HIV-I sequence comprises one or more mutations that, when present in a HIV-1 virus, conveys a drug resistance phenotype (e.g., resistance to a protease inhibitor, a nucleoside analogue reverse transcriptase inhibitor and/or a non-nucleoside analog reverse transcriptase inhibitor). For example, in some embodiments the HIV-1 virus sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29 or 30 mutations that convey a drug resistant phenotype. In some embodiments, the one or more mutations, when present in HIV-1 virus, convey resistance to a drug selected from the group consisting of: atazanavir, ritonavir, darunavir, fosamprenavir, indinavir, lopinavir, nelfinavir, saquinavir, tipranavir, abacavir, didanosine, emtricitabine, lamivudine, stavudine, tenofovir, zidovudine, efavirenz, etavirine, nevirapine or rilpivirine. In some embodiments, the one or more mutations are selected from the group consisting of L24I, D30N, V32I, M46I, I47V, G48V, 150V, 154M, G73S, L76V, V82A, 184V, N88D, L90M, M41L, K65R, D67N, T69S insert SS, K70R, L74V, F77L, Y115F, F116Y, Q151M, M184V. L210W, T215Y, K219Q, L100I KI01E, K103N, V106A, V1081, Y181C, Y188L. G190A, P225H and M230L. In some embodiments, the one or more mutations are selected from the group consisting of L24I (TTA to ATA), D30N (GAT to AAT), V32I (GTA to ATA), M46I (ATG to ATA), I47V (ATA to CTA), G48V (GGG to GTG), 150V (ATT to GTT), 154M (ATC to ATG), G73S(GGT to GCT), L76V (TTA to GTA), V82A (GTC to GCC), I84V (ATA to GTA), N88D (AAT to GAT), L90M (TTG to ATG), M41L (ATG to TTG), K65R (AAA to AGA), D67N (GAC to AAC), T69S insert SS (ACT to TCT and insertion of TCC and TCC), K70R (AAA to AGA), L74V (TTA to GTA), F77L (TTC to CTC), Y115F (TAT to TTr), F116Y (TTT to TAT), Q511M (CAG to ATG), M184V (ATG to GTG), L210W (TTG to TGG), T215Y (ACC to TAC), K219Q (AAA to CAA). L100I (TTA to ATA), K101E (AAA to GAA), K103N (AAA to AAC), V106A (GTA to GCA), V1081 (GTA to ATA), Y181C (TAT to TGT), Y188L (TAT to TTA), G190A (GGA to GCA), P225H (CCT to CAT) and M230L (CCT to CAT). In some embodiments, the HIV-1 sequence comprises at least a portion of an HIV-1 gene selected from p7, p1, p6, HIV protease, reverse transcriptase, p51 RNAse, integrase and gp120. In some embodiments, the HIV-1 sequence comprises at least a portion of p7, p1, p6, HIV protease, reverse transcriptase and integrase. In certain embodiments, the HIV-1 sequence comprises at least a portion of 6p120, wherein the portion comprises the V1-V5 variable loops. In some embodiments, the HIV-1 sequence comprises a sequence that is at least 80%, at least 85%, at least 90%, at least 91%, at least 92%, at least 93%, at least 94%, at least 95%, at least 96%, at least 97%, at least 98%, at least 99% or 100% identical to nucleotides 1900 through 5400 and/or 63 (0 through 7825 of the HXB2 strain of HIV-1 (SEQ ID NO: 4). SEQ ID NO: 4 is the nucleotide sequence of the HIV-1 HXB2 genome. In some embodiments, the HIV-1 sequence is identical to nucleotides 1900 through 5400 and/or 6300 through 7825 of the HXB2 strain of HIV-I (SEQ ID NO: 4) except for the presence of the mutations that convey a drug resistance phenotype.

In some embodiments, the heterologous RNA sequence comprises a sequence at least 80%, at least 85%, at least 90%, at least 91%, at least 92%, at least 93%, at least 94%, at least 95%, at least 96%, at least 97%, at least 98%, at least 99% or 100% identical to SEQ ID NO. 5 and/or SEQ ID NO: 7. SEQ ID NO: 5 is the nucleotide sequence of a 5' multi-mutant HIV-1 target sequence comprising a number of drug resistance mutations, used in an exemplary multi-mutant HIV-1 control virus described in Example 2. SEQ ID NO: 7 is the nucleotide sequence of a 3' mutant HIV-1 target sequence used in an exemplary multi-mutant HIV-1 control virus described in Example 2.

In some embodiments, the heterologous RNA sequence comprises a sequence at least 80%, at least 85%, at least 90%, at least 91%, at least 92%, at least 93%, at least 94%, at least 95%, at least 96%, at least 97%, at least 98%, at least 99% or 100% identical to SEQ ID NO: 6 and/or SEQ ID NO: 8. SEQ ID NO: 6 is the nucleotide sequence of a 5' wild-type HIV-1 target sequence in an exemplary HIV-1 control virus, described in Example 2. SEQ ID NO: 8 is the nucleotide sequence of a 3' wild-type HIV-1 target sequence used in an exemplary HIV-1 control virus, described in Example 2.

In some embodiments, the heterologous RNA sequence comprises a sequence that is at least 80%, at least 85%, at least 90%, at least 91%, at least 92%, at least 93%, at least 94%, at least 95%, at least 96%, at least 97%, at least 98%, at least 99% or 100% identical to either nucleotides 1-3446, nucleotides 3294-5575, nucleotides 5425-7722, or nucleotides 7542-10272 of SEQ ID NO: 15.

In some embodiments, the RNA genome of the replication deficient Sindbis virus comprises a nucleotide sequence that is at least 80%, at least 85%, at least 90%, at least 91%, at least 92%, at least 93%, at least 94%, at least 95%, at least 96%, at least 97%, at least 98%, at least 99% or 100% identical to SEQ ID NO: 9, SEQ ID NO: 10, SEQ ID NO: 11, SEQ ID NO: 12, SEQ ID NO: 13, SEQ ID NO: 14, or SEQ ID NO: 15.

In certain aspects, provided herein is a composition comprising a replication deficient Sindbis virus described herein. In certain aspects, the composition comprises two or more of the replication deficient Sindbis viruses described herein. For example, in some embodiments, the composition comprises a replication deficient Sindbis virus comprising a RNA genome comprising a sequence that is at least 80%, at least 85%, at least 90%, at least 91%, at least 92%, at least 93%, at least 94%, at least 95%, at least 96%, at least 97%, at least 98%, at least 99% or 100% identical to SEQ ID NO: 11 and a replication deficient Sindbis virus comprising a RNA genome comprising a sequence that is at least 80%, at least 85%, at least 90%, at least 91%, at least 92%, at least 93%, at least 94%, at least 95%, at least 96%, at least 97%, at least 98%, at least 99% or 100% identical to SEQ ID NO: 13. In some embodiments, the composition comprises a replication deficient Sindbis virus comprising a RNA genome comprising a sequence that is at least 80%, at least 85%, at least 90%, at least 91%, at least 92%, at least 93%, at least 94%, at least 95%, at least 96%, at least 97%, at least 98%, at least 99% or 100% identical to SEQ ID NO: 12 and a replication deficient Sindbis virus comprising a RNA genome comprising a sequence that is at least 80%, at least 85%, at least 90%, at least 91%, at least 92%, at least 93%, at least 94%, at least 95%, at least 96%, at least 97%, at least 98%, at least 99% or 100% identical to SEQ ID NO: 14. In some embodiments, the composition further comprises human DNA. In some embodiments, the replication deficient Sindbis virus is in a human bodily fluid. In some embodiments, the human bodily fluid is human plasma (e.g., defibrinated human plasma). In some embodiments, the composition further comprises a preservative, such as sodium azide.

In some embodiments, the composition comprises a replication deficient Sindbis virus comprising a RNA genome comprising a sequence that is at least 80%, at least 85%, at least 90%, at least 91%, at least 92%, at least 93%, at least 94%, at least 95%, at least 96%, at least 97%, at least 98%, at least 99% or 100% identical to either nucleotides 1-3446, nucleotides 3294-5575, nucleotides 5425-7722, or nucleotides 7542-10272 of SEQ ID NO: 15.

In certain aspects, provided herein is a nucleic acid molecule encoding the RNA genome of the replication deficient Sindbis virus described herein. In some embodiments, the nucleic acid molecule is a DNA molecule. In some embodiments, the nucleic acid molecule is an RNA molecule. In some embodiments, the nucleic acid molecule is a plasmid (e.g., a circular plasmid or a linearized plasmid, such as a circular expression plasmid or a linearized expression plasmid). In some embodiments, the nucleic acid molecule is isolated. In certain embodiments, provided herein is a cell comprising a nucleic acid described herein. In some embodiments, the cell is a BHK cell.

In certain aspects, provided herein is a method of making a replication deficient Sindbis virus. In certain embodiments, the method includes the step of transfecting a cell (e.g., a BHK cell) with a nucleic acid molecule (e.g., an RNA molecule) encoding the RNA genome of a replication deficient Sindbis virus described herein and with a nucleic acid (e.g., an RNA molecule) encoding functional Sindbis structural proteins. In some embodiments, the cell is then cultured under conditions such that the cell produces the replication deficient Sindbis virus into the culture medium. In some embodiments, the method further comprises collecting the replication deficient Sindbis virus (e.g., by collecting the culture supernatant). In some embodiments, the method further comprises filtering and/or heat inactivating the culture supernatant. In some embodiments, the method further comprises determining the titer of the virus (e.g., using real-time PCR).

In certain aspects, provided herein are methods of testing a diagnostic assay by running the diagnostic assay on a composition comprising the replication deficient Sindbis virus described herein. In some embodiments, the diagnostic assay is a nucleic acid amplification based diagnostic assay. In some embodiments, the diagnostic assay is a sequencing based diagnostic assay. In some embodiments the diagnostic assay is an assay for the detection of a RNA virus and/or a retrovirus. In some embodiments, the diagnostic assay is an assay for the detection of Ebolavirus, an influenza virus, a SARS virus, a hepatitis C virus, a West Nile virus, a Zika virus, a poliovirus, a measles virus, an HIV-1 virus, an HIV-2 virus, an HTLV-I virus and/or an HTLV-II virus. In certain embodiments, the heterologous RNA sequence in the RNA genome of the replication deficient Sindbis virus contains the target sequence detected in the diagnostic assay. In some embodiments, the method includes the performance of a sample lysis step on the composition comprising the replication deficient Sindbis virus. In some embodiments, the method comprises performing a nucleic acid extraction step. In some embodiments, the method comprises performing a nucleic acid amplification step (e.g., performing a real-time nucleic acid amplification/detection process). In some embodiments, the method comprises performing a nucleic acid sequencing step. In some embodiments the method comprises performing a nucleic acid detection step.

BRIEF DESCRIPTION OF FIGURES

FIG. 10A depicts nucleotides 1 to 3446 of the Zika virus from GenBank Accession number EU545988.1, referred to as the "Zika Env Construct," which includes the NS1 gene. This portion of the Zika virus genome was integrated into a Zika virus reference material.

FIG. 10B depicts of nucleotides 3294 to 5575 of the Zika virus from GenBank Accession number EU545988.1, referred to as the "Zika NS2/NS3 Construct," which includes the NS2 and NS3 genes as well as a portion of the NS1 gene. This portion of the Zika virus genome was integrated into a Zika virus reference material.

FIG. 10C depicts nucleotides 5425 to 7722 of the Zika virus from GenBank Accession number EU545988.1, referred to as the "Zika NS4 Construct," which includes the NS4A and NS4B genes as well as a portion of the NS3 gene. This portion of the Zika virus genome was integrated into a Zika virus reference material.

FIG. 10D depicts nucleotides 7542 to 10272 of the Zika virus from GenBank Accession number EU545988.1, referred to as the "Zika NS5 Construct," which includes the NS5 gene and a portion of the NS4B gene. This portion of the Zika virus genome was integrated into a Zika virus reference material.

FIG. 12 shows stability results of TaqMan real time quantitation of a H7N9 influenza reference material stored at ambient temperature for seventeen months. Each error bar corresponds to 1 standard deviation from the mean.

DETAILED DESCRIPTION

General

Figure 1:
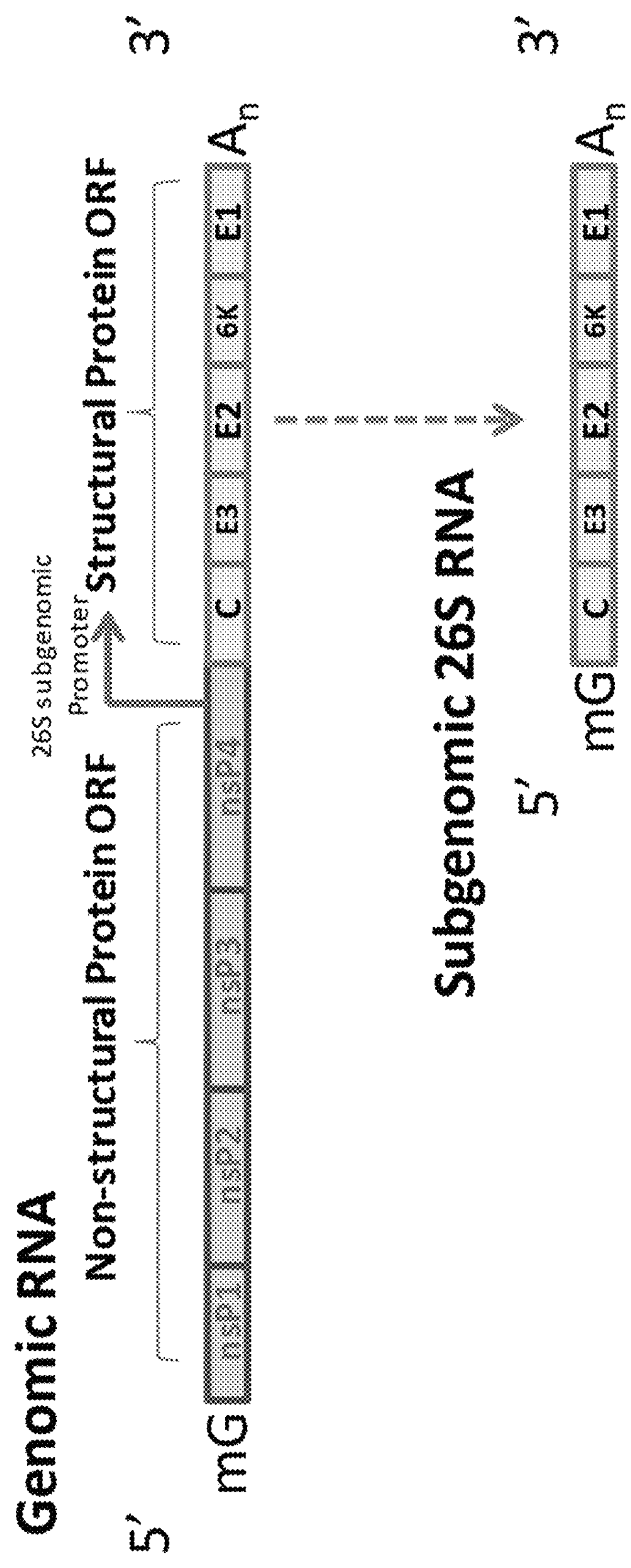
FIG. 1 shows a schematic depiction of the genomic organization of Sindbis virus. Some of the genes shown encode nonstructural proteins (nsP1-4), which include the helicase and RNA polymerase. Some of the genes are the structural genes, and encode the capsid (C) as well as proteins involved in budding.

Provided herein are compositions and methods related to replication deficient Sindbis viruses that are able to function as controls for nucleic acid diagnostic assays (e.g., nucleic acid sequencing based assays and/or nucleic acid amplification based assays). In certain aspects, provided herein are Sindbis control virus are useful as whole process controls, positive controls and/or internal controls in nucleic acid diagnostic assays. Such control virus can benefit diagnostics manufacturers by providing a less expensive, consistent and safe source of starting material for controls. The control virus described herein use Sindbis virus, an RNA containing enveloped virus which can be engineered to contain target RNA sequences such as sequences from another virus and/or an internal control sequence. The Sindbis virus coat provides the RNA genome with improved stability. In some embodiments, the recombinant Sindbis virus system described herein results in viral particles that are packaged, so they can be used to evaluate nucleic acid extraction processes that are used before nucleic acid detection. Also provided herein are compositions comprising such viruses, nucleic acid molecules encoding the RNA genome of such control viruses, methods of making such control viruses and methods of using such control viruses.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "biological sample,"-tissue sample," or simply "sample" each refers to a collection of cells obtained from a tissue of a subject. The source of the tissue sample may be solid tissue, as from a fresh, frozen and/or preserved organ, tissue sample, biopsy, or aspirate; blood or any blood constituents, serum, blood; bodily fluids such as cerebral spinal fluid, amniotic fluid, peritoneal fluid or interstitial fluid, urine, saliva, stool, tears; or cells from any time in gestation or development of the subject.

The term "control" includes any portion of an experimental system designed to demonstrate that the factor being tested is responsible for the observed effect, and is therefore useful to isolate and quantify the effect of one variable on a system.

The term "gene" is used broadly to refer to any nucleic acid associated with a biological function. The term "gene" applies to a specific genomic sequence, as well as to a cDNA or an mRNA encoded by that genomic sequence.

As used herein, the term "heterologous RNA" refers to RNA present in a recombinant Sindbis virus that is not derived from wild-type Sindbis virus. For example, heterologous RNA in a Sindbis virus can be an RNA sequence normally found in a different virus (e.g. a different RNA virus or retrovirus), can be an RNA sequence normally found a non-viral organism, or can be a completely artificial RNA sequence.

The term "isolated nucleic acid" refers to a polynucleotide of natural or synthetic origin or some combination thereof, which (1) is not associated with the cell in which the "isolated nucleic acid" is found in nature, and/or (2) is operably linked to a polynucleotide to which it is not linked in nature.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides, coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleotide sequences provided herein, U nucleotides are interchangeable with T nucleotides.

As used herein, the term "Sindbis virus" includes viral particles made up of an icosahedral capsid that comprises Sindbis virus capsid, E1 and E2 proteins encompassing a single-stranded RNA genome. The RNA genome can include non-Sindbis RNA (i.e., heterologous RNA) and does not need to include all parts of the wild-type Sindbis genome. For example, in some embodiments the RNA genome does not encode one or more of the Sindbis structural proteins.

Replication Deficient Sindbis Control Viruses

In certain embodiments, provided herein are replication deficient Sindbis control viruses. In some embodiments, such viruses have an RNA genome that includes (a) an open reading frame (ORF) encoding functional Sindbis non-structural proteins and (b) a heterologous (i.e., non-Sindbis) RNA sequence. In some embodiments, the ORF encoding the functional Sindbis non-structural proteins is located 5' of the heterologous RNA sequence. In some embodiments, the heterologous RNA sequence is a sequence from a different RNA virus (e.g., an Ebolavirus sequence, an influenza virus sequence, a SARS virus sequence, a hepatitis C virus sequence, a West Nile virus sequence, a Zika virus sequence, a poliovirus sequence or a measles virus sequence) or a sequence from a retrovirus (e.g., an HIV-1 sequence, an HIV-2 sequence, an HTLV-I sequence, or an HTLV-II sequence).

Wild-type Sindbis virus is a member of Alphavirus genus, family Togaviridae. The viral genome is approximately 11,700 nucleotides. As such, Sindbis virus has approximately the same genomic complexity as many human pathogenic viruses, including, for example, HIV-1 (9270 nucleotides), HCV (9700 nucleotides) and Ebola Zaire (18959 nucleotides). This offers a technical advantage over certain other technologies used to package RNA controls, such as Armored RNA, which are based on MS2 bacteriophage technology and produce recombinant RNA molecules as small as 900 bases in length, which in many instances does adequately reflect the complexity or RNA secondary structure of the pathogenic viruses found in patient samples.

As depicted in FIG. 1, wild-type Sindbis virus contains a single-stranded positive sense genomic RNA which encodes both viral structural proteins (for capsid assembly and viral budding) as well as the nonstructural proteins (such as the replication enzymes). Upon entry of the virus into a cell, the RNA is released into cytoplasm and drives production of the viral replicase proteins (non-structural proteins 1-4). These proteins form replication and transcription complexes and are responsible for generating the negative strand of the genomic RNA. Promoters in the negative strand genomic RNA drive transcription of two mRNA species: The full-length genomic RNA encodes the nonstructural proteins and the smaller subgenomic RNA encodes the structural proteins. The 5' ends of both transcripts are capped with 7-methylguanosine and the 3' ends are polyadenylated.

In certain embodiments, the recombinant Sindbis control viruses described herein are replication deficient. In some embodiments, any method can be used to render the recombinant Sindbis control virus replication deficient. For example, in some embodiments the Sindbis control virus does not encode one or more functional structural proteins. For example, in some embodiments, the In some embodiments the recombinant Sindbis control virus genome does not encode one or more functional nonstructural proteins. In some embodiments, the Sindbis control virus does not encode a functional nsP1 protein, a functional nsP2 protein, a functional nsP3 protein and/or a functional nsP4 protein.

Figure 2:
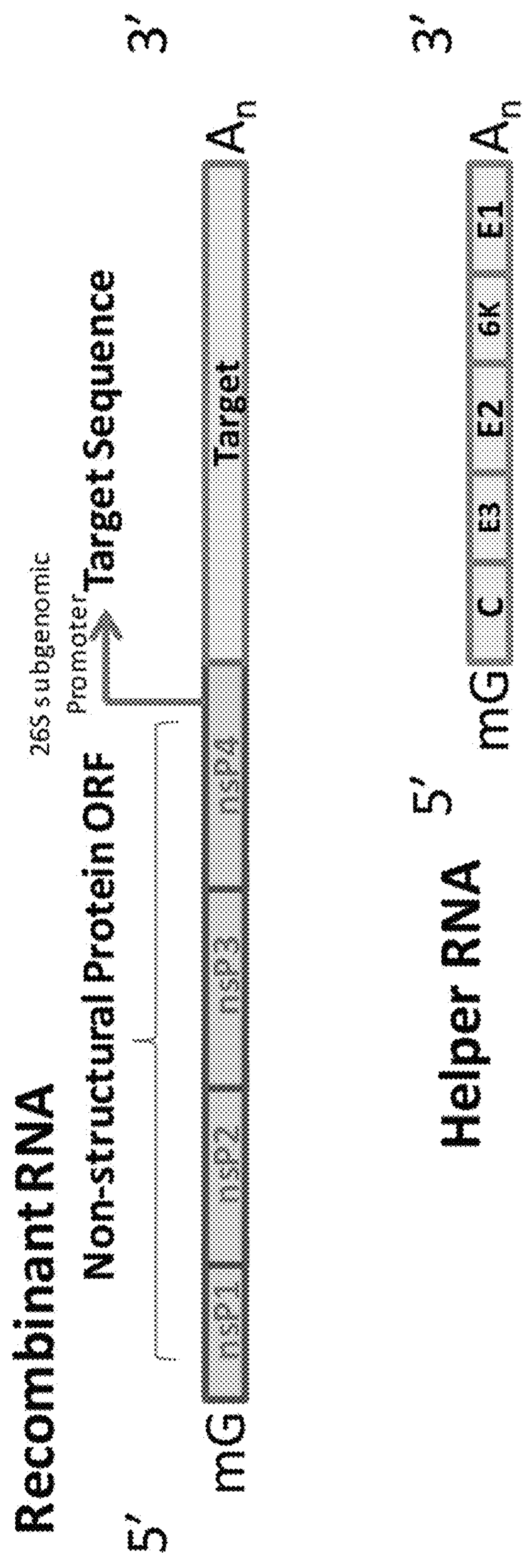
FIG. 2 shows a schematic depiction of the genomic organization of a Sindbis control vector of certain embodiments described herein.

As described herein, separation of the Sindbis viral genome into two ORF facilitates the manipulation of the viral genome through replacement of the genes coding for the structural proteins with target sequences. This modified genomic RNA can be transcribed in vitro and introduced into cells along with a helper RNA (e.g., encoding structural proteins not encoded for in the modified RNA genome) for the defective virus. In some embodiments, the helper RNA encodes the four structural proteins required for Sindbis Virus packaging. In some embodiments, the helper RNA does not contain a packaging signal, and so does not get incorporated into the assembled viral particles. Thus, in certain embodiments, the viral particles produced therefore contain the target sequences but are replication defective because they do not bear the genetic information to produce the structural proteins. The recombinant viruses produced are effective quality control materials since they bear the selected target sequences, but the design of the recombinant Sindbis system provided herein ensures that the virus particles are safe and are not capable of establishing continuous infection. This is a distinct advantage for these materials over patient sourced or cultured viral materials as controls. FIG. 2 illustrates transcribed RNAs used for assembly of replication defective recombinant viruses.

Assembly of the virus particle occurs at the plasma membrane. A heterodimer of the structural proteins. E1 and E2, inserts into the plasma membrane and the E2 cytoplasmic tail is thought to provide the binding site for the nucleocapsid. This interaction between E2 and the nucleocapsid is thought to initiate the actual budding and release of the virus. When recombinant Sindbis viruses are produced in cultured cells, the virus particles are collected from the culture media, where they typically reach concentrations greater than $1\times10^8$ viral copies/mL. The budding process results in the recombinant Sindbis virus being enveloped into a lipid bilayer. This is important since the structure of the recombinant virus is thus similar to many other viruses generally classified as RNA-containing enveloped viruses such as HIV-1, HCV. HTLV, Influenza, and SARS. Therefore, the replication deficient Sindbis vectors described herein can be a true whole process control as they undergo sample lysis and nucleic acid processing similar to human pathogenic viruses that may be found in patient samples.

In recombinant Sindbis viruses, the target sequences replace the structural genes. This gives the system great flexibility in the size of the target sequences that can be accommodated and packaged efficiently. Target sequences of less than 100 bp to greater than 4000 bp can be efficiently incorporated in the recombinant viruses. The ability to accommodate large sequences is a distinct advantage, especially when producing controls for multiplexed assays. Multiple target sequences (from different pathogens or from different genes within the same pathogen) can be combined in one recombinant virus to form a multiplex control.

In some embodiments, the Sindbis control viruses described herein comprise HIV-1 sequence and are therefore useful as a control for HIV-1 diagnostic assays. In some embodiments, the HIV-1 sequence in the Sindbis control virus is distinct from naturally occurring HIV-1 virus sequence in that it contains resistance mutations arising from multiple classes of current HIV-1 therapies. Such multiplexed mutations do not occur in nature. In some embodiments, the control virus has the various drug resistance mutations present at the same allelic ratio. This provides users with a clear expectation for their test results. In certain embodiments, stop codons are engineered into the HIV-1 sequences so that no functional HIV-1 proteins are produced.

In some aspects provided herein is an HIV-1 Sindbis control virus that comprises an HIV-1 sequence in its RNA genome. In some embodiments, the HIV-1 sequence comprises one or more mutations that, when present in a HIV-1 virus, conveys a drug resistance phenotype (e.g., resistance to a protease inhibitor, a nucleoside analogue reverse transcriptase inhibitor and/or a non-nucleoside analog reverse transcriptase inhibitor). For example, in some embodiments the HIV-1 virus sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29 or 30 mutations that convey a drug resistant phenotype. In some embodiments, the one or more mutations, when present in HIV-1 virus, convey resistance to a drug selected from the group consisting of: atazanavir, ritonavir, darunavir, fosamprenavir, indinavir, lopinavir, nelfinavir, saquinavir, tipranavir, abacavir, didanosine, emtricitabine, lamivudine, stavudine, tenofovir, zidovudine, efavirenz, etavirine, nevirapine or rilpivirine. In some embodiments, the one or more mutations are selected from the group consisting of L24I, D30N, V32I, M46I, 147V, G48V, 150V, 154M, G73S, L76V, V82A, 184V, N88D, L90M, M41L, K65R, D67N. T69S insert SS, K70R, L74V, F77L, Y115F, F116Y. Q151M, M184V, L210W, T215Y. K219Q, L100I, K101E, K103N, V106A, V1081, Y181C, Y188L, GI90A, P225H and M230L. In some embodiments, the one or more mutations are selected from the group consisting of L24I (TTA to ATA), D30N (GAT to AAT). V32I (GTA to ATA), M46I (ATG to ATA), 147V (ATA to CTA), G48V (GGG to GTG), 150V (ATT to GTT), 154M (ATC to ATG). G73S(GGT to GCT), L76V (TTA to GTA), V82A (GTC to GCC), 184V (ATA to GTA), N88D (AAT to GAT), L90M (TTG to ATG), M41L (ATG to TTG), K65R (AAA to AGA), D67N (GAC to AAC), T69S insert SS (ACT to TCT and insertion of TCC and TCC). K70R (AAA to AGA), L74V (TTA to GTA), F77L (TTC to CTC), Y115F (TAT to TTT). F116Y (T-T to TAT), Q51M (CAG to ATG). M184V (ATG to GTG), L210W (TTG to TGG), T215Y (ACC to TAC), K219Q (AAA to CAA), L100I (TTA to ATA), K101E (AAA to GAA), K103N (AAA to AAC), V106A (GTA to GCA), V1081 (GTA to ATA), Y181C (TAT to TGT), Y188L (TAT to TTA), G190A (GGA to GCA), P225H (CCT to CAT) and M230L (CCT to CAT). In some embodiments, the HIV-1 sequence comprises at least a portion of an HIV-1 gene selected from p7, p1, p6, HIV protease, reverse transcriptase, p51 RNAse, integrase and gp120. In some embodiments, the HIV-1 sequence comprises at least a portion of p7, p1, p6, HIV protease, reverse transcriptase and integrase. In certain embodiments, the HIV-1 sequence comprises at least a portion of 6p120, wherein the portion comprises the V1-V5 variable loops. In some embodiments, the HIV-I sequence comprises a sequence that is at least 80%, at least 85%, at least 900%, at least 91%, at least 92%, at least 93%, at least 94%, at least 95%, at least 96%, at least 97%, at least 98%, at least 99% or 100% identical to nucleotides 1900 through 5400 and/or 6300 through 7825 of the HXB2 strain of HIV-1 (SEQ ID NO. 4). In some embodiments, the HIV-1 sequence is identical to nucleotides 1900 through 5400 and/or 6300 through 7825 of the HXB2 strain of HIV-1 (SEQ ID NO: 4) except for the presence of the mutations that convey a drug resistance phenotype. In some embodiments, the heterologous RNA sequence comprises a sequence at least 80%, at least 85%, at least 90%, at least 91%, at least 92%, at least 93%, at least 94%, at least 95%, at least 96%, at least 97%, at least 98%, at least 99% or 100% identical to SEQ ID NO: 5 and/or SEQ ID NO: 7. In some embodiments, the heterologous RNA sequence comprises a sequence at least 80%, at least 85%, at least 90%, at least 91%, at least 92%, at least 93%, at least 94%, at least 95%, at least 96%, at least 97%, at least 98%, at least 99% or 100% identical to SEQ ID NO: 6 and/or SEQ ID NO: 8.

In some embodiments, the Sindbis control viruses described herein comprise Ebolavirus sequence and are therefore useful as a control for Ebolavirus diagnostic assays. In some embodiments, the Ebolavirus sequence comprises at least a portion of an Ebolavirus GP gene sequence, an Ebolavirus NP gene sequence or an Ebolavirus VP24 gene sequence. In some embodiments, the heterologous RNA sequence does not encode a functional Ebola protein (e.g., the heterologous RNA sequence encodes truncated Ebola proteins, Ebola proteins with frame-shift mutations and/or Ebola protein sequences lacking a start codon). In some embodiments, the heterologous RNA sequence comprises a sequence at least 80%, at least 85%, at least 90%, at least 910%, at least 92%, at least 93%, at least 94%, at least 95%, at least 96%, at least 97%, at least 98%, at least 99% or 100% identical to SEQ ID NO: 2 or SEQ ID NO: 3.

Figure 3:
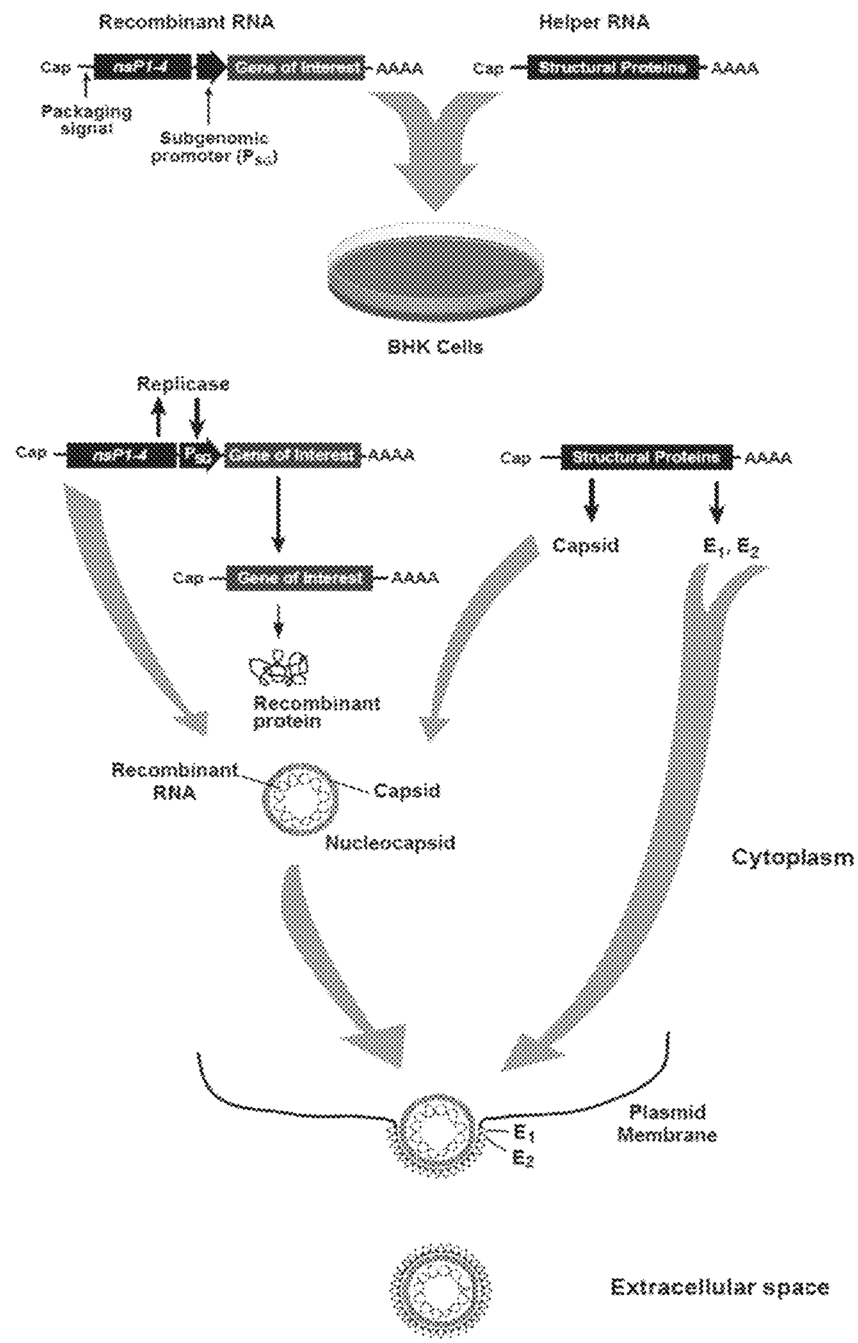
FIG. 3 shows an exemplary schematic for the production of recombinant Sindbis control viruses.

The Sindbis control viruses described herein can be generated using any method known in the art. An exemplary method of generating the Sindbis control viruses described herein is illustrated in FIG. 3. In this exemplary method, capped in vitro transcripts of recombinant RNA bearing sequence of interest and the helper RNA are first synthesized. The synthesized RNAs are then electroporated into an appropriate cell, such as a BHK cell. The Sindbis structural proteins are expressed, but since the RNA does not encode replicase enzymes, so no new RNA is transcribed. Recombinant RNA is packaged by the capsid proteins. Viral glycoproteins associate with the nucleocapsid and viral particles bud into the culture medium. The culture supernatant is then collected, filtered and heat inactivated. The viral titer can then be determined using an appropriate method, such as real-time PCR and appropriate quality control tests can be performed to ensure that the RNA is fully encapsulated and there is no contaminating template DNA.

Use of Sindbis Control Vectors in Nucleic Acid Diagnostic Assays

In certain aspects, provided herein are methods of testing a diagnostic assay by running the diagnostic assay on a composition comprising the replication deficient Sindbis virus described herein. In some embodiments, the diagnostic assay is an assay for the detection of Ebolavirus, an influenza virus, a SARS virus, a hepatitis C virus, a West Nile virus, a Zika virus, a poliovirus, a measles virus, an HIV-1 virus, an HIV-2 virus, an HTLV-I virus and/or an HTLV-II virus. In certain embodiments, the heterologous RNA sequence in the RNA genome of the replication deficient Sindbis virus contains the target sequence detected in the diagnostic assay.

In some embodiments, the diagnostic assay is a nucleic acid amplification based diagnostic assay. In some embodiments, the nucleic acid amplification based diagnostic assay includes a sample lysis step, a nucleic acid extraction step (e.g., a magnetic-bead based nucleic acid extraction step), a nucleic acid amplification step and/or a nucleic acid detection step. In some embodiments, the nucleic acid amplification and detection steps are performed simultaneously (e.g., through the use of a real-time detection technology, such as TaqMan probes or molecular beacons). Examples of nucleic acid amplification processes include, but are not limited to, polymerase chain reaction (PCR), LATE-PCR a non-symmetric PCR method of amplification, ligase chain reaction (LCR), strand displacement amplification (SDA), transcription mediated amplification (TMA), self-sustained sequence replication (3SR), Qβ replicase based amplification, nucleic acid sequence-based amplification (NASBA), repair chain reaction (RCR), boomerang DNA amplification (BDA) and/or rolling circle amplification (RCA).

In some embodiments, the diagnostic assay is a nucleic acid sequencing based diagnostic assay (e.g., a next-generation sequencing based diagnostic assay). In some embodiments, the nucleic acid sequencing based diagnostic assay includes a sample lysis step, a nucleic acid extraction step (e.g., a magnetic-bead based nucleic acid extraction step), a nucleic acid amplification step, and/or a nucleic acid sequencing step. Examples of nucleic acid sequencing processes include, but are not limited to chain termination sequencing, sequencing by ligation, sequencing by synthesis, pyrosequencing, ion semiconductor sequencing, single-molecule real-time sequencing, 454 sequencing, and/or Dilute-'N'-Go sequencing.

EXAMPLES

Example 1—Production of an Ebola Sindbis Control Virus

Ebola is a Filovirus with a single stranded, negative sense RNA genome. The Ebola virus genome includes the glycoprotein gene (GP) and the nucleoprotein gene (NP); these two genes were the targets of common nucleic acid-based diagnostic assays.

Ebola Sindbis Control virus was generated to serve as a control in such diagnostic assays. Recombinant Sindbis constructs were designed by cloning either about 2 kb of Ebola Zaire GP gene sequence (SEQ ID NO: 9) or about 1.5 kb of NP gene sequence and about 0.5 kb of a third Ebola gene, VP24 (SEQ ID NO: 10) into the Xba I restriction site of a SinRep SC vector (SEQ ID NO: 1). To ensure that no functional Ebola proteins would be produced, the constructs were designed to encode severely truncated GP and NP gene sequences. The GP constructs also lacked the AUG start codon for translation initiation and the NP construct contained a large internal deletion that changes the reading frame. Engineered stop codons were introduced in both constructs. These measures increase the safety of the product, but do not interfere with target detection (primer and probe binding) of the targeted diagnostic assays.

SEQ ID NO: 9 is an exemplary complete GP Ebola Sindbis control virus genome. Nucleotides 1 to 7652 and 9708 to 10080 of SEQ ID NO: 9 are Sindbis gene sequences, and nucleotides 7653 to 9707 of SEQ ID NO: 9 are Ebola GP insert sequences. SEQ ID NO: 10 is an exemplary complete NP/VP24 Ebola Sindbis control virus genome. Nucleotides 1 to 7652 and 9976 to 10348 of SEQ ID NO: 10 are Sindbis gene sequences, and nucleotides 7653 to 9975 of SEQ ID NO: 10 are Ebola NP/VP24 insert sequences.

Capped Ebola Sindbis control virus RNA was transcribed in vitro along with the helper RNA and introduced into baby hamster kidney cells. At 24 hours post-transfection, the cell supernatant was collected and the viral particles were purified and concentrated. Heat treatment was performed using a time and temperature known to inactivate similar RNA viruses as a further safety precaution. After titering the viruses using a TaqMan reverse transcription PCR assay, the viruses were combined and diluted into defibrinated human plasma containing human genomic DNA and 0.09% sodium azide as a preservative.

Three independent lots of the Ebola Sindbis control virus were tested in a real-time nucleic acid amplification based diagnostic assay developed for the detection of Ebola Zaire virus. The control material was processed identically to how an unknown patient sample would be processed. Representative results of this assay are shown in Table 1. In this table. Ct is the Cycle threshold value and SAC is the sample adequacy control (which verifies human source DNA in the sample).

TABLE 1

Ebola Sindbis control virus tested in a Ebola detection diagnostic assay.

| Sample ID | Input Volume | Test Result | GP Ct | NP Ct | SAC Ct |
|---|---|---|---|---|---|
| Lot 1 | 250 μL | Ebola GP DETECTED; Ebola NP DETECTED | 29.5 | 28.5 | 35.0 |
| Lot 2 | 250 μL | Ebola GP DETECTED; Ebola NP DETECTED | 30.6 | 29.5 | 34.9 |
| Lot 3 | 250 μL | Ebola GP DETECTED; Ebola NP DETECTED | 30.3 | 29.5 | 34.4 |

Example 2 Stability of an Ebola Sindbis Control Virus

Stability of quality control materials is critical, especially considering that for many automated systems, reagents are loaded onto the instrument and must be stable at ambient temperatures for extended periods. Thus, the stability of the Ebola Sindbis Control virus produced as described in Example 1 under various storage conditions was tested.

Figure 4:
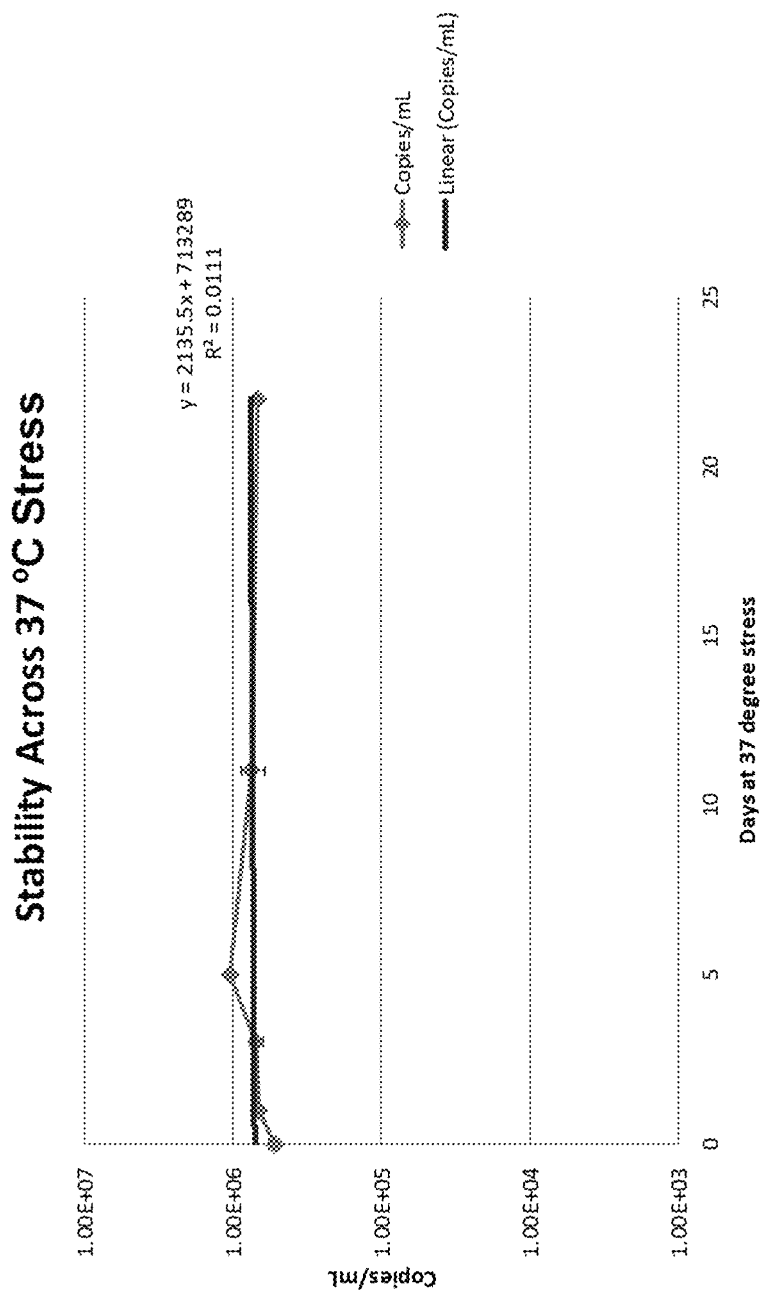
FIG. 4 shows the results of a TaqMan real time quantitation assay of Sindbis control samples unstressed (time=0) or stressed for 1, 3, 5, 11 or 22 days at 37° C.

Vials of the Ebola Sindbis Control virus produced as described in Example 1 were subjected to 37° C. At designated time points, vials were removed from the stress condition and extracted using the Qiagen QIAamp Viral RNA Mini Kit. Testing was performed via a TaqMan quantitative real time PCR assay. Results are shown in FIG. 4 and indicate no loss of stability after 22 days at 37° C. Using a model based on the Arrhenius equation, this stability at 37° C. correlates with a stability at a storage temperature of 2-8° C. of at least a 2 years.

Figure 5:
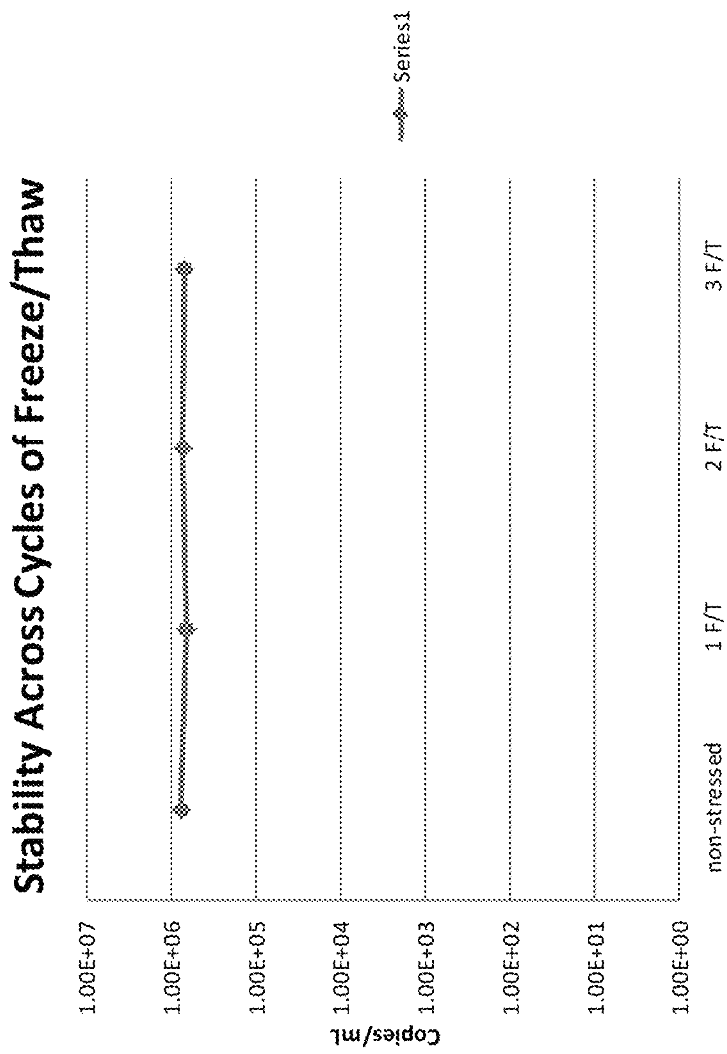
FIG. 5 shows the results of a TaqMan real time quantitation assay of non-stressed Sindbis control samples or samples stressed through one, two or three Freeze/Thaw cycles.
Figure 6:
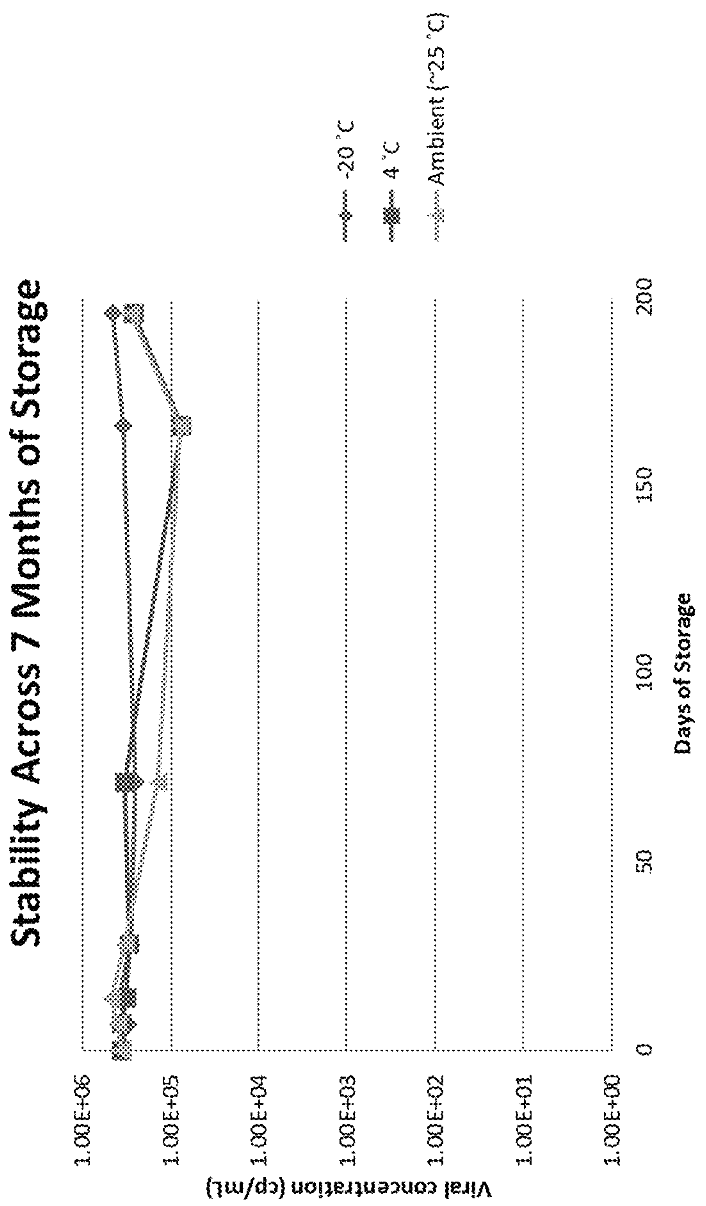
FIG. 6 shows the results of a TaqMan real time quantitation assay of a Sindbis control virus stored frozen at −20° C. stored refrigerated at 2-8° C. or stored at ambient lab temperature across seven months.

Vials of the Ebola Sindbis Control virus produced as described in Example 1 were subjected to multiple rounds of freezing and thawing (F/T). As shown in FIG. 5, subjecting the Sindbis control virus to three freeze-thaw cycles did not have an adverse effect on the stability of the virus.

To test the extended stability of a Sindbis control vector at various temperatures, a recombinant Sindbis virus (bearing 0.8 Kb of target sequence) was diluted into defibrinated human plasma at $5\times10^5$ copies/mL target concentration. The material was dispensed into vials and vials were stored frozen at −20° C. refrigerated at 2-8° C. or at ambient lab temperature (approximately 25° C.) for up to 200 days. Vials were tested periodically using a TaqMan real time PCR test. No loss of stability was detected across the seven months of storage, even for samples stored at ambient temperatures. This demonstrates that the viral coat proteins and envelop of the Sindbis virus form a stable protective barrier that prevents nucleases in complex clinical matrices such as plasma from degrading the target RNA sequence.

Example 3—Production of HIV-1 Multiplex Drug Resistance Sindbis Control Virus A Sindbis control virus was generated for use in diagnostic assays for the detection of drug resistant HIV-1 viruses.

The Los Alamos National Laboratory HIV Sequence Database was used to generate a "reference sequence" for the control virus. Based on this database as well as the publication Special Contribution Update of the Drug Resistance Mutations in HIV-1: March 2013 by Victoria A. Johnson et al., in Topics in Antiviral Medicine, mutations in the HIV-1 genome that confer resistance to which therapeutic drugs were identified. These mutations and drugs are summarized in Table 2.

TABLE 2

Drug resistant mutations of HIV included in the HIV-1 multiplex drug resistance Sindbis control virus.

| Drug Class | Therapy | Resistance Mutations | DNA Sequence change from reference sequence |
|---|---|---|---|
| Protease Inhibitors | Atazanavir +/− ritonavir | L24I | L24I (TTA to ATA) |
| | Darunavir/ritonavir | D30N | D30N (GAT to AAT) |
| | Fosamprenavir/ritonavir | V32I | V32I (GTA to ATA) |
| | Indinavir/ritonavir | M46I | M46I (ATG to ATA) |
| | Lopinavir/ritonavir | I47V | I47V (ATA to CTA) |
| | Nelfinavir | G48V | G48V (GGG to GTG) |
| | Saquinavir/ritonavir | I50V | I50V (ATT to GTT) |
| | Tipranavir/ritonavir | I54M | I54M (ATC to ATG) |
| | | G73S | G73S (GGT to GCT) |
| | | L76V | L76V (TTA to GTA) |
| | | V82A | V82A (GTC to GCC) |
| | | I84V | I84V (ATA to GTA) |
| | | N88D | N88D (AAT to GAT) |
| | | L90M | L90M (TTG to ATG |
| Nucleoside and | Abacavir | M41L | M41L (ATO to TTG) |
| Nucleotide Analogue | Didanosine | K65R | K65R (AAA to AGA) |
| Reverse | Emtricitabine | D67N | D67N (GAC to AAC) |
| Transcriptase | Lamivudine | T69S insert SS | T69S (ACT to TCT and |
| Inhibitors (NRTI) | Stavudine | | insertion of TCC TCC) |
| | Tenofovir | K70R | K70R (AAA to AGA) |
| | Zidovudine | L74V | L74V (TTA to GTA) |
| | | F77L | F77L (TTC to CTC) |
| | | Y115F | Y115F (TAT to TTT) |
| | | F116Y | F116Y (TTT to TAT) |
| | | Q151M | Q151M (CAG to ATG) |
| | | MI84VL210W | M184V (ATG to GTG) |
| | | T215Y | L210W (TTG to TGG) |
| | | K219Q) | T215Y (ACC to TAC) |
| | | | K219Q (AAA to CAA) |
| Non-Nucleoside | Efavirenz | L100I | L100I (TTA to ATA) |
| Analogue Reverse | Etravirine | K101E | K101E (AAA to GAA) |
| Transcriptase | Nevirapine | K103N | K103N (AAA to AAC) |
| Inhibitors (NNRTI) | Rilpivirine | V106A | V106A (GTA to GCA) |
| | | V108I | V108I (GTA to ATA) |
| | | Y181C | Y181C (TAT to TGT) |
| | | Y188L | Y188L (TAT to TTA) |
| | | G190A | G190A (GGA to GCA) |
| | | P225H | P225H (CCT to CAT) |
| | | M230L | M230L (ATG to CTG) |

In addition to the mutations described above, virus entry inhibitor drugs such as Miraviroc are blocked by mutations in the envelop gene. This drug is a CC chemokine receptor 5 (CCR5) antagonists and is only effective for patients with virus that uses the CCR5 co-receptor for viral entry. Viruses that use both CCR5 and CXC chemokine receptor 4 (CXCR4) or only CXCR4 w ill not respond to treatment with CCR5 antagonists. A virus's ability to use CXCR4 co-receptor is not defined by a single mutation, but instead is determined by the sequence of several variable "loops" in the gp120 envelop gene.

HXB2 strain of HIV-1 is a CXCR4 utilizing virus. HXB2 sequence is available from the Los Alamos National Laboratory HIV Sequence Database. Its sequence was used in the development of the recombinant virus representing the mutant CXCR4 virus. BaL strain of HIV-1 uses exclusively CCR5 co-receptor. Its sequence was obtained from the NCI database and used in the development of recombinant Sindbis virus representing wild type CCR5 virus.

Four DNA sequences were chemically synthesized and cloned into the Xba I restriction site of a SinRep SC Sindbis expression plasmid (SEQ ID NO: 1), which bears genes required for Sindbis virus production. Four Sindbis control viruses were generated, one that contained the 5' end of a wild-type HIV-1 genome, one that contained the 5' end of a multidrug resistant HIV-1 viral genome, one that contained the 3' end of a wild-type HIV-1 genome and one that contained the 3' end of a multidrug resistant HIV-I viral genome. The insert sequences for these four control viruses are described in Table 3.

TABLE 3

Description of recombinant virus sequences.

| Construct Designation | Genes included in the sequence | HXB2-Nucleotide Positions |
|---|---|---|
| 5' multi-mutant (SEQ ID NO: 11) | part of p7, p1, p6, Protease, RT, p51 RNAse and Integrase | Contains continuous sequence from nucleotides 1900 through 5400. The mutations shown in Table 1 are incorporated |

TABLE 3-continued

| Description of recombinant virus sequences. | | |
|---|---|---|
| Construct Designation | Genes included in the sequence | HXB2-Nucleotide Positions |
| 5' WT (SEQ ID NO: 12) | part of p7, p1, p6, Protease, RT, p51 RNAse and Integrase | Contains continuous sequence from nucleotides 1900 through 5400. |
| 3' mutant (SEQ ID NO: 13) | A portion of gp120 including V1-V5 variable loops | nucleotides 6300-7825 of HXB2 sequence are included |
| 3' WT (SEQ ID NO: 14) | A portion of gp120 including V1-V5 variable loops | The BaL sequence which corresponds to HXB2 6300-7825 (as determined by BLAST alignment) is included |

SEQ ID NO: 11 is the DNA counterpart to an exemplary complete 5' multi-mutant HIV-1 Sindbis control virus genome. Nucleotides 1 to 7646 and 11167 to 11655 indicate Sindbis gene sequences, and nucleotides 7647 to 1166 indicate multi-mutant HIV-I insert sequences. SEQ ID NO: 12 is the DNA counterpart to an exemplary complete 5' wild-type HIV-1 Sindbis control virus genome. Nucleotides 1 to 7646 and 11161 to 11649 indicate Sindbis gene sequences, and nucleotides 7647 to 11160 indicate wild-type HIV-1 insert sequences. SEQ ID NO. 13 is the DNA counterpart to an exemplary complete 3' mutant HIV-1 Sindbis control virus genome. Nucleotides 1 to 7646 and 9187 to 9675 indicate Sindbis gene sequences, and nucleotides 7647 to 9186 indicate mutant HIV-1 insert sequences. SEQ ID NO: 14 is the DNA counterpart to an exemplary complete 3' wild-type HIV-1 Sindbis control virus genome. Nucleotides 1 to 7646 and 9182 to 9670 indicate Sindbis gene sequences, and nucleotides 7647 to 9181 indicate wild-type HIV-1 insert sequences.

Figure 7:
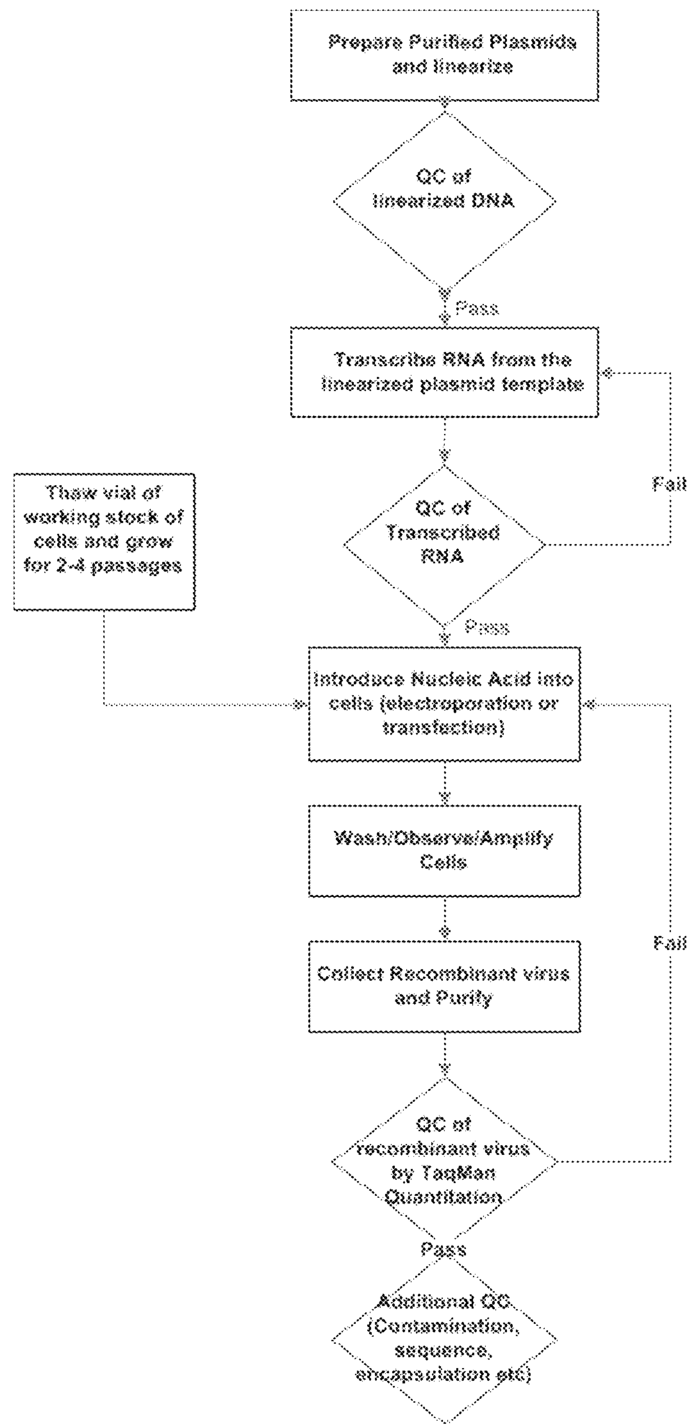
FIG. 7 shows a workflow overview for the production of Sindbis control virus.
Figure 8:
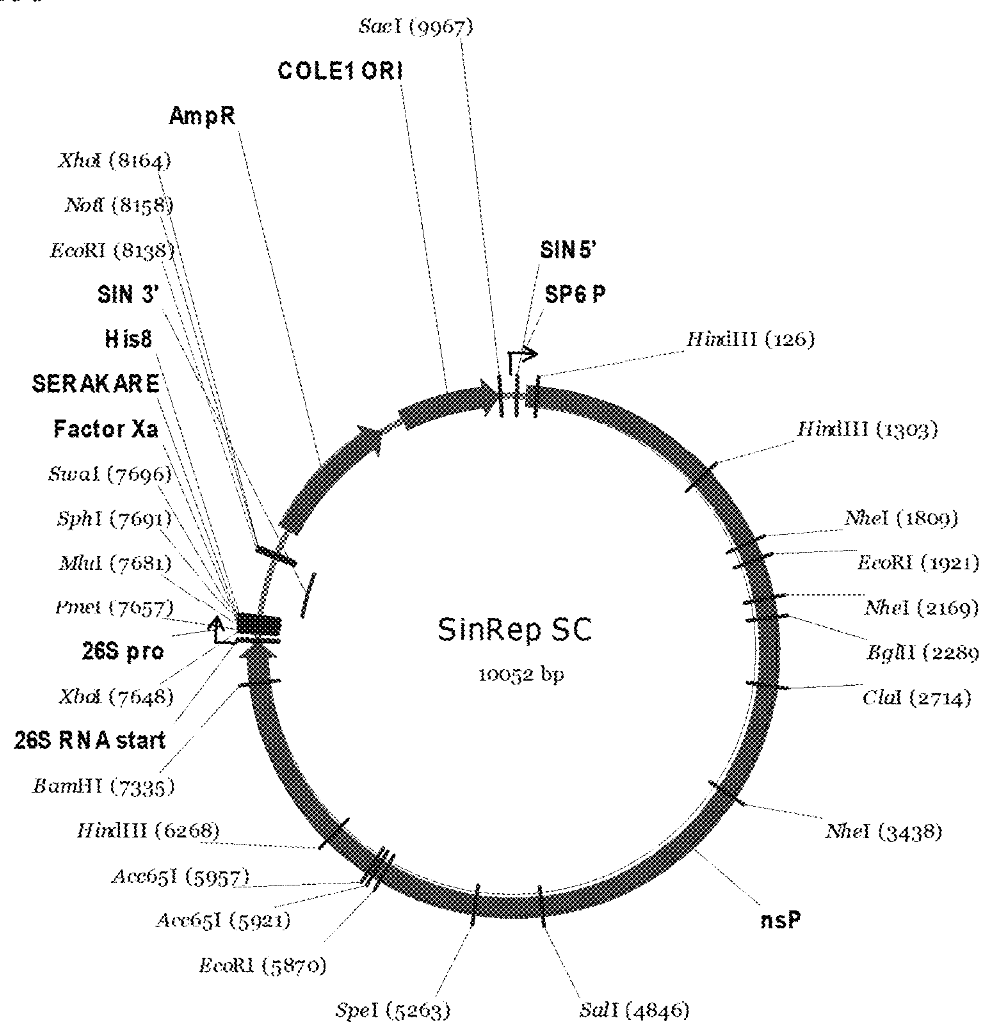
FIG. 8 shows a map of the SinRep SC vector. Figure discloses “His8” as SEQ ID NO: 16.

The process used to produce the recombinant HIV-I Sindbis control viruses is outlined in FIG. 7. Briefly plasmids that contain the target HIV-1 sequences in the SinRep vector were linearized with Not 1 restriction enzyme. An aliquot was analyzed by agarose gel electrophoresis to ensure that DNA cutting is complete.

Ambion mMessage mMachine SP6 kit was used for in vitro transcription of large amounts of capped RNA using reaction conditions optimized for long transcripts. DHBB is a helper RNA needed for packaging of the replication defective Sindbis virus, this helper RNA was transcribed from a linearized plasmid as well. The integrity and identity of the transcribed RNA was analyzed by denaturing agarose gel electrophoresis. The RNA was treated with DNAse to remove template plasmid DNA and purified using Ambion MegaClear kit.

To ensure optimal cell viability, BHK-21 (Baby Hamster Kidney cells) were amplified in culture for 2-4 passages after revival of frozen stock. Immediately prior to electroporation, the fetal bovine serum in the culture media was reduced, which helps reduce this cell's tendency to form clumps. Preventing cell clumps is desirable to maximize the transfection efficiency during electroporation.

The in vitro transcribed RNA was introduced into the BHK-21 cells via electroporation. The cells were washed at 6 hours post transfection to remove any unincorporated RNA.

The in vitro transcribed RNAs (HIV-1 sequences in SinRep RNA and DHBB helper RNA) were translated within the cells to produce the proteins required for recombinant Sindbis virus assembly and budding. The recombinant viruses were released into the culture media. The culture media was collected at 24 hours post transfection. The crude viral supernatant and the purified viruses were titered by extracting the viral nucleic acids using the Qiagen QIAamp Viral RNA mini kit and then using quantitative TaqMan real time PCR assay which targets a portion of the Sindbis viral vector RNA.

Example 4—Production of a Zika Sindbis Control Virus

Figure 9:
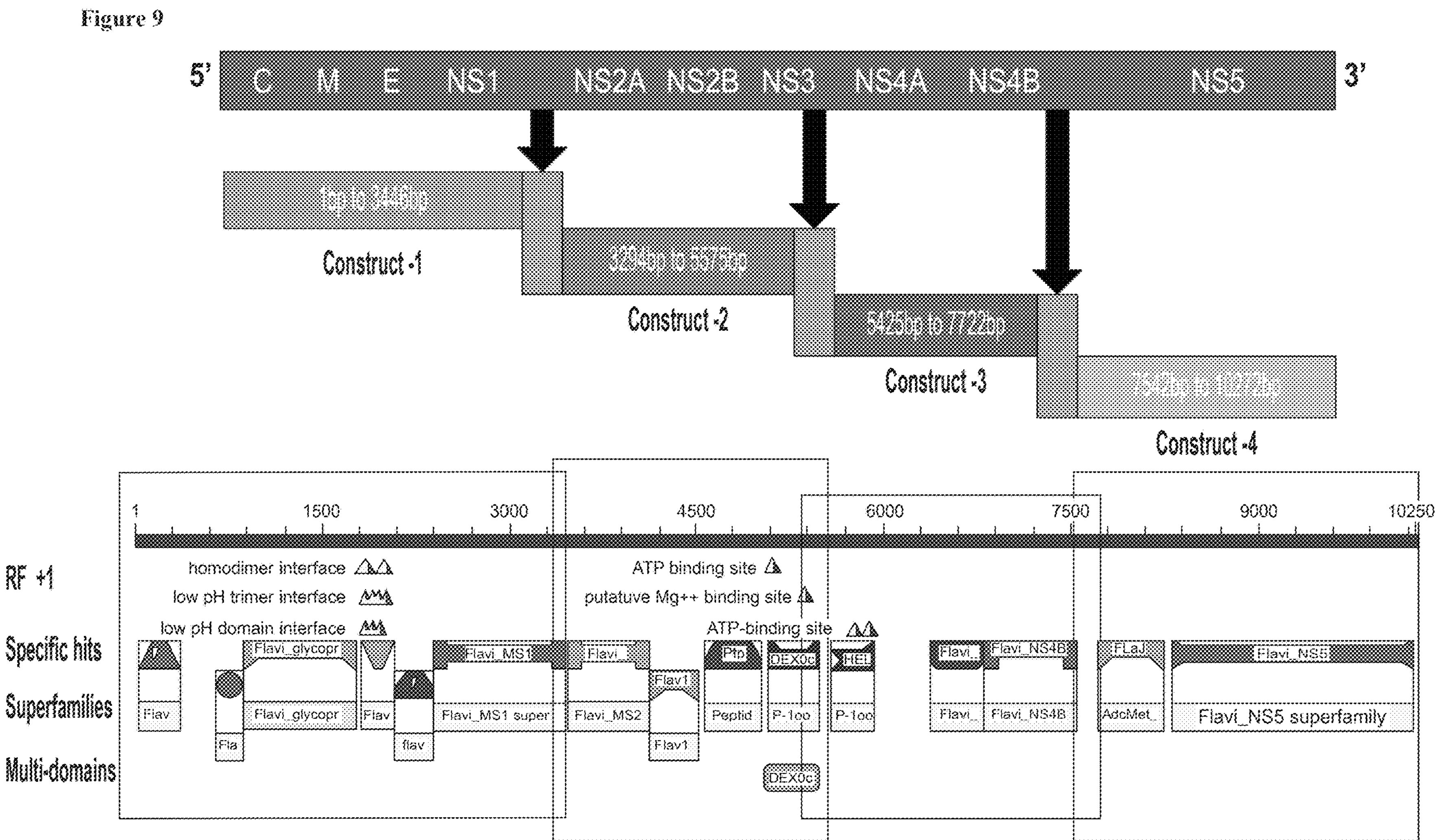
FIG. 9 consists of two maps of the Zika virus genome. The genome was divided into four regions for the construction of four different Zika virus reference materials, and each region is depicted by a rectangle. A first reference material comprises nucleotides 1 to 3446 of the Zika virus from GenBank Accession number EU545988.1, referred to as the "Zika Env Construct" (Construct −1). A second reference material comprises nucleotides 3294 to 5575, referred to as the "Zika NS2/NS3 Construct" (Construct −2). A third reference material comprises nucleotides 5425 to 7722, referred to as the "Zika NS4 Construct" (Construct −3). A fourth reference material comprises nucleotides 7542 to 10272, referred to as the "Zika NS5 Construct" (Construct −4).

Zika virus is a positive-sense, single-stranded RNA molecule of about 10794 bases long, and it codes a single polyprotein that is subsequently cleaved into capsid (C), precursor membrane (prM), envelope (E), and non-structural proteins (NS). Zika virus reference materials were designed based on a 2007 Zika virus strain with GenBank Accession number EU545988.1 (SEQ ID NO: 15). For the Zika Reference Materials, this genome was divided across four different constructs with at least ~150 bp overlap between constructs and breakpoints at the ends of conserved domains. The overlap design is shown in FIGS. 9 and 10.

There was a 152 bp overlap between the "Zika Env" and "Zika NS2/NS3" construct, 150 bp overlap between "Zika NS2/NS3" and "Zika NS4" construct and 180 bp overlap between "Zika NS4" and "Zika NS5" constructs. These overlaps are designed to cover any diagnostic assays that target the ends of conserved domains. All four constructs were synthesized and introduced into Sindbis plasmids, which were used to prepare recombinant Sindbis virus.

The recombinant Zika/Sindbis virus were expressed, and high titer stock solutions of the viruses were prepared. The high titer stock solutions of recombinant Zika/Sindbis virus were diluted 1:100 in PBS, and RNA was extracted and eluted into 120 μL of 1:10 diluted AVE buffer. Extracted RNA was assayed by droplet digital PCR using a one-step RT-ddPCR master mix (Bio-Rad, 186-4021) at neat and 1:10 dilutions. Vector specific primer/probe sets were used for quantifying all four constructs as shown in Table 4.

TABLE 4

| Quantification of Zika Construct Copy Numbers in Zika Virus Reference Materials | | | | | |
|---|---|---|---|---|---|
| Sample | Copies Per 20 μL Well | Copies per μL of Extracted RNA | Average copies per μL Extracted RNA | Copies per mL of Extracted Sample | Back calculated copies per mL stock |
| Zika Env | 3580 | 716 | 6.81E+02 | 5.84E+05 | 5.84E+07 |
| Zika Env | 2800 | 560 | | | |
| Zika Env | 3840 | 768 | | | |
| Zika Env 1:10 | 396 | 79.2 | 7.84E+01 | 6.72E+04 | 6.72E+07 |
| Zika Env 1:10 | 388 | 77.6 | | | |

TABLE 4-continued

Quantification of Zika Construct Copy Numbers in Zika Virus Reference Materials

| Sample | Copies Per 20 μL Well | Copies per μL of Extracted RNA | Average copies per μL Extracted RNA | Copies per mL of Extracted Sample | Back calculated copies per mL stock |
|---|---|---|---|---|---|
| Zika Env 1:10 | 392 | 78.4 | | | |
| Zika NS2/NS3 | 6040 | 1208 | 1.20E+03 | 1.03E+06 | 1.03E+08 |
| Zika NS2/NS3 | 6360 | 1272 | | | |
| Zika NS2/NS3 | 5580 | 1116 | | | |
| Zika NS2/NS3 1:10 | 692 | 138.4 | 1.27E+02 | 1.09E+05 | 1.09E+08 |
| Zika NS2/NS3 1:10 | 636 | 127.2 | | | |
| Zika NS2/NS3 1:10 | 578 | 115.6 | | | |
| Zika NS4 | 6460 | 1292 | 1.29E+03 | 1.10E+06 | 1.10E+08 |
| Zika NS4 | 5380 | 1076 | | | |
| Zika NS4 | 7480 | 1496 | | | |
| Zika NS4 1:10 | 532 | 106.4 | 1.33E+02 | 1.14E+05 | 1.14E+08 |
| Zika NS4 1:10 | 750 | 150 | | | |
| Zika NS4 1:10 | 718 | 143.6 | | | |
| Zika NS5 | 2528 | 505.6 | 5.33E+02 | 4.57E+05 | 4.57E+07 |
| Zika NS5 | 2268 | 453.6 | | | |
| Zika NS5 | 3200 | 640 | | | |
| Zika NS5 1:10 | 264 | 52.8 | 5.13E+01 | 4.40E+04 | 4.40E+07 |
| Zika NS5 1:10 | 196 | 39.2 | | | |
| Zika NS5 1:10 | 310 | 62 | | | |

Based on the high titer stock concentration, a 35 mL bulk was formulated at 5.0E+05 copies/mL in filtered human plasma (Basematrix) containing 0.09% $NaN_3$ diluent and human genomic DNA (H9 DNA, 50 ng/mL). A Pall Acropak 1000 Filter Capsule (PES RM-1002220) was used for filtering the plasma. To 900 mL of filtered plasma, 810 mg of sodium azide and 45 μg of human genomic DNA was added and mixed for 15 minutes. All four constructs were targeted to 5.0E+05 copies/mL in the prepared bulk. Bulk was mixed thoroughly for about 15 minutes, and RNA was extracted in triplicate and assayed using ddPCR with a One-Step RT-PCR mastermix from Bio-Rad Laboratories (Catalogue 186-4021). Assay specific primers/probe were used to quantify each construct. Data is shown in Table 5.

TABLE 5

Quantification of Zika Construct Copy Numbers in Zika Virus Reference Materials Formulated with Human Plasma

| Sample | Conc. | Copies per 20 μL Well | Copies per μL of Extracted RNA | Copies per mL of bulk | Average Copies per mL of bulk |
|---|---|---|---|---|---|
| Zika Env | 50.8 | 1016 | 203.2 | 1.74E+05 | 1.72E+05 |
| Zika Env | 48.6 | 972 | 194.4 | 1.67E+05 | |
| Zika Env | 50.7 | 1014 | 202.8 | 1.74E+05 | |
| Zika NS2/NS3 | 33.6 | 672 | 134.4 | 1.15E+05 | 1.22E+05 |

TABLE 5-continued

Quantification of Zika Construct Copy Numbers in Zika Virus Reference Materials Formulated with Human Plasma

| Sample | Conc. | Copies per 20 μL Well | Copies per μL of Extracted RNA | Copies per mL of bulk | Average Copies per mL of bulk |
|---|---|---|---|---|---|
| Zika NS2/NS3 | 37.3 | 746 | 149.2 | 1.28E+05 | |
| Zika NS2/NS3 | 36.2 | 724 | 144.8 | 1.24E+05 | |
| Zika NS4 | 125.6 | 2512 | 502.4 | 4.31E+05 | 4.07E+05 |
| Zika NS4 | 117.2 | 2344 | 468.8 | 4.02E+05 | |
| Zika NS4 | 113.1 | 2262 | 452.4 | 3.88E+05 | |
| Zika NS5 | 207 | 4140 | 828 | 7.10E+05 | 6.88E+05 |
| Zika NS5 | 197 | 3940 | 788 | 6.75E+05 | |
| Zika NS5 | 198 | 3960 | 792 | 6.79E+05 | |

An Altona Realstar Zika RT-PCR assay was performed on the extracted RNA from prepared bulk. The Altona Zika RT-PCR assay is a qualitative assay that gives a Positive or Negative result as shown in Table 6. Data is shown for both Zika and internal control analytes. The internal control (IC Zika (JOE)) should be detected in all negative and positive wells for a valid result, whereas Zika signal (Zika (FAM)) should be detected only in Positive wells. Bulk was tested in five replicates with Ct values around 28. Negative control was undetermined as expected, and the positive control Ct was 32.

TABLE 6

Altona Realstar Zika RT-PCR Assay Performed on Zika Virus Reference Materials Formulated with Human Plasma

| Well | Sample Name | Detector | Task | Ct | Result |
|---|---|---|---|---|---|
| A1 | Zika Bulk | Zika (FAM) | Unknown | 28.4665 | POSITIVE |
| A1 | Zika Bulk | IC Zika (JOE) | Unknown | 30.7525 | VALID |
| A2 | Zika Bulk | Zika (FAM) | Unknown | 28.5619 | POSITIVE |
| A2 | Zika Bulk | IC Zika (JOE) | Unknown | 30.9062 | VALID |
| A3 | Zika Bulk | Zika (FAM) | Unknown | 28.5517 | POSITIVE |
| A3 | Zika Bulk | IC Zika (JOE) | Unknown | 30.9627 | VALID |
| A4 | Zika Bulk | Zika (FAM) | Unknown | 28.7069 | POSITIVE |
| A4 | Zika Bulk | IC Zika (JOE) | Unknown | 31.0635 | VALID |

TABLE 6-continued

Altona Realstar Zika RT-PCR Assay Performed on Zika Virus Reference Materials Formulated with Human Plasma

| Well | Sample Name | Detector | Task | Ct | Result |
|---|---|---|---|---|---|
| A5 | Zika Bulk | Zika (FAM) | Unknown | 28.6494 | POSITIVE |
| A5 | Zika Bulk | IC Zika (JOE) | Unknown | 31.0911 | VALID |
| C1 | Negative control | Zika (FAM) | NTC | Undetermined | NEGATIVE |
| C1 | Negative control | IC Zika (JOE) | NTC | 30.8181 | VALID |
| C2 | Positive Control | Zika (FAM) | Unknown | 32.0931 | POSITIVE |
| C2 | Positive Control | IC Zika (JOE) | Unknown | 30.809 | VALID |

6 mL of prepared bulk was sent to a commercial laboratory for bioburden testing. The bioburden result was 0 cfu/mL for bacterial growth and the Zika reference materials passed the acceptance criteria (<100 cfu/mL or No growth).

Extracted viral RNA from recombinant Sindbis virus was sequence-verified by Sanger sequencing. All four constructs were PCR amplified at the beginning and end of the insert, and each nucleotide sequence displayed 100% sequence homology with the EU545988.1 sequence used to design the constructs (SEQ ID NO:15).

Example 5—Stability of an Influenza Sindbis Control Virus

Figure 11A:
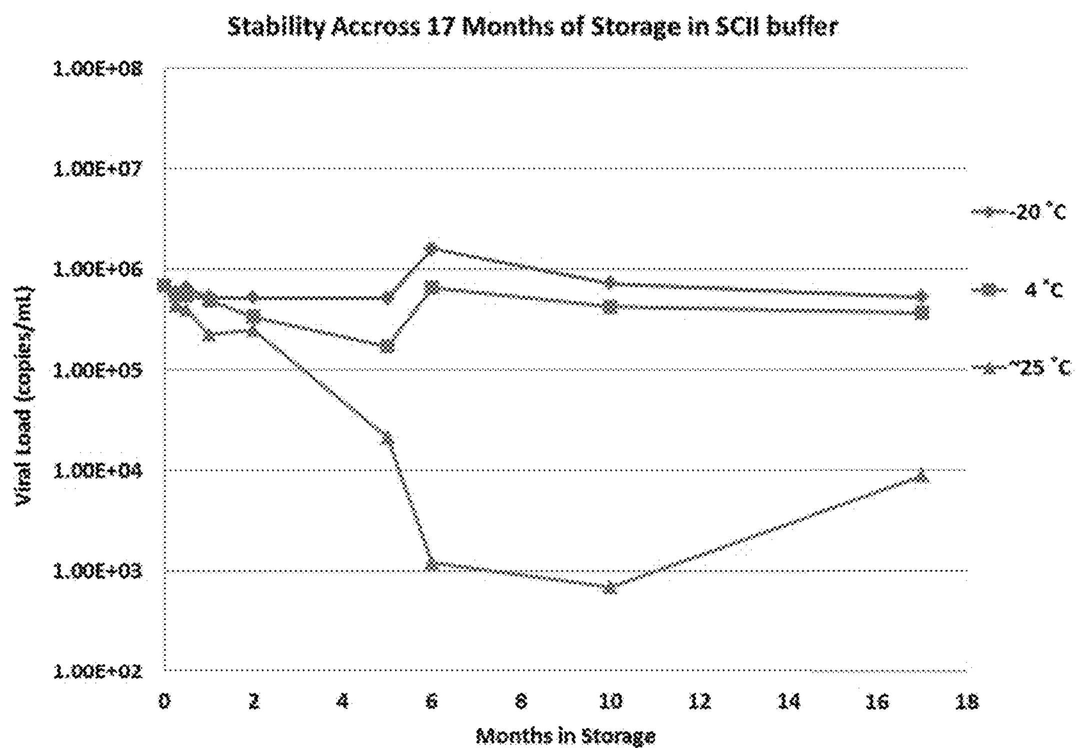
FIG. 11A shows stability results of TaqMan real time quantitation of an H7N9 influenza reference material stored at −20° C., 4° C., or room temperature (~25°) for seventeen months. The results depicted are for reference materials formulated with buffer.
Figure 11B:
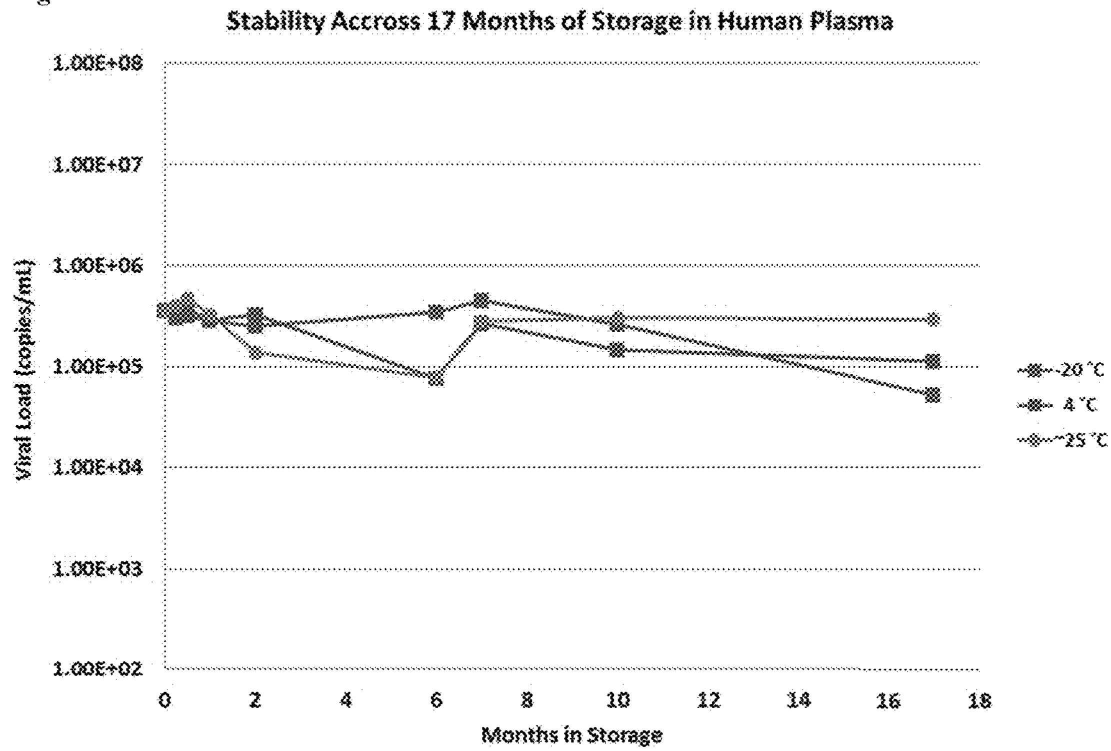
FIG. 11B shows stability results of TaqMan real time quantitation of an H7N9 influenza reference material stored at −20° C., 4° C., or room temperature (~25°) for seventeen months. The results depicted are for reference materials formulated with human plasma.
Figure 12:
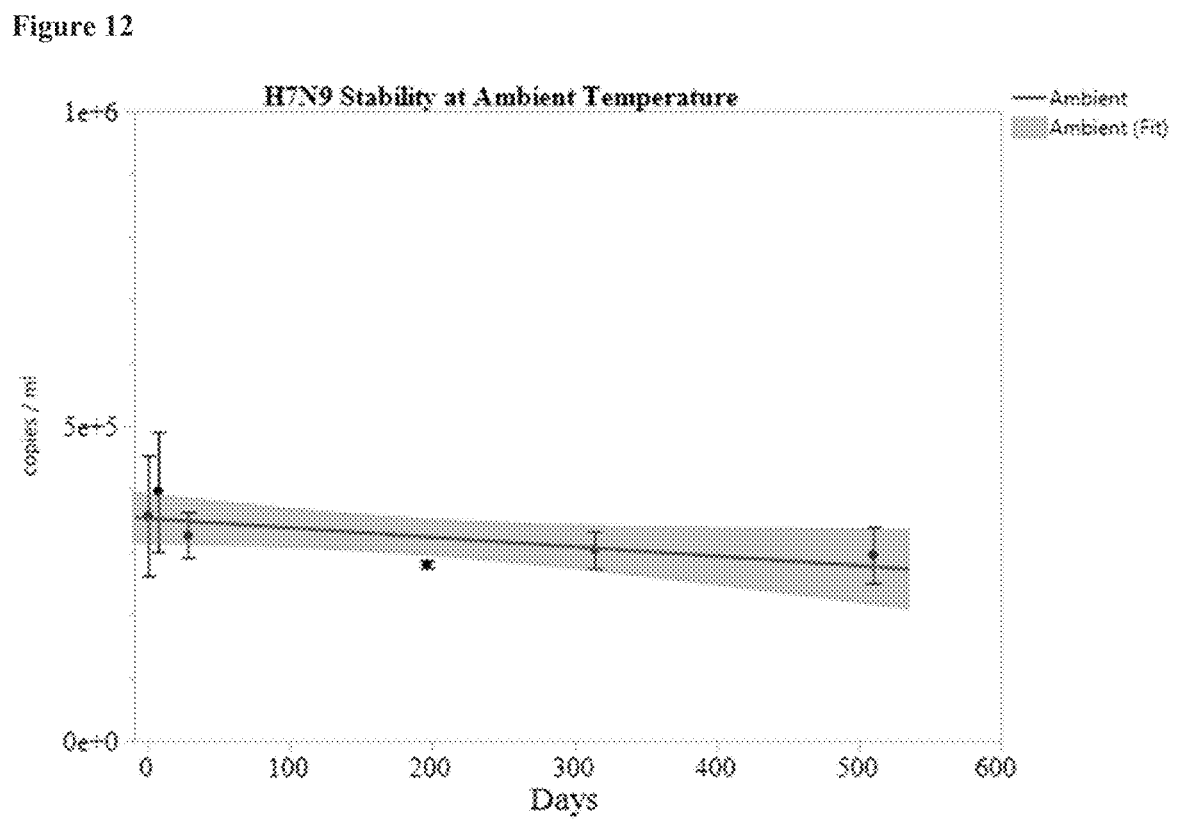

An influenza reference material comprising an 800-nucleotide sequence of the H7N9 influenza virus was constructed using methods similar to those described above. The influenza reference material was diluted into aqueous buffer or defibrinated human plasma at $5\times10^5$ copies/mL in a commutable matrix. The material was dispensed into vials and stored at −20° C., 4° C., or room temperature (~25° C.). Vials were tested periodically using a laboratory developed H7N9 TaqMan real time PCR test. As shown in FIGS. 11 and 12, the influenza reference material stored at ambient temperature for 500 days was stable as only ~15% loss of signal was observed. This stability profile suggests that the viral coat and envelope proteins form a stable protective barrier that prevents nucleases in complex clinical matrices (such as plasma) from degrading the target RNA sequence.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of testing a diagnostic assay, comprising performing the diagnostic assay on a control comprising replication deficient recombinant Sindbis virus particles comprising an RNA genome comprising:

an open reading frame (ORF) encoding functional Sindbis non-structural proteins; and a heterologous RNA sequence comprising a non-Sindbis RNA virus sequence or a retrovirus sequence; wherein the non-Sindbis virus sequence is an Ebolavirus sequence, a SARS virus sequence, a West Nile virus sequence, a Zika virus sequence, a poliovirus sequence or a measles virus sequence;

wherein the diagnostic assay is a nucleic acid amplification based diagnostic assay or a nucleic acid sequencing based diagnostic assay comprising:

a) performing a lysis step and/or a nucleic acid extraction step on the composition comprising the replication deficient recombinant Sindbis virus particles; and b) performing a nucleic acid amplification step or performing a nucleic acid sequencing step on RNA extracted from the replication deficient recombinant Sindbis virus particles; and wherein the diagnostic assay detects the presence or amplification of an RNA virus or a retrovirus; and the diagnostic assay is valid if the heterologous RNA sequence or its amplification is detected.

2. The method according to claim 1, wherein the ORF encoding functional Sindbis non-structural proteins:

(a) is located 5' of the heterologous RNA sequence; and/or (b) has a nucleotide sequence that is at least 90% identical to nucleotides 1-7648 of SEQ ID NO: 1; and/or (c) has a nucleotide sequence of nucleotides 1-7648 of SEQ ID NO: 1.

3. The method according to claim 1, wherein:

(a) the RNA genome lacks a sequence encoding a functional version of one or more of the Sindbis structural proteins, optionally wherein the RNA genome lacks an RNA sequence encoding a functional Sindbis structural protein; or (b) the heterologous RNA sequence replaces the ORF encoding the Sindbis structural proteins in the RNA genome.

4. The method according to claim 1, wherein:

(a) the non-structural protein ORF encodes a nsP1 protein, a nsP2 protein, a nsP3 protein and a nsP4 protein; and/or (b) the RNA genome comprises a 26S subgenomic promoter at the 3' end of the ORF encoding the Sindbis non-structural proteins; and/or (c) the heterologous RNA sequence comprises a non-Sindbis RNA virus sequence or a retrovirus sequence.

5. The method according to claim 1, wherein:

(a) the heterologous RNA sequence comprises one or more, or at least 5, or at least 10 mutations that convey drug resistance when they occur in the non-Sindbis RNA virus or the retrovirus; and/or (b) the heterologous RNA sequence comprises at least 100 bp, or 100-330 kb of a non-Sindbis RNA virus sequence or a retrovirus sequence; and/or (c) the heterologous RNA sequence comprises a non-Sindbis RNA virus sequence or a retrovirus sequence.

6. The method according to claim 1, wherein heterologous RNA sequence comprises a non-Sindbis RNA virus sequence and wherein the non-Sindbis RNA virus sequence is:

(a) a Zaire ebolavirus sequence, a Bundibugyo ebolavirus sequence, a Reston ebolavirus sequence, a Sudan ebolavirus sequence or a Tai Forest ebolavirus sequence;

(b) a Zaire ebolavirus sequence;

(c) an Ebolavirus sequence wherein the Ebolavirus sequence comprises at least a portion of an Ebolavirus GP gene sequence, an Ebolavirus NP gene sequence or an Ebolavirus VP24 gene sequence;

(d) an Ebolavirus sequence wherein the heterologous RNA sequence does not encode a functional Ebola protein, optionally wherein the heterologous RNA sequence encodes truncated Ebola proteins, Ebola proteins with frame-shift mutations or Ebola protein sequences lacking a start codon; or (e) a Zaire ebolavirus sequence wherein the heterologous RNA sequence comprises a sequence at least 90% identical to SEQ ID NO: 2 or SEQ ID NO: 3 optionally wherein the heterologous RNA sequence comprises SEQ ID NO: 2 or SEQ ID NO: 3.

7. The method according to claim 1, wherein the RNA genome comprises:

(a) a nucleotide sequence that is at least 90% identical to SEQ ID NO: 9 or SEQ ID NO: 10;

(b) SEQ ID NO: 9 or SEQ ID NO: 10;

(c) a nucleotide sequence that is at least 90% identical to either nucleotides 1-3446 of SEQ ID NO: 15, nucleotides 3294-5575 of SEQ ID NO: 15, nucleotides 5425-7722 of SEQ ID NO: 15, or nucleotides 7542-10272 of SEQ ID NO: 15; or (d) either nucleotides 1-3446 of SEQ ID NO: 15, nucleotides 3294-5575 of SEQ ID NO: 15, nucleotides 5425-7722 of SEQ ID NO: 15, or nucleotides 7542-10272 of SEQ ID NO: 15.

8. The method according to claim 1, wherein the diagnostic assay is for the detection of an RNA virus or a retrovirus.

9. The method according to claim 8, wherein the RNA virus is an enveloped non-Sindbis RNA-containing virus or a retrovirus.

10. The method according to claim 8, wherein the virus is:

(a) Ebolavirus;

(b) a SARS virus;

(c) a hepatitis C virus;

(d) a West Nile virus;

(e) a Zika virus;

(f) a poliovirus; or (g) a measles virus.

11. The method according to claim 1, wherein the heterologous RNA sequence comprises:

(a) at least 10, at least 50, at least 100, at least 150, at least 200, at least 300, at least 350, at least 400, at least 450, at least 500, at least 600, at least 650, at least 700, at least 750, at least 800, at least 850, at least 900, at least 950, at least 1000, at least 1100, at least 1200, at least 1300, at least 1400, at least 1500, at least 1600, at least 1700, at least 1800, at least 1900, or at least 2000 bp of a non-Sindbis RNA virus sequence or a retrovirus sequence; or (b) 100-300 bp or 100-200 bp of a non-Sindbis RNA virus sequence or a retrovirus sequence.

* * * * *